(12) United States Patent  
Boer et al.

(10) Patent No.: US 11,297,862 B2  
(45) Date of Patent: Apr. 12, 2022

(54) STEVIOL GLYCOSIDE TRANSPORT

(71) Applicant: DSM IP ASSETS B.V., Heerlen (NL)

(72) Inventors: Viktor Marius Boer, Echt (NL); Priscilla Zwartjens, Echt (NL); Eric Van Den Berg, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/751,674

(22) PCT Filed: Aug. 15, 2016

(86) PCT No.: PCT/EP2016/069356  
§ 371 (c)(1),  
(2) Date: Feb. 9, 2018

(87) PCT Pub. No.: WO2017/025648  
PCT Pub. Date: Feb. 16, 2017

(65) Prior Publication Data  
US 2018/0235263 A1   Aug. 23, 2018

Related U.S. Application Data

(60) Provisional application No. 62/204,702, filed on Aug. 13, 2015.

(51) Int. Cl.  
C07K 14/39    (2006.01)  
C12P 19/56    (2006.01)  
(Continued)

(52) U.S. Cl.  
CPC .......... A23L 27/36 (2016.08); A23L 2/60 (2013.01); C07K 14/39 (2013.01); C07K 14/395 (2013.01);  
(Continued)

(58) Field of Classification Search  
CPC ............ C12N 1/20; C12N 9/88; C07K 14/40  
See application file for complete search history.

(56) References Cited

U.S. PATENT DOCUMENTS

2015/0031868 A1   1/2015 Lehmann et al.  
2016/0153017 A1   6/2016 Van Der Hoeven et al.  
(Continued)

FOREIGN PATENT DOCUMENTS

CN       103732753 A      4/2014  
WO       2004/026043 A1   4/2004  
(Continued)

OTHER PUBLICATIONS

H. Guo et al., "Protein Tolerance to Random Amino Acid Change", PNAS 101(25): 9205-9210. (Year: 2004).*  
(Continued)

Primary Examiner — Tekchand Saidha  
(74) Attorney, Agent, or Firm — McBee Moore & Vanik IP, LLC; Susan McBee; Chester Moore

(57) ABSTRACT

A recombinant host capable of producing a steviol glycoside which overexpresses a polypeptide which mediates steviol glycoside transport and which polypeptide comprises the amino acid sequence set forth in SEQ ID NO: 29 or an amino acid sequence having at least about 50% sequence identity thereto. A recombinant host capable of producing a steviol glycoside which has been modified, preferably in its genome, to result in a deficiency in the production of a polypeptide which mediates steviol glycoside transport and which polypeptide comprises the amino acid sequence set forth in SEQ ID NO: 29 or an amino acid sequence having at least about 50% sequence identity thereto.

8 Claims, 21 Drawing Sheets  
Specification includes a Sequence Listing.

(51) Int. Cl.
  A23L 27/30    (2016.01)
  A23L 2/60     (2006.01)
  C12P 15/00    (2006.01)
  C07K 14/395   (2006.01)
  C07K 14/40    (2006.01)
  C12N 1/16     (2006.01)
  C12N 9/24     (2006.01)

(52) U.S. Cl.
  CPC ............... *C07K 14/40* (2013.01); *C12N 1/16* (2013.01); *C12N 9/2402* (2013.01); *C12P 15/00* (2013.01); *C12P 19/56* (2013.01)

(56) References Cited

U.S. PATENT DOCUMENTS

| | | |
|---|---|---|
| 2016/0160257 A1 | 6/2016 | Broers et al. |
| 2016/0177360 A1 | 6/2016 | Boer et al. |

FOREIGN PATENT DOCUMENTS

| | | |
|---|---|---|
| WO | 2004/032648 A1 | 4/2004 |
| WO | 2013110673 A1 | 8/2013 |
| WO | 2014122328 A1 | 8/2014 |
| WO | 2014191581 A2 | 12/2014 |
| WO | 2015/007748 A1 | 1/2015 |
| WO | 2015011209 A1 | 1/2015 |

OTHER PUBLICATIONS

Mottram, Donald S. et al., "Acrylamide is formed in the Maillard reaction", Nature, Oct. 3, 2002, pp. 448-449, vol. 419.
Tareke, E. et al., "Acrylamide: A Cooking Carcinogen?", Chemical Research in Toxicology, 2000, pp. 517-522, vol. 13.
International Search Report issued in counterpart International Application No. PCT/EP2016/069357, dated Nov. 18, 2016.
Dujon et al., "Genome evolution in yeasts" Database, Uniprot: Q6c4M7. (Aug. 16, 2004) p. 1.
Bowie, J.U. et al., "A method to identify protein sequences that fold into a known three-dimensional structure", Science, Jul. 12, 1991, pp. 164-170, vol. 253, No. 5016.
Chothia, Cyrus et al., "The relation between the divergence of sequence and structure in proteins", The EMBO Journal, 1986, pp. 823-826, vol. 5, No. 4.
NG, Pauline C. et al., "Predicting Deleterious Amino Acid Substitutions", Genome Research, 2001, pp. 863-874, vol. 11.
Henikoff, Steven et al., "Amino acid substitution matrices from protein blocks", Proceedings of the National Academy of Sciences of the United States of America, Nov. 1992, pp. 10915-10919, vol. 89.
Ho, Steffan N. et al., "Site-directed mutagenesis by overlap extension using the polymerase chain reaction", Gene, Apr. 15, 1989, pp. 51-59, vol. 77, No. 1.
Huelsenbeck, John P. et al., "Bayesian analysis of amino acid substitution models", Philosophical Transactions of the Royal Society B, Oct. 7, 2008, Abstract.
Landt, Olfert et al., "A general method for rapid site-directed mutagenesis using the polymerase chain reaction", Gene, 1990, pp. 125-128, vol. 96, No. 1.
NG, Pauline C. et al., "Predicting the Effects of Amino Acid Substitutions on Protein Function", Annual Review of genomics and Human Genetics, 2006, pp. 61-80, vol. 7.
Taylor, W.R., "Pattern matching methods in protein sequence comparison and structure prediction", Protein Engineering, Design and Selection, Jul. 1988, pp. 77-86, vol. 2, No. 2.
Villoutreix, Bruno, "Mutations or Variations", VLS3D.com, Sep. 15, 2020.
Muller, Tobias et al., "Estimating Amino Acid Substitution Models: A Comparison of Dayhoff's Estimator, the Resolvent Approach and a Maximum Likelihood Method", Molecular Biology and Evolution, Jan. 2002, pp. 8-13, vol. 19, No. 1.
Kruskal, Joseph, "An Overview of Sequence Comparison: Time Warps, String Edits, and Macromolecules", SIAM Review, Apr. 1983, p. 201, vol. 25, No. 2.

* cited by examiner

STEVIOL GLYCOSIDE TRANSPORT

CROSS-REFERENCE TO RELATED APPLICATIONS

This application is a § 371 National Stage Application of PCT/EP2016/069356, filed 15 Aug. 2016, and claims benefit to U.S. Provisional Application No. 62/204,702, filed 13 Aug. 2015.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-344001_ST25.txt" created on 8 Feb. 2018, and 72,855 bytes in size) is submitted concurrently with the instant application, and the entire contents of the Sequence Listing are incorporated herein by reference.

BACKGROUND

Field of the Invention

The present invention relates to a recombinant host capable of producing a steviol glycoside. The invention also relates to a process for the preparation of a steviol glycoside using such a recombinant host. The invention also relates to a fermentation broth comprising a steviol glycoside, a steviol glycoside and to a composition comprising two or more steviol glycosides. The invention further relates to a foodstuff, feed or beverage which comprises a steviol glycoside or a composition comprising two or more steviol glycosides.

DESCRIPTION OF RELATED ART

The leaves of the perennial herb, *Stevia rebaudiana* Bert., accumulate quantities of intensely sweet compounds known as steviol glycosides. Whilst the biological function of these compounds is unclear, they have commercial significance as alternative high potency sweeteners.

These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in *Stevia* leaves where they may comprise from 10 to 20% of the leaf dry weight. Stevioside and rebaudioside A are both heat and pH stable and suitable for use in carbonated beverages and many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in *Stevia* leaves. It may be about 200 times sweeter than sucrose. Rebaudioside M is a further high-potency diterpene glycoside sweetener. It is present in trace amounts in certain *stevia* variety leaves, but has been suggested to have a superior taste profile.

Steviol glycosides have traditionally been extracted from the *Stevia* plant. In *Stevia*, (−)-kaurenoic acid, an intermediate in gibberellic acid (GA) biosynthesis, is converted into the tetracyclic diterpene steviol, which then proceeds through a multi-step glycosylation pathway to form the various steviol glycosides. However, yields may be variable and affected by agriculture and environmental conditions. Also, *Stevia* cultivation requires substantial land area, a long time prior to harvest, intensive labour and additional costs for the extraction and purification of the glycosides.

More recently, interest has grown in producing steviol glycosides using fermentative processes. WO2013/110673 and WO2015/007748 describe microorganisms that may be used to produce at least the steviol glycosides rebaudioside A, rebaudioside D and rebaudioside M.

Further improvement of such microorganisms is desirable in order that higher amounts of steviol glycosides may be produced and/or additional or new steviol glycosides and/or higher amounts of specific steviol glycosides and/or mixtures of steviol glycosides having desired ratios of different steviol glycosides.

SUMMARY OF THE INVENTION

The present invention is based on the identification of a protein which is capable of mediating steviol glycoside transport.

Accordingly, the protein may be overexpressed in a recombinant host (such as a microbial cell) in order to increase steviol glycoside transport out of the host. Alternatively, a host (such as a microbial cell) may be modified so as to express less of the protein than a corresponding non-modified version of the host. In this case, more steviol glycoside may be retained within the host which is then glycosylated to a steviol glycoside comprising a higher number of sugar moieties.

Thus, the invention relates to a recombinant host, for example a cell such as a microbial cell, which produces steviol glycoside outside the host to a greater degree than a corresponding host not overexpressing the protein. This may facilitate easier recovery of steviol glycosides. The invention also relates to a recombinant host capable of producing a steviol glycoside which overexpresses a heterologous polypeptide which mediates steviol glycoside transport.

Accordingly, the invention relates to a recombinant host capable of producing a steviol glycoside which overexpresses a polypeptide which mediates steviol glycoside transport and which polypeptide comprises the amino acid sequence set forth in SEQ ID NO: 29 or an amino acid sequence having at least about 50% sequence identity thereto.

The invention also relates to a recombinant host capable of producing a steviol glycoside which has been modified, preferably in its genome, to result in a deficiency in the production of a polypeptide which mediates steviol glycoside transport and which polypeptide comprises the amino acid sequence set forth in SEQ ID NO: 29 or an amino acid sequence having at least about 50% sequence identity thereto.

The invention also relates to a recombinant host which comprises steviol glycosides (inside and/or outside the host) having a higher or lower average glycosylation number than a corresponding host not modified according to the invention.

The invention also relates to:
 a process for the preparation of a steviol glycoside which comprises fermenting a recombinant host according to any one of the preceding claims in a suitable fermentation medium and, optionally, recovering the steviol glycoside;
 a fermentation broth comprising a steviol glycoside obtainable by a process of the invention;

a steviol glycoside obtained by a process or a fermentation broth of the invention;

a composition comprising two or more steviol glycosides of the invention or obtainable by a process of the invention;

a foodstuff, feed or beverage which comprises a steviol glycoside or a composition of the invention.

DESCRIPTION OF THE SEQUENCE LISTING

Figure 1:
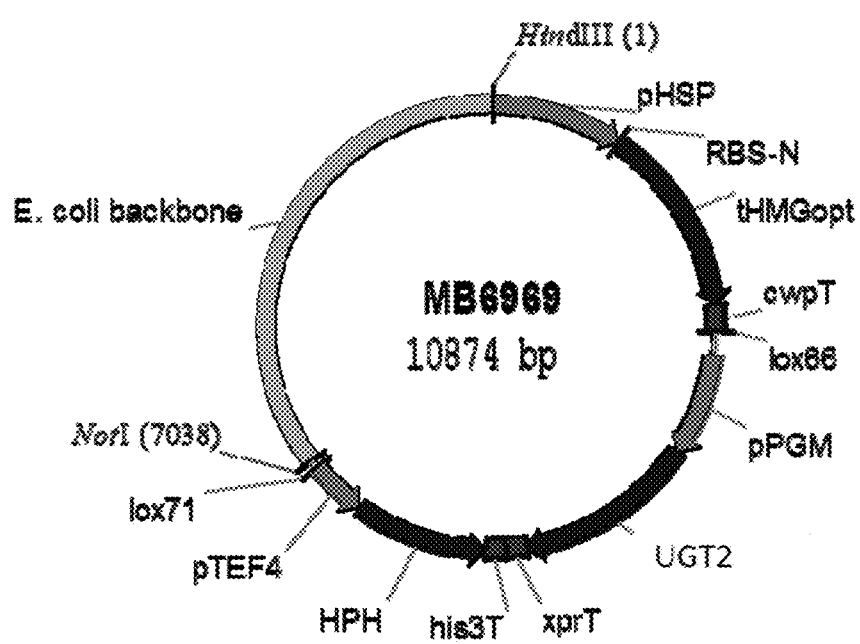
FIG. 1 sets out a schematic representation of the plasmid MB6969, encoding tHMG, UGT2_1a, HPH.

A description of the sequences is set out in Table 14. Sequences described herein may be defined with reference to the sequence listing or with reference to the database accession numbers also set out in Table 14.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The invention relates to the identification of a polypeptide which is capable of mediating steviol glycoside transport. Such a polypeptide may directly mediate steviol glycoside transport, i.e. may be a transporter protein, or may indirectly mediate steviol glycoside transport. Such a polypeptide may be capable of mediating transport of one or more steviol glycoside.

The invention relates to a recombinant host either overexpressing or having reduced expression of such a polypeptide. The terms recombinant host or recombinant cell may, depending on the context, be used interchangeably.

Such a polypeptide as described herein may be overexpressed in a recombinant host, such as a recombinant host cell, capable of producing one or more steviol glycosides. Such a cell may be capable of producing more of one or more steviol glycosides external to the cell than a corresponding cell which does not overexpress the polypeptide. That is to say, a recombinant cell according to the invention may have increased or decreased steviol glycoside transport in a comparison with a corresponding non-recombinant cell.

Accordingly, the invention provides a recombinant host capable of producing a steviol glycoside which overexpresses a polypeptide, the polypeptide being one which is capable of mediating steviol glycoside transport and which polypeptide comprises the amino acid sequence set forth in SEQ ID NO: 29 or an amino acid sequence having at least about 50% sequence identity thereto.

The expression of such a polypeptide may also be modified in a host, such as a recombinant host cell, such that it is reduced compared to a corresponding cell which has not been similarly modified. In this way, the amount of one or more steviol glycosides outside the cell may be reduced in comparison with a corresponding cell which has not been similarly modified. This may allow for increased glycosylation of one or more steviol glycosides within the cell compared with a corresponding cell which has not been similarly modified. Such a host may thus comprise steviol glycosides having a higher average glycosylation number compared with a corresponding cell which has not been similarly modified.

Accordingly, the invention provides a recombinant host capable of producing a steviol glycoside which has been modified, preferably in its genome, to result in a deficiency in the production of a polypeptide, the polypeptide being one which is capable of mediating steviol glycoside transport and which polypeptide comprises the amino acid sequence set forth in SEQ ID NO: 29 or an amino acid sequence having at least about 50% sequence identity thereto.

A host cell of the invention is a recombinant host cell. "Recombinant" in this sense means that the host cell is a non-naturally occurring host cell, for example modified by introduction of one or more nucleic acids using recombinant techniques. A nucleic acid used to modify a host cell to arrive at a recombinant host cell of the invention may be a naturally-occurring nucleic acid or a non-naturally occurring nucleic acid.

Thus, when used in reference to a host of the invention, "recombinant" indicates that a cell has been modified by the introduction of one or more heterologous nucleic acid or protein or the alteration of a native nucleic acid or protein, or that the cell is derived from a cell so modified. The term "heterologous" as used herein refers to nucleic acid or amino acid sequences not naturally occurring in a host cell. In other words, the nucleic acid or amino acid sequence is not identical to that naturally found in the host cell.

The invention relates to a recombinant host capable of producing a steviol glycoside which overexpresses a heterologous polypeptide which mediates steviol glycoside transport. Such a heterologous polypeptide may be obtained from or derived from a genus or species other than that of the host. Accordingly, if the recombinant host is a yeast, the heterologous polypeptide which mediates steviol glycoside transport may be obtained from or derived from a different genus or species of yeast.

For example, if the host cell is a *Saccharomyces* (e.g., *S. cerevisiae, S. bayanus, S. pastorianus, S. carlsbergensis*), the heterologous polypeptide which mediates steviol glycoside transport may be obtained from or derived from a *Candida* (e.g., *C. krusei, C. revkaufi, C. pulcherrima, C. tropicalis, C. utilis*), an *Issatchenkia* (eg. *I. orientalis*) or a *Yarrowia* (e.g., *Y. lipolytica* (formerly classified as *Candida lipolytica*)).

For example, if the host cell is a *Candida* (e.g., *C. krusei, C. revkaufi, C. pulcherrima, C. tropicalis, C. utilis*), the heterologous polypeptide which mediates steviol glycoside transport may be obtained from or derived from a *Saccharomyces* (e.g., *S. cerevisiae, S. bayanus, S. pastorianus, S. carlsbergensis*), an *Issatchenkia* (eg. *I. orientalis*) or a *Yarrowia* (e.g., *Y. lipolytica* (formerly classified as *Candida lipolytica*)).

For example, if the host cell is an *Issatchenkia* (eg. *I. orientalis*), the heterologous polypeptide which mediates steviol glycoside transport may be obtained from or derived from a *Saccharomyces* (e.g., *S. cerevisiae, S. bayanus, S. pastorianus, S. carlsbergensis*), a *Candida* (e.g., *C. krusei, C. revkaufi, C. pulcherrima, C. tropicalis, C. utilis*) or a *Yarrowia* (e.g., *Y. lipolytica* (formerly classified as *Candida lipolytica*)).

For example, if the host cell is a *Yarrowia* (e.g., *Y. lipolytica* (formerly classified as *Candida lipolytica*)), the heterologous polypeptide which mediates steviol glycoside transport may be obtained from or derived from a *Saccharomyces* (e.g., *S. cerevisiae, S. bayanus, S. pastorianus, S. carlsbergensis*). a *Candida* (e.g., *C. krusei, C. revkaufi, C. pulcherrima, C. tropicalis, C. utilis*) or an *Issatchenkia* (eg. *I. orientalis*).

If the host cell is *Saccharomyces cerevisiae*, the heterologous polypeptide which mediates steviol glycoside transport may be obtained from or derived from *Yarrowia lipolytica* (formerly classified as *Candida lipolytica*)), *Candida krusei* or *Issatchenkia orientalis*.

If the host cell is *Yarrowia lipolytica*, the heterologous polypeptide which mediates steviol glycoside transport may be obtained from or derived from *Saccharomyces cerevisiae*, *Yarrowia lipolytica* (formerly classified as *Candida lipolytica*)) or *Candida krusei* or *Issatchenkia orientalis*.

If the host cell is *Candida krusei* or *Issatchenkia orientalis*, the heterologous polypeptide which mediates steviol glycoside transport may be obtained from or derived from *Saccharomyces cerevisiae* or *Yarrowia lipolytica*.

The term "derived from" also includes the terms "originated from," "obtained from," "obtainable from," "isolated from," and "created from," and generally indicates that one specified material find its origin in another specified material or has features that can be described with reference to the another specified material. As used herein, a substance (e.g., a nucleic acid molecule or polypeptide) "derived from" a microorganism may indicate that the substance is native to that microorganism or is a substance native to that microorganism, but may also indicate a substance that has been altered from a native version.

Thus, for example, a recombinant cell may express a polypeptide as defined herein not found within the native (non-recombinant) form of the cell. Alternatively, a recombinant cell may be modified so as to express a native gene encoding a polypeptide as defined herein to a greater degree than takes place within the native "non-recombinant" form of the cell.

Alternatively, a recombinant cell may be modified so as to express a native gene encoding a polypeptide as defined herein to a lesser degree than takes place within the native "non-recombinant" form of the cell.

In a cell of the invention, a polypeptide as defined herein may be overexpressed. Herein, "overexpressed", "overexpression" or the like implies that the recombinant host cell expresses more of the polypeptide than a corresponding cell which does not overexpress the polypeptide or, alternatively, that the polypeptide is expressed in a cell which would not typically express that protein. Alternatively, overexpression may be achieved by expressing a variant polypeptide having a higher specific activity.

A recombinant cell of the invention cell may be modified, preferably in its genome, to result in a deficiency in the production of a polypeptide as defined herein.

Such a cell may be from a parent host cell and be modified, preferably in its genome, if compared to the parent host cell to obtain a different genotype and/or a different phenotype if compared to the parent host cell from which it is derived.

Such a cell which has been modified, preferably in its genome, to result in a deficiency in the production of a polypeptide as defined herein, is a mutant host cell which has been modified, preferably in its genome, to result in a phenotypic feature wherein the cell: a) produces less of the product or produces substantially no product and/or b) produces a product having a decreased activity or decreased specific activity or a product having no activity or no specific activity and combinations of one or more of these possibilities as compared to the parent microbial host cell that has not been modified, when analyzed under the same conditions.

The term "recombinant" is synonymous with "genetically modified".

Such a recombinant host may be a full or partial knock-out of a nucleic acid sequence encoding a polypeptide as described herein.

The invention thus concerns recombinant hosts overexpressing or deficient in a polypeptide identified as having steviol glycoside transport mediating activity: typically, the host is one which may be used for the production of steviol glycosides. The ability of a given recombinant host to produce a steviol glycoside may be a property of the host in non-recombinant form or may be a result of the introduction of one or more recombinant nucleic acid sequences (i.e. encoding enzymes leading to the production of a steviol glycoside).

For the purpose of this invention, a polypeptide having steviol glycoside transport mediating activity (i.e. a polypeptide which mediates steviol glycoside transport) is one which has an effect on transport of one or more steviol glycosides across a cell membrane. The effect may be direct, i.e. the polypeptide may be a transporter protein or comprise a functional transporter region. Alternatively, the effect may be indirect, i.e. the polypeptide is not a transporter protein, but its activity nevertheless has an effect on steviol glycoside transport.

Typically, the effect will be such that increasing the level of expression of the polypeptide increases the amount of transport of one or more steviol glycosides across the membrane of a cell (in comparison with a corresponding cell having a lower level of expression of the polypeptide). Conversely, decreasing the level of expression of the polypeptide may decrease the amount of transport of one or more steviol glycosides across the membrane of a cell (in comparison with a corresponding cell having a higher level of expression of the polypeptide).

Typically, a recombinant host of the invention is capable of producing a steviol glycoside. For example, a recombinant host of the invention may be capable of producing one or more of, for example but not limited to, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebA, rebB, rebC, rebD, rebE or rebM. A recombinant host of the invention may be capable of producing one or more of the steviol glycosides set out in Ceunen and Geuns, Journal of Natural Products 76(6), 1201-1228, 2013.

Thus, a cell of the invention may be one in which the amount of total amount of steviol glycosides outside the cell as compared with inside the cell is greater or less than compared with a corresponding cell which either does not overexpress or does not have a reduced level of expression of a cell of the invention.

Alternatively, a cell of the invention may have the same total amount of steviol glycosides outside the cell as compared with inside the cell compared with a corresponding cell which either does not overexpress or does not have a reduced level of expression of a cell of the invention, but may have an altered distribution of steviol glycosides inside and outside the cell.

Thus, a recombinant host of the invention is capable of producing a steviol glycoside. For example, a recombinant host of the invention may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebA, rebB, rebC, rebD, rebE or rebM.

Thus, a recombinant host of the invention may be one in which at least about 10%, at least about 20%, at least about 30%, at least about 40%, at least about 50% of the rebA produced by the cell is outside the cell.

Thus, a recombinant host of the invention may be one in which at least about 10%, at least about 20%, at least about 30%, at least about 40%, at least about 50% of the rebD produced by the cell is outside the cell.

Thus, a recombinant host of the invention may be one in which at least about 10%, at least about 20%, at least about 30%, at least about 40%, at least about 50% of the rebM produced by the cell is outside the cell.

A recombinant cell of the invention may be one in which no more than about 50%, no more than about 40%, no more than about 30%, no more than about 20%, no more than about 10% of the rebA produced by the cell is outside the cell.

A recombinant cell of the invention may be one in which no more than about 50%, no more than about 40%, no more than about 30%, no more than about 20%, no more than about 10% of the rebD produced by the cell is outside the cell.

A recombinant cell of the invention may be one in which no more than about 50%, no more than about 40%, no more than about 30%, no more than about 20%, no more than about 10% of the rebM produced by the cell is outside the cell.

A recombinant cell of the invention may be one where the average glycosylation number of the steviol glycosides is at least 3, at least 4, at least 5, at least 6 or more. The average glycosylation number may be increased or decreased in comparison with a corresponding cell not modified according to the invention. For example, average glycosylation may decrease when a polypeptide as described herein is overexpressed. For example, average glycosylation may increase (in particular in a cell itself) when expression of a polypeptide of the invention is reduced.

The average glycosylation may refer to that in the supernatant of a recombinant cell of the invention or to the average glycosylation in the broth (pellet+supernatant).

The invention thus provides a recombinant cell capable of producing a steviol glycoside either overexpressing or deficient in the expression of a polypeptide comprising the amino acid sequence set forth in SEQ ID NO: 29 or an amino acid sequence having at least about 50% sequence identity thereto. Such an amino acid sequence has an effect of steviol glycoside transport, i.e. is a mediator of steviol glycoside transport.

The polypeptide may also be defined as one comprising the following amino acid sequence (or an amino acid sequence having at least about 45% sequence identity thereto):

```
                                        (SEQ ID NO: 29)
MGKTEVTQESLECGSVTSSLGKKPFSIITLFTGRRIPPVPTEKPDSAEER

AGILSKLTWQWLSPLLKTGYLRNIEREDLYKVRERNSAAVIQQRLESNLE

KQYAKYHAKLLKKGLSEQEAHLKLQDSAKPLVLALNQTFFWKFWLAGLFA

LVKDLCGIASAMVSRVLIEYIQDRYLYRGTDREPKVGRGVGPSIGLFLLA

VGVTFFFNHMFYNVKMVGAQARAALVAVIYSKSTRLSAKGRAQYTTGKIT

NLAAIDAHRVDLSCESFHYITIFLPVVGCAIAVLVVNLKVAALVGIATMI

VLIFVVAGITIFSMKLRAIIVKLTDKRVTYIREALQSIRIIKYYGWEVPY

CDKIKKVRLDETRNYAKMGSIRGTAIGMFQALPILAGALSFITYAALGHG

TDPARMFSSLTLFNLLLPALAVLPQALQAAGDARVALRRIQRFLGAEEST

PTTVFDATLESTDDAVIVEDASFIWPEVVDDKSDKEKAKDAKKEEKDKKK

AEKKAKKAAKKAAKEIAVVVEEEVEHEKTEGSSESEKGTLKSTFKGFNNL

SFKIKRGEFVVVTGPIGSGKSSLLAAITGSMVLTGGSVRVSSTEWIGCLE

PWIQNATVRDNIVFGRKFDSEWYRTVVTACQLSQDLKIMTHGDNTMIGER
```

```
-continued
GITVSGGQKARINLARAIYGNPEILIMDDVLSAVDARVGAGIVDDCLRGL

AKNSTRILATHQLSVLPKADHVIFMDAEGQFHIGTYQELEADNEQFKALL

AAGSMSKEEVVAVDETEVVIEGDLEDDCDNKEEYEDAAETISILADATQE

LQKVTTTVSAFEENDNMMEEEERMRDAVGLHVYWQYFRQANPSRVKVMMF

IGMIFISMIVIAFLFVFTSVWLSFWTGDRFHASRNFYTGIYIMLGILLLL

AVAGYMIVNEINSAMAARNLHNHALDSVFAARTSFFDTTPQGRIINRFTR

DTDSLDNELAMRLTMLFFGVSAFFSNFLLTCVYVPYVTLVLVPVGFVFYV

SLGYYRKSAREVKRIDSIERSHMMSVFNESISGMPVIIMYKAQHRLMNKL

QATLDDMDSAYFLTAANQRWLSLRLDGLGSLVVLVATILVAVGVFDLTPS

NMGLIISAASFIPEVMSMVAQAVAELENCMNATERILYYKDNIPAEAARE

VDGTELDQRPNWPEQGAISFNNVSMKYRDGLPYVLKSLSVDFQGGHKVGI

CGRTGAGKSTILQTLYRIVELAEGSITIDGVDISTIGLHQLRSQLSIIPQ

EPVLFLGTIRSNLDPLEQYSDAELWGSLRRSGLLDEGETEGKFHLDQKVE

ADGSNFSLGERQLLTLARALLRNTKILVLDEATSNVDYKTDKLVQETISR

EFGHCTILCIAHRLRTIAKYDRILVLESGEINQYDTPWNLYNDKEGIFRG

MCDTSGLNEVDFNK.
```

A polypeptide, typically having steviol glycoside transport mediating activity, may comprise an amino acid sequence having at least about 50%, at least about 55%, at least about 60%, at least about 65%, at least about 70%, at least about 75%, at least about 80%, at least about 85%, at least about, 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity to SEQ ID NO: 29.

A polypeptide, typically having steviol glycoside transport mediating activity, encoded by a recombinant nucleic acid present in a recombinant host of the invention may comprise an amino acid sequence which is a fragment of an amino acid sequence described herein, for example a truncated version of such an amino acid sequence.

That is to say, the invention also a recombinant host overexpressing a biologically active fragment of a polypeptide having steviol glycoside transport mediating activity as described herein. Biologically active fragments of a polypeptide of the invention include polypeptides comprising amino acid sequences sufficiently identical to or derived from the amino acid sequence of SEQ ID NO: 29 which include fewer amino acids than the full-length polypeptide as given in SEQ ID NO: 29, but which exhibit at least one biological activity of the corresponding full-length polypeptide.

Typically, biologically active fragments comprise a domain or motif with at least one activity of the polypeptide of the invention. A biologically active fragment of a polypeptide of the invention can be a polypeptide which is, for example, about 10, about 25, about 50, about 100 or more amino acids in length or at least about 100 amino acids, at least 150, 200, 250, 300, 350, 400, 600, 1000 amino acids in length, or of a length up to the total number of amino acids of the polypeptide of the invention. Moreover, other biologically active portions, in which other regions of the polypeptide are deleted, can be prepared by recombinant techniques and evaluated for one or more of the biological activities of the native form of a polypeptide of the invention. The invention also features nucleic acid fragments which encode the above biologically active fragments of the polypeptide of the invention.

A recombinant host of the invention may overexpress or be deficient in such a polypeptide.

A recombinant host of the invention may comprise recombinant nucleic acid sequences encoding more than one such polypeptide, for example two, three, four or more such polypeptides. The polypeptides thus encoded may be the same or different.

A recombinant cell of the invention may be modified so as to reduce the expression level of more than one such polypeptide, for example two, three, four or more such polypeptides.

An overexpressed polypeptide encoded by a recombinant nucleic acid present in a recombinant host may be one which is obtainable from or derived from or found in an organism of the genus *Yarrowia*, for example one which is obtainable from or derived from or found in a *Yarrowia lipolytica*.

As used herein, the term "polypeptide" refers to a molecule comprising amino acid residues linked by peptide bonds and containing more than five amino acid residues. The amino acids are identified by either the single-letter or three-letter designations. The term "protein" as used herein is synonymous with the term "polypeptide" and may also refer to two or more polypeptides. Thus, the terms "protein", "peptide" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity may be referred to as enzymes. It will be understood that, as a result of the degeneracy of the genetic code, a multitude of nucleotide sequences encoding a given polypeptide may be produced.

A polypeptide encoded by a recombinant nucleic acid for use in a recombinant host of the invention may comprise a signal peptide and/or a propeptide sequence. In the event that a polypeptide of the invention comprises a signal peptide and/or a propeptide, sequence identity may be calculated over the mature polypeptide sequence.

A recombinant nucleic acid sequence for use in a recombinant host of the invention may be provided in the form of a nucleic acid construct. The term "nucleic acid construct" refers to a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

A recombinant nucleic acid sequence for use in a recombinant host of the invention may be provided in the form of an expression vector, wherein the polynucleotide sequence is operably linked to at least one control sequence for the expression of the polynucleotide sequence in a recombinant host cell.

The term "operably linked" as used herein refers to two or more nucleic acid sequence elements that are physically linked and are in a functional relationship with each other. For instance, a promoter is operably linked to a coding sequence if the promoter is able to initiate or regulate the transcription or expression of a coding sequence, in which case the coding sequence should be understood as being "under the control of" the promoter. Generally, when two nucleic acid sequences are operably linked, they will be in the same orientation and usually also in the same reading frame. They usually will be essentially contiguous, although this may not be required.

An expression vector comprises a polynucleotide coding for a polypeptide as described herein, operably linked to the appropriate control sequences (such as a promoter, and transcriptional and translational stop signals) for expression and/or translation in vitro, or in the host cell of the polynucleotide.

The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e., a vector, which exists as an extra-chromosomal entity, the replication of which is independent of chromosomal replication, e.g., a plasmid, an extra-chromosomal element, a mini-chromosome, or an artificial chromosome.

Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. A vector may comprise one or more selectable markers, which permit easy selection of transformed cells.

A recombinant host capable of producing a steviol glycoside which has been modified, preferably in its genome, to result in a deficiency in the production of a polypeptide described herein may be generated according to methods well known to those skilled in the art. A sequence encoding a polypeptide as described herein may be modified such that less or no expression of the polypeptide takes place. A sequence encoding a polypeptide as described herein may be partially or entirely deleted, for example.

A recombinant host of the invention may comprise any polypeptide as described herein. A recombinant host of the invention may overexpress or be deficient in any polypeptide described herein. Typically, a recombinant host of the invention is capable of producing a steviol glycoside. For example, a recombinant host of the invention may be capable of producing one or more of, for example, steviol-13-monoside, steviol-19-monoside, 13-[(β-D-Glucopyranosyl)oxy]kaur-16-en-18-oic acid 2-O-β-D-glucopyranosyl-β-D-glucopyranosyl ester, rubusoside, stevioside, steviol-19-diside, steviolbioside, rebA, rebE, rebD or rebM.

A recombinant host of the invention may comprise one or more recombinant nucleic acid sequences encoding one or more polypeptides having UDP-glycosyltransferase (UGT) activity.

For the purposes of this invention, a polypeptide having UGT activity is one which has glycosyltransferase activity (EC 2.4), i.e. that can act as a catalyst for the transfer of a monosaccharide unit from an activated nucleotide sugar (also known as the "glycosyl donor") to a glycosyl acceptor molecule, usually an alcohol. The glycosyl donor for a UGT is typically the nucleotide sugar uridine diphosphate glucose (uracil-diphosphate glucose, UDP-glucose).

Figure 21:
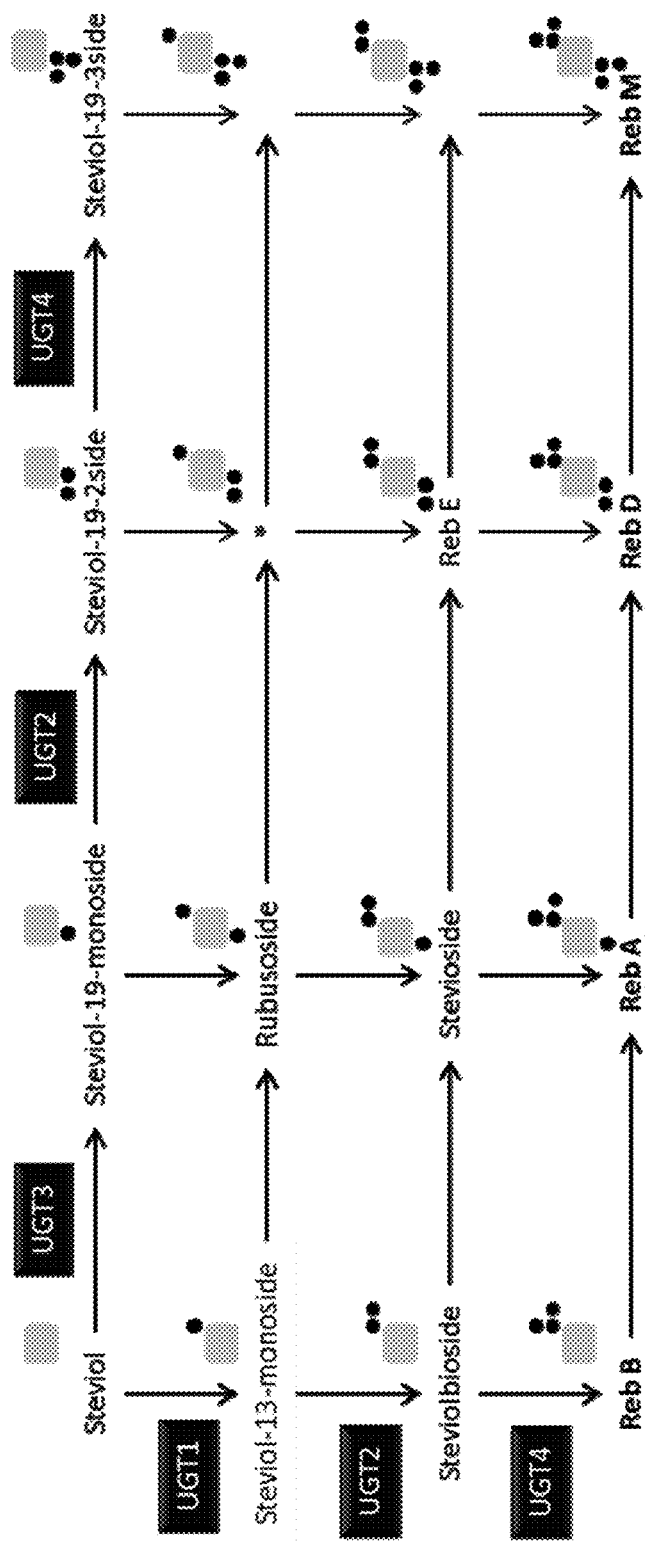
FIG. 21 sets out a schematic diagram of the potential pathways leading to biosynthesis of steviol glycosides. The compound shown with an asterisk is 13-[(β-D-Glucopyranosyl)oxy]kaur-16-en-18-oic acid 2-O-β-D-glucopyranosyl-β-D-glucopyranosyl ester.

Such additional UGTs may be selected so as to produce a desired steviol glycoside. Schematic diagrams of steviol glycoside formation are set out in Humphrey et al., Plant Molecular Biology (2006) 61: 47-62 and Mohamed et al., J. Plant Physiology 168 (2011) 1136-1141. In addition, FIG. 21 sets out a schematic diagram of steviol glycoside formation.

A recombinant host of the invention may thus comprise one or more recombinant nucleic acid sequences encoding one or more of:

(i) a polypeptide having UGT74G1 activity;
(ii) a polypeptide having UGT2 activity;
(iii) a polypeptide having UGT85C2 activity; and
(iv) a polypeptide having UGT76G1 activity.

A recombinant yeast suitable for use in the invention may comprise a nucleotide sequence encoding a polypeptide capable of catalyzing the addition of a C-13-glucose to steviol. That is to say, a recombinant yeast suitable for use in a method of the invention may comprise a UGT which is capable of catalyzing a reaction in which steviol is converted to steviolmonoside.

Such a recombinant yeast suitable for use in a method of the invention may comprise a nucleotide sequence encoding a polypeptide having the activity shown by UDP-glycosyltransferase (UGT) UGT85C2, whereby the nucleotide sequence upon transformation of the yeast confers on that yeast the ability to convert steviol to steviolmonoside.

UGT85C2 activity is transfer of a glucose unit to the 13-OH of steviol. Thus, a suitable UGT85C2 may function as a uridine 5'-diphospho glucosyl: steviol 13-OH transferase, and a uridine 5'-diphospho glucosyl: steviol-19-0-glucoside 13-OH transferase. A functional UGT85C2 polypeptides may also catalyze glucosyl transferase reactions that utilize steviol glycoside substrates other than steviol and steviol-19-O-glucoside. Such sequences may be referred to as UGT1 sequences herein.

A recombinant yeast suitable for use in the invention may comprise a nucleotide sequence encoding a polypeptide which has UGT2 activity.

A polypeptide having UGT2 activity is one which functions as a uridine 5'-diphospho glucosyl: steviol-13-O-glucoside transferase (also referred to as a steviol-13-monoglucoside 1,2-glucosylase), transferring a glucose moiety to the C-2' of the 13-0-glucose of the acceptor molecule, steviol-13-O-glucoside. Typically, a suitable UGT2 polypeptide also functions as a uridine 5'-diphospho glucosyl: rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-O-glucoside and rubusoside, e.g., functional UGT2 polypeptides may utilize stevioside as a substrate, transferring a glucose moiety to the C-2' of the 19-O-glucose residue to produce rebaudioside E. A functional UGT2 polypeptides may also utilize rebaudioside A as a substrate, transferring a glucose moiety to the C-2' of the 19-O-glucose residue to produce rebaudioside D. However, a functional UGT2 polypeptide may be one which does not transfer a glucose moiety to steviol compounds having a 1,3-bound glucose at the C-13 position, i.e., transfer of a glucose moiety to steviol 1,3-bioside and 1,3-stevioside typically does not occur.

A polypeptide having UGT2 activity may also transfer sugar moieties from donors other than uridine diphosphate glucose. For example, a polypeptide having UGT2 activity act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a polypeptide having UGT2 activity may act as a uridine 5'-diphospho L-rhamnosyl:

steviol-13-O-glucoside transferase, transferring a rhamnose moiety to the C-2' of the 13-O-glucose of the acceptor molecule, steviol.

A recombinant yeast suitable for use in the method of the invention may comprise a nucleotide sequence encoding a polypeptide having UGT activity may comprise a nucleotide sequence encoding a polypeptide capable of catalyzing the addition of a C-19-glucose to steviolbioside. That is to say, a recombinant yeast of the invention may comprise a UGT which is capable of catalyzing a reaction in which steviolbioside is converted to stevioside. Accordingly, such a recombinant yeast may be capable of converting steviolbioside to stevioside. Expression of such a nucleotide sequence may confer on the recombinant yeast the ability to produce at least stevioside.

A recombinant yeast suitable for use in a method of the invention may thus also comprise a nucleotide sequence encoding a polypeptide having the activity shown by UDP-glycosyltransferase (UGT) UGT74G1, whereby the nucleotide sequence upon transformation of the yeast confers on the cell the ability to convert steviolbioside to stevioside.

Suitable UGT74G1 polypeptides may be capable of transferring a glucose unit to the 13-OH and/or the 19-COOH of steviol. A suitable UGT74G1 polypeptide may function as a uridine 5'-diphospho glucosyl: steviol 19-COOH transferase and/or a uridine 5'-diphospho glucosyl: steviol-13-0-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose. Such sequences may be referred to herein as UGT3 sequences.

A recombinant yeast suitable for use in a method the invention may comprise a nucleotide sequence encoding a polypeptide capable of catalyzing glucosylation of the C-3' of the glucose at the C-13 position of stevioside. That is to say, a recombinant yeast suitable for use in a method of the invention may comprise a UGT which is capable of catalyzing a reaction in which stevioside is converted to rebaudioside A. Accordingly, such a recombinant yeast may be capable of converting stevioside to rebaudioside A. Expression of such a nucleotide sequence may confer on the yeast the ability to produce at least rebaudioside A.

cosyl: steviol-19-0-glucose, 13-0-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. Such sequences may be referred to herein as UGT4 sequences. A UGT4 may alternatively or in addition be capable of converting RebD to RebM.

A recombinant yeast suitable for use in a method of the invention typically comprises nucleotide sequences encoding at least one polypeptide having UGT1 activity, at least one polypeptide having UGT2 activity, least one polypeptide having UGT3 activity and at least one polypeptide having UGT4 activity. One or more of these nucleic acid sequences may be recombinant. A given nucleic acid may encode a polypeptide having one or more of the above activities. For example, a nucleic acid encode for a polypeptide which has two, three or four of the activities set out above. Preferably, a recombinant yeast for use in the method of the invention comprises UGT1, UGT2 and UGT3 and UGT4 activity. Suitable UGT1, UGT2, UGT3 and UGT4 sequences are described in Table 1 of WO2015/007748.

A recombinant host of the invention may comprise two or more nucleic acid sequences encoding a polypeptide having any one UGT activity, for example UGT1, 2, 3 or 4, activity. Where a recombinant host of the invention comprises two or more nucleic acid sequence encoding a polypeptide having any one UGT activity, those nucleic acid sequences may be the same or different and/or may encode the same or different polypeptides. In particular, a recombinant host of the invention may comprise a nucleic acid sequence encoding a two different UGT2 polypeptides.

A recombinant host according to the invention may comprise one or more recombinant nucleotide sequence(s) encoding one of more of:
  a polypeptide having ent-copalyl pyrophosphate synthase activity;
  a polypeptide having ent-Kaurene synthase activity;
  a polypeptide having ent-Kaurene oxidase activity; and
  a polypeptide having kaurenoic acid 13-hydroxylase activity.

For the purposes of this invention, a polypeptide having ent-copalyl pyrophosphate synthase (EC 5.5.1.13) is capable of catalyzing the chemical reaction:

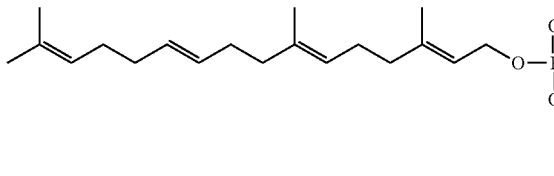 ⇌ 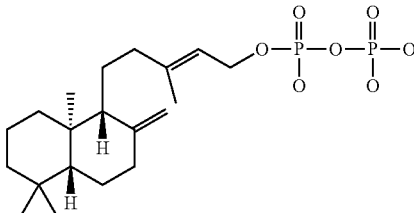

A recombinant yeast suitable for use in a method of the invention may thus also comprise a nucleotide sequence encoding a polypeptide having the activity shown by UDP-glycosyltransferase (UGT) UGT76G1, whereby the nucleotide sequence upon transformation of a yeast confers on that yeast the ability to convert stevioside to rebaudioside A.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-0-1,2 glucoside C-3 ' glucosyl transferase and a uridine 5'-diphospho glu- This enzyme has one substrate, geranylgeranyl pyrophosphate, and one product, ent-copalyl pyrophosphate. This enzyme participates in gibberellin biosynthesis. This enzyme belongs to the family of isomerase, specifically the class of intramolecular lyases. The systematic name of this enzyme class is ent-copalyl-diphosphate lyase (decyclizing). Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this invention, a polypeptide having ent-kaurene synthase activity (EC 4.2.3.19) is a polypeptide that is capable of catalyzing the chemical reaction:

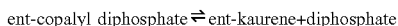

Hence, this enzyme has one substrate, ent-copalyl diphosphate, and two products, ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase, and (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Accordingly, a single nucleotide sequence used in a recombinant host of the invention may encode a polypeptide having ent-copalyl pyrophosphate synthase activity and ent-kaurene synthase activity. Alternatively, the two activities may be encoded two distinct, separate nucleotide sequences.

For the purposes of this invention, a polypeptide having ent-kaurene oxidase activity (EC 1.14.13.78) is a polypeptide which is capable of catalysing three successive oxidations of the 4-methyl group of ent-kaurene to give kaurenoic acid. Such activity typically requires the presence of a cytochrome P450.

Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

For the purposes of the invention, a polypeptide having kaurenoic acid 13-hydroxylase activity (EC 1.14.13) is one which is capable of catalyzing the formation of steviol (ent-kaur-16-en-13-ol-19-oic acid) using NADPH and O2. Such activity may also be referred to as ent-ka 13-hydroxylase activity.

Suitable nucleic acid sequences encoding a kaurenoic acid 13-hydroxylase may for instance comprise a sequence as set out in SEQ ID. NO: 27, 29, 31, 33, 69, 89, 91, 93, 95, 97, 146, 164, 165, 166, 167 or 185 of WO2015/007748.

A recombinant host of the invention may comprise a recombinant nucleic acid sequence encoding a polypeptide having NADPH-cytochrome p450 reductase activity. That is to say, a recombinant host of the invention may be capable of expressing a nucleotide sequence encoding a polypeptide having NADPH-cytochrome p450 reductase activity. For the purposes of the invention, a polypeptide having NADPH-Cytochrome P450 reductase activity (EC 1.6.2.4; also known as NADPH:ferrihemoprotein oxidoreductase, NADPH:hemoprotein oxidoreductase, NADPH:P450 oxidoreductase, P450 reductase, POR, CPR, CYPOR) is typically one which is a membrane-bound enzyme allowing electron transfer to cytochrome P450 in the microsome of the eukaryotic cell from a FAD- and FMN-containing enzyme NADPH:cytochrome P450 reductase (POR; EC 1.6.2.4).

In a recombinant host of the invention, the ability of the host to produce geranylgeranyl diphosphate (GGPP) may be upregulated. Upregulated in the context of this invention implies that the recombinant host produces more GGPP than an equivalent non-recombinant host.

Accordingly, a recombinant host of the invention may comprise one or more nucleotide sequence(s) encoding hydroxymethylglutaryl-CoA reductase, farnesyl-pyrophosphate synthetase and geranylgeranyl diphosphate synthase, whereby the nucleotide sequence(s) upon transformation of a host confer(s) on that host the ability to produce elevated levels of GGPP. Thus, a recombinant host according to the invention may comprise one or more recombinant nucleic acid sequence(s) encoding one or more of hydroxymethyl-glutaryl-CoA reductase, farnesyl-pyrophosphate synthetase and geranylgeranyl diphosphate synthase.

Accordingly, a recombinant host of the invention may comprise nucleic acid sequences encoding one or more of:
a polypeptide having hydroxymethylglutaryl-CoA reductase activity;
a polypeptide having farnesyl-pyrophosphate synthetase activity; and A recombinant host of the invention may be, for example, an multicellular organism or a cell thereof or a unicellular organism. A host of the invention may be a prokaryotic, archaebacterial or eukaryotic host cell.

A prokaryotic host cell may, but is not limited to, a bacterial host cell. An eukaryotic host cell may be, but is not limited to, a yeast, a fungus, an amoeba, an algae, an animal, an insect host cell.

An eukaryotic host cell may be a fungal host cell. "Fungi" include all species of the subdivision *Eumycotina* (Alexopoulos, C. J., 1962, In: Introductory Mycology, John Wiley & Sons, Inc., New York). The term fungus thus includes among others filamentous fungi and yeast.

"Filamentous fungi" are herein defined as eukaryotic microorganisms that include all filamentous forms of the subdivision *Eumycotina* and *Oomycota* (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus, Rhizopus, Schizophyllum, Sordaria, Talaromyces, Rasmsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*. Reference host cells for the comparison of fermentation characteristics of transformed and untransformed cells, include e.g. *Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355),

*P. chrysogenum* CBS 455.95, *Penicillium citrinum* ATCC 38065, *Penicillium chrysogenum* P2, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains. Particularly preferred as filamentous fungal host cell are *Aspergillus niger* CBS 513.88 and derivatives thereof.

An eukaryotic host cell may be a yeast cell. Preferred yeast host cells may be selected from the genera: *Saccharomyces* (e.g., *S. cerevisiae, S. bayanus, S. pastorianus, S. carlsbergensis*), *Brettanomyces, Kluyveromyces, Candida* (e.g., *C. krusei, C. revkaufi, C. pulcherrima, C. tropicalis, C. utilis*), *Issatchenkia* (eg. *I. orientalis*) *Pichia* (e.g., *P. pastoris* and *P. kudriavzevii*), *Schizosaccharomyces, Hansenula, Kloeckera, Pachysolen, Schwanniomyces, Trichosporon, Yarrowia* (e.g., *Y. lipolytica* (formerly classified as *Candida lipolytica*)), *Yamadazyma*.

Prokaryotic host cells may be bacterial host cells. Bacterial host cell may be Gram negative or Gram positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus*), *Acinetobacter, Nocardia, Xanthobacter, Escherichia* (e.g., *E. coli* (e.g., strains DH 1 OB, Stbl2, DH5-alpha, DB3, DB3.1), DB4, DB5, JDP682 and ccdA-over (e.g., U.S. application Ser. No. 09/518, 188))), *Streptomyces, Erwinia, Klebsiella, Serratia* (e.g., *S. marcessans*), *Pseudomonas* (e.g., *P. aeruginosa*), *Salmonella* (e.g., *S. typhimurium, S. typhi*). Bacteria also include, but are not limited to, photosynthetic bacteria (e.g., green non-sulfur bacteria (e.g., *Choroflexus* bacteria (e.g., *C. aurantiacus*), *Chloronema* (e.g., *C. gigateum*)), green sulfur bacteria (e.g., *Chlorobium* bacteria (e.g., *C. limicola*), *Pelodictyon* (e.g., *P. luteolum*), purple sulfur bacteria (e.g., *Chromatium* (e.g., *C. okenii*)), and purple non-sulfur bacteria (e.g., *Rhodospirillum* (e.g., *R. rubrum*), *Rhodobacter* (e.g. *R. sphaeroides, R. capsulatus*), and *Rhodomicrobium* bacteria (e.g., *R. vanellii*)).

Host Cells may be host cells from non-microbial organisms. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

A recombinant host according to the present invention may be able to grow on any suitable carbon source known in the art and convert it to a steviol glycoside. The recombinant host may be able to convert directly plant biomass, celluloses, hemicelluloses, pectines, rhamnose, galactose, fucose, maltose, maltodextrines, ribose, ribulose, or starch, starch derivatives, sucrose, lactose and glycerol. Hence, a preferred host expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the host is able to convert a carbon source selected from the group consisting of glucose, xylose, arabinose, sucrose, lactose and glycerol. The host cell may for instance be a eukaryotic host cell as described in WO03/062430, WO06/009434, EP149970861, WO2006096130 or WO04/099381.

Thus, in a further aspect, the invention also provides a process for the preparation of a steviol glycoside which comprises fermenting a recombinant host of the invention which is capable of producing at least one steviol glycoside in a suitable fermentation medium, and optionally recovering the steviol glycoside.

The fermentation medium used in the process for the production of a steviol glycoside may be any suitable fermentation medium which allows growth of a particular eukaryotic host cell. The essential elements of the fermentation medium are known to the person skilled in the art and may be adapted to the host cell selected.

Preferably, the fermentation medium comprises a carbon source selected from the group consisting of plant biomass, celluloses, hemicelluloses, pectines, rhamnose, galactose, fucose, fructose, maltose, maltodextrines, ribose, ribulose, or starch, starch derivatives, sucrose, lactose, fatty acids, triglycerides and glycerol. Preferably, the fermentation medium also comprises a nitrogen source such as ureum, or an ammonium salt such as ammonium sulphate, ammonium chloride, ammoniumnitrate or ammonium phosphate.

The fermentation process according to the present invention may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. A SSF process may be particularly attractive if starch, cellulose, hemicelluose or pectin is used as a carbon source in the fermentation process, where it may be necessary to add hydrolytic enzymes, such as cellulases, hemicellulases or pectinases to hydrolyse the substrate.

The recombinant host used in the process for the preparation of a steviol glycoside may be any suitable recombinant host as defined herein above. It may be advantageous to use a recombinant eukaryotic recombinant host according to the invention in the process since most eukaryotic cells do not require sterile conditions for propagation and are insensitive to bacteriophage infections. In addition, eukaryotic host cells may be grown at low pH to prevent bacterial contamination.

The recombinant host according to the present invention may be a facultative anaerobic microorganism. A facultative anaerobic recombinant host can be propagated aerobically to a high cell concentration. This anaerobic phase can then be carried out at high cell density which reduces the fermentation volume required substantially, and may minimize the risk of contamination with aerobic microorganisms.

The fermentation process for the production of a steviol glycoside according to the present invention may be an aerobic or an anaerobic fermentation process.

An anaerobic fermentation process may be herein defined as a fermentation process run in the absence of oxygen or in which substantially no oxygen is consumed, preferably less than 5, 2.5 or 1 mmol/L/h, and wherein organic molecules serve as both electron donor and electron acceptors. The fermentation process according to the present invention may also first be run under aerobic conditions and subsequently under anaerobic conditions.

The fermentation process may also be run under oxygen-limited, or micro-aerobical, conditions. Alternatively, the fermentation process may first be run under aerobic conditions and subsequently under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used.

The production of a steviol glycoside in the process according to the present invention may occur during the growth phase of the host cell, during the stationary (steady state) phase or during both phases. It may be possible to run the fermentation process at different temperatures.

The process for the production of a steviol glycoside may be run at a temperature which is optimal for the recombinant host. The optimum growth temperature may differ for each transformed recombinant host and is known to the person skilled in the art. The optimum temperature might be higher than optimal for wild type organisms to grow the organism efficiently under non-sterile conditions under minimal infection sensitivity and lowest cooling cost.

Alternatively, the process may be carried out at a temperature which is not optimal for growth of the recombinant host.

The process for the production of a steviol glycoside according to the present invention may be carried out at any suitable pH value. If the recombinant host is a yeast, the pH in the fermentation medium preferably has a value of below 6, preferably below 5.5, preferably below 5, preferably below 4.5, preferably below 4, preferably below pH 3.5 or below pH 3.0, or below pH 2.5, preferably above pH 2. An advantage of carrying out the fermentation at these low pH values is that growth of contaminant bacteria in the fermentation medium may be prevented.

Such a process may be carried out on an industrial scale. The product of such a process is one or more steviol glycosides.

Recovery of steivol glycoside(s) from the fermentation medium may be performed by known methods in the art, for instance by distillation, vacuum extraction, solvent extraction, or evaporation.

In the process for the production of a steviol glycoside according to the invention, it may be possible to achieve a concentration of above 5 mg/l fermentation broth, preferably above 10 mg/l, preferably above 20 mg/l, preferably above 30 mg/l fermentation broth, preferably above 40 mg/l, more preferably above 50 mg/l, preferably above 60 mg/l, preferably above 70, preferably above 80 mg/l, preferably above 100 mg/l, preferably above 1 g/l, preferably above 5 g/l, preferably above 10 g/l, for example at least about 15 g/L, such as at least about 20 g/l. The invention further provides a fermentation broth comprising a steviol glycoside obtainable by the process of the invention for the preparation of a steivol glycoside.

In the event that one or more steviol glycosides is expressed within a recombinant host of the invention, such cells may need to be treated so as to release them. Preferentially, at least one steviol glycoside, for example rebA or rebM, is produced extracellularly The invention also provides a steviol glycoside obtained by a process according to the invention for the preparation of a steviol glycoside or obtainable from a fermentation broth of the invention. Such a steviol glycoside may be a non-naturally occurring steviol glycoside, that is to say one which is not produced in plants.

Also provided is a composition obtainable by a process of the invention (which typically comprises one or more steviol glycosides), Also provided is a composition comprising two or more steviol glycosides obtainable by a process of the invention for the preparation of a steviol glycoside or obtainable from a fermentation broth of the invention. In such a composition, one or more of the steviol glycosides may be a non-naturally occurring steviol glycoside, that is to say one which is not produced in plants. These are all compositions of the invention.

A composition of the invention may be used in any application known for such compounds. In particular, such a composition may for instance be used as a sweetener, for example in a food or a beverage. According to the invention therefore, there is provided a foodstuff, feed or beverage which comprises a composition of the invention.

For example a composition of the invention may be formulated in soft drinks, as a tabletop sweetener, chewing gum, dairy product such as yoghurt (eg. plain yoghurt), cake, cereal or cereal-based food, nutraceutical, pharmaceutical, edible gel, confectionery product, cosmetic, toothpastes or other oral cavity composition, etc. In addition, a composition of the invention can be used as a sweetener not only for drinks, foodstuffs, and other products dedicated for human consumption, but also in animal feed and fodder with improved characteristics.

Accordingly, the invention provides, inter alia, a foodstuff, feed or beverage which comprises a composition of the invention.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

A composition of the invention can be used in dry or liquid forms. It can be added before or after heat treatment of food products. The amount of the sweetener depends on the purpose of usage. It can be added alone or in the combination with other compounds.

A composition of the invention may be blended with one or more further non-caloric or caloric sweeteners. Such blending may be used to improve flavour or temporal profile or stability. A wide range of both non-caloric and caloric sweeteners may be suitable for blending with a composition of the invention. For example, non-caloric sweeteners such as mogroside, monatin, aspartame, acesulfame salts, cyclamate, sucralose, saccharin salts or erythritol. Caloric sweeteners suitable for blending with a steviol glycoside or a composition of the invention include sugar alcohols and carbohydrates such as sucrose, glucose, fructose and HFCS. Sweet tasting amino acids such as glycine, alanine or serine may also be used.

A composition of the invention can be used in the combination with a sweetener suppressor, such as a natural sweetener suppressor. It may be combined with an umami taste enhancer, such as an amino acid or a salt thereof.

A composition of the invention can be combined with a polyol or sugar alcohol, a carbohydrate, a physiologically active substance or functional ingredient (for example a carotenoid, dietary fiber, fatty acid, saponin, antioxidant, nutraceutical, flavonoid, isothiocyanate, phenol, plant sterol or stanol (phytosterols and phytostanols), a polyols, a prebiotic, a probiotic, a phytoestrogen, soy protein, sulfides/thiols, amino acids, a protein, a vitamin, a mineral, and/or a substance classified based on a health benefits, such as cardiovascular, cholesterol-reducing or anti-inflammatory.

A composition of the invention may include a flavoring agent, an aroma component, a nucleotide, an organic acid, an organic acid salt, an inorganic acid, a bitter compound, a protein or protein hydrolyzate, a surfactant, a flavonoid, an astringent compound, a vitamin, a dietary fiber, an antioxidant, a fatty acid and/or a salt.

A composition of the invention may be applied as a high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, a composition of the invention may be used as a sweetener not only for drinks, foodstuffs, and other products dedicated for human consumption, but also in animal feed and fodder with improved characteristics.

The examples of products where a composition of the invention can be used as a sweetening compound can be as alcoholic beverages such as vodka, wine, beer, liquor, sake, etc; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others. In principal it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness. Those of ordinary skill in the art can readily discern the appropriate amount of sweetener to put in the sweetened composition.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions which incorporate a composition of the invention can be made by any method known to those skilled in the art that provide homogenous even or homogeneous mixtures of the ingredients. These methods include dry blending, spray drying, agglomeration, wet granulation, compaction, co-crystallization and the like.

In solid form a composition of the invention can be provided to consumers in any form suitable for delivery into the comestible to be sweetened, including sachets, packets, bulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

A composition of the invention may include various bulking agents, functional ingredients, colorants, flavors.

The terms "sequence homology" or "sequence identity" or "homology" or "identity" are used interchangeably herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison. In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice,P. Longden,I. and Bleasby,A. Trends in Genetics 16, (6) pp276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, word length=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at www.ncbi.nlm.nih.gov.

Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation, genetic modification etc of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265,186.

Embodiments of the Invention

1. A recombinant host capable of producing a steviol glycoside which overexpresses a polypeptide which mediates steviol glycoside transport and which polypeptide comprises the amino acid sequence set forth in SEQ ID NO: 29 or an amino acid sequence having at least about 50% sequence identity thereto.
2. A recombinant host capable of producing a steviol glycoside which has been modified, preferably in its genome, to result in a deficiency in the production of a polypeptide which mediates steviol glycoside transport and which polypeptide comprises the amino acid sequence set forth in SEQ ID NO: 29 or an amino acid sequence having at least about 50% sequence identity thereto.
3. A recombinant host according to claim 1, which comprises a recombinant nucleic acid encoding a polypeptide which comprises the amino acid sequence set forth in SEQ ID NO: 29 or an amino acid sequence having at least about 50% sequence identity thereto.
4. A recombinant host according to any one of the preceding embodiments which comprises one or more recombinant nucleotide sequence(s) encoding:
   a polypeptide having ent-copalyl pyrophosphate synthase activity;
   a polypeptide having ent-Kaurene synthase activity;
   a polypeptide having ent-Kaurene oxidase activity; and
   a polypeptide having kaurenoic acid 13-hydroxylase activity.
5. A recombinant host according to any one of the preceding embodiments, which comprises a recombinant nucleic acid sequence encoding a polypeptide having NADPH-cytochrome p450 reductase activity.
6. A recombinant host according to any one of the preceding embodiments which comprises a recombinant nucleic acid sequence encoding one or more of:
   (i) a polypeptide having UGT74G1 activity;
   (ii) a polypeptide having UGT2 activity;
   (iii) a polypeptide having UGT85C2 activity; and
   (iv) a polypeptide having UGT76G1 activity.
7. A recombinant host according to any one of the preceding embodiments, wherein the host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia*.
8. A recombinant host according to embodiment 7, wherein the recombinant host is a *Saccharomyces cerevisiae* cell, a *Yarrowia lipolytica* cell, a *Candida krusei* cell, an *Issatchenkia orientalis* cell or an *Escherichia coli* cell.
9. A recombinant host according to any one of the preceding embodiments, wherein the ability of the host to produce geranylgeranyl diphosphate (GGPP) is upregulated.
10. A recombinant host according to any one of the preceding embodiments which comprises a nucleic acid sequence encoding one or more of:
    a polypeptide having hydroxymethylglutaryl-CoA reductase activity; or
    a polypeptide having farnesyl-pyrophosphate synthetase activity.
11. A recombinant host capable of producing a steviol glycoside which overexpresses a heterologous polypeptide which mediates steviol glycoside transport.
12. A process for the preparation of a steviol glycoside which comprises fermenting a recombinant host according to any one of the preceding embodiments in a suitable fermentation medium and, optionally, recovering the steviol glycoside.
13. A process according to embodiment 12 for the preparation of a steviol glyocisde, optionally wherein the process is carried out on an industrial scale.
14. A fermentation broth comprising a steviol glycoside obtainable by the process according to embodiment 12 or 13.
15. A steviol glycoside obtained by a process according to embodiment 12 or 13 or obtained from a fermentation broth according to embodiment 14.
16. A composition obtainable by a process according to embodiment 12 or 13, a composition comprising two or more steviol glycosides obtained by a process according to embodiment 12 or 13 or a composition obtained from a fermentation broth according to embodiment 14.
17. A foodstuff, feed or beverage which comprises a steviol glycoside according to claim 15 or a composition according to claim 16.

A reference herein to a patent document or other matter which is given as prior art is not to be taken as an admission that that document or matter was known or that the information it contains was part of the common general knowledge as at the priority date of any of the claims. The disclosure of each reference set forth herein is incorporated herein by reference in its entirety.

The present invention is further illustrated by the following Examples:

EXAMPLES

General

Standard genetic techniques, such as overexpression of enzymes in the host cells, as well as for additional genetic modification of host cells, are known methods in the art, such as described in Sambrook and Russel (2001) "Molecular Cloning: A Laboratory Manual ($3^{rd}$ edition), Cold Spring Harbor Laboratory, *Cold Spring Harbor Laboratory Press*, or F. Ausubel et al, eds., "Current protocols in molecular biology", Green Publishing and Wiley Interscience, New York (1987). Methods for transformation and genetic modification of fungal host cells are known from e.g. EP-A-0 635 574, WO 98/46772, WO 99/60102 and WO 00/37671.

Example 1: Description of Steviol Glycoside Production Strain ML14094 (MAT-A Lineage)

Two *Yarrowia lipolytica* strains of mating types MATA and MATB were engineered for steviol glycoside production. These strains were mated, the diploid sporulated, and spores with steviol glycoside production were selected. One of these spores was further developed for the production of steviol glycosides, including the production of Rebaudioside A.

Step 1: Strain ML10371 (MAT-A, lys1-, ura3-, leu2-) was transformed with 5 defined DNA fragments. All transformations were carried out via a lithium acetate/PEG fungal transformation protocol method and transformants were selected on minimal medium, YPD+100 ug/ml nourseothricin or YPD+100 ug/ml hygromycin, as appropriate.

1) a 7.0 kb DNA fragment isolated by gel purification following HindIII/NotI digestion of plasmid MB6969 (FIG. 1). This construct encodes a synthetic construct for the overexpression of UGT2_1a (SEQ ID NO: 1) linked to the pPGM promoter (SEQ ID NO: 2) and xprT terminator (SEQ ID NO: 9) and the HPH hygromycin resistance gene, together flanked by lox sites (Güldener et al, 1996, Lambert et al, 2007), and a synthetic construct for the overexpression of the codon optimized *Y. lipolytica* hydroxymethylglutaryl-coenzyme A reductase open reading frame lacking the 5' membrane anchor sequence (tHMGopt: SEQ ID NO: 15) linked to the pHSP promoter (SEQ ID NO: 3) and cwpT terminator (SEQ ID NO: 10).

Figure 2:
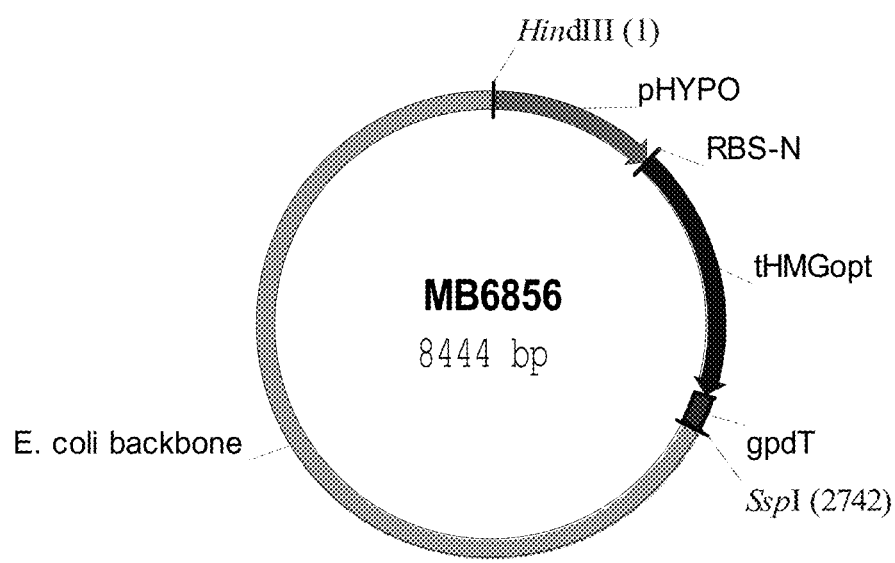
FIG. 2 sets out a schematic representation of the plasmid MB6856, encoding tHMG.

2) a 2.7 kb DNA fragment isolated by gel purification following HindIII/SspI digestion of MB6856 (FIG. 2). This construct encodes tHMGopt (SEQ ID NO: 15) linked to the pHYPO promoter (SEQ ID NO: 4) and gpdT terminator (SEQ ID NO: 11).

Figure 3:
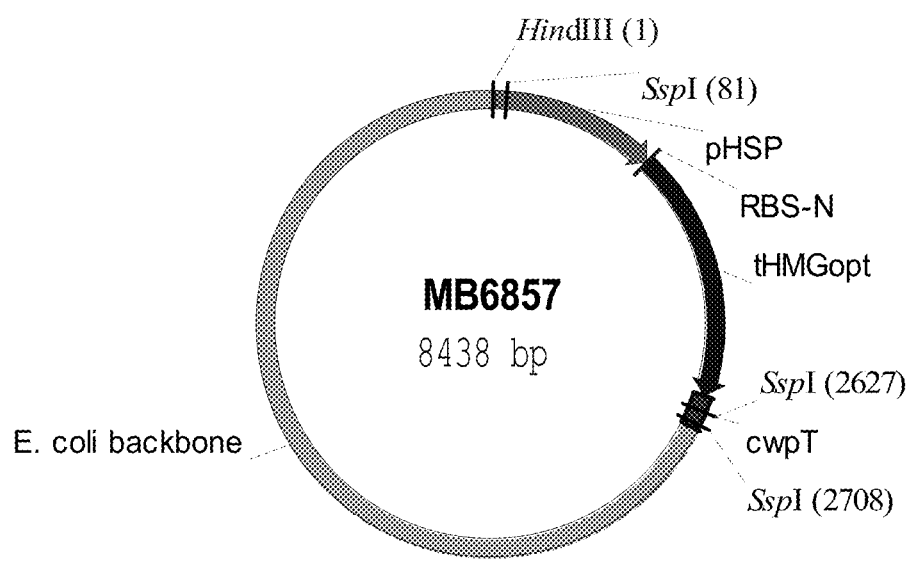
FIG. 3 sets out a schematic representation of the plasmid MB6857, encoding tHMG.

3) a 2.5 kb DNA fragment isolated by gel purification following SspI digestion of MB6857 (FIG. 3). This construct encodes tHMGopt (SEQ ID NO: 15) linked to the pHSP promoter (SEQ ID NO: 3) and cwpT terminator (SEQ ID NO: 10).

Figure 4:
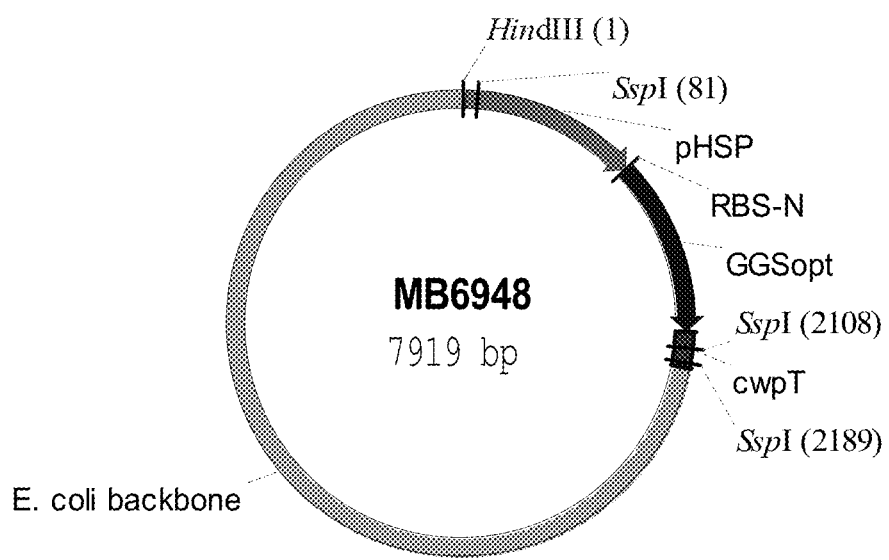
FIG. 4 sets out a schematic representation of the plasmid MB6948, encoding GGS.

4) a 2.0 kb DNA fragment isolated by gel purification following SspI digestion of MB6948 (FIG. 4). This construct encodes a synthetic construct for the overexpression of the codon optimized *Y. lipolytica* geranyl-geranyl-pyrophosphate synthetase (GGSopt: SEQ ID NO: 16) linked to the pHSP promoter (SEQ ID NO: 3) and cwpT terminator (SEQ ID NO: 10).

Figure 5:
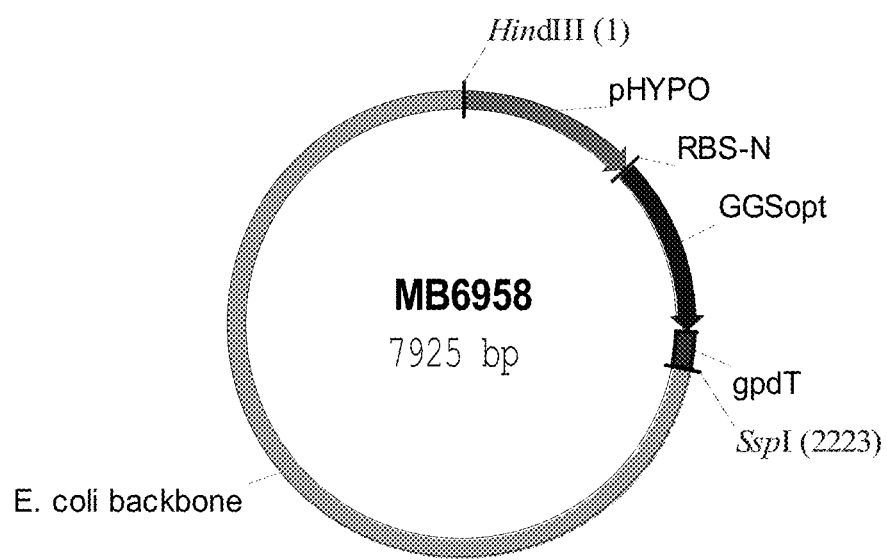
FIG. 5 sets out a schematic representation of the plasmid MB6958, encoding GGS.

5) a 2.2 kb DNA fragment isolated by gel purification following HindIII/SspI digestion of MB6958 (FIG. 5). This construct encodes GGSopt (SEQ ID NO: 16) linked to the pHYPO promoter (SEQ ID NO: 4) and gpdT terminator (SEQ ID NO: 11). The resulting strain was denoted ML13462.

Figure 6:
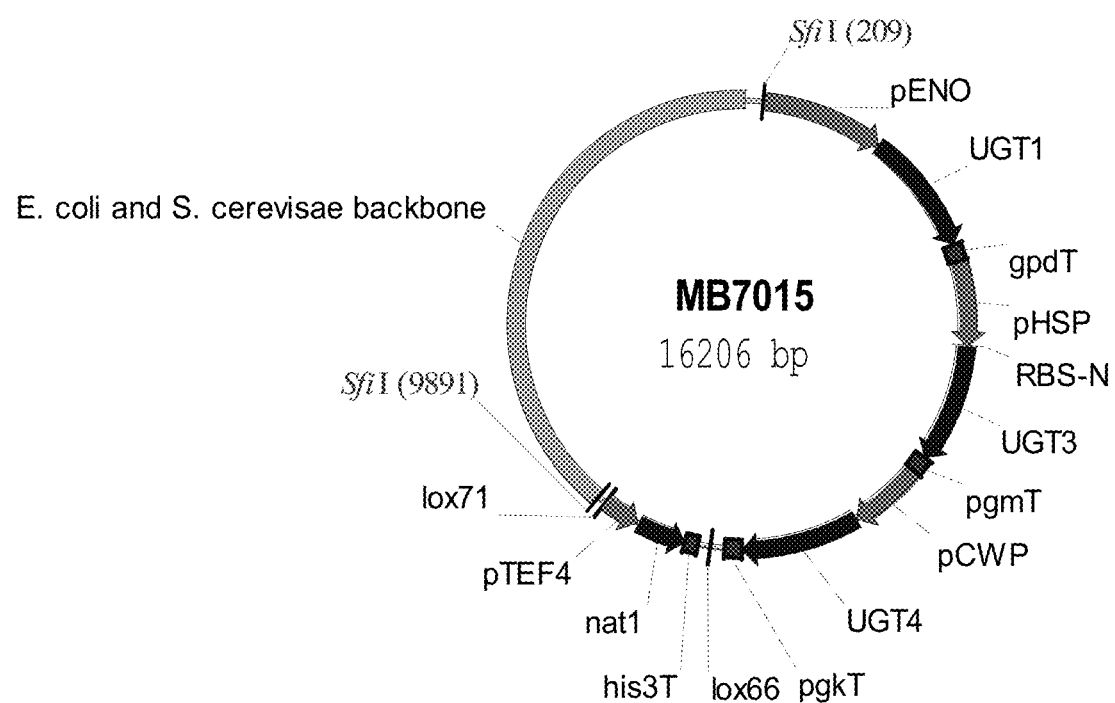
FIG. 6 sets out a schematic representation of the plasmid MB7015, encoding UGT1, UGT3, UGT4, NAT.

Step 2. Strain ML13462 was transformed with a 9.7 kb fragment isolated by gel purification following SfiI digestion of plasmid MB7015 (FIG. 6). This construct encodes a synthetic construct for the overexpression of UGT1 (SEQ ID NO: 17) linked to the pENO (SEQ ID NO: 5) promoter and gpdT terminator (SEQ ID NO: 11), UGT3 (SEQ ID NO: 18) linked to the pHSP promoter (SEQ ID NO: 3) and pgmT terminator (SEQ ID NO: 12), UGT4 (SEQ ID NO: 19) linked to the pCWP (SEQ NO: 6) promoter and pgkT terminator (SEQ ID NO: 13), and the lox-flanked nourseothricin resistance marker (NAT). Note that placement of lox sites allows for subsequent removal of nourseothricin resistance via CRE recombinase mediated recombination. A nourseothricin resistant isolate was denoted ML13500.

Figure 7:
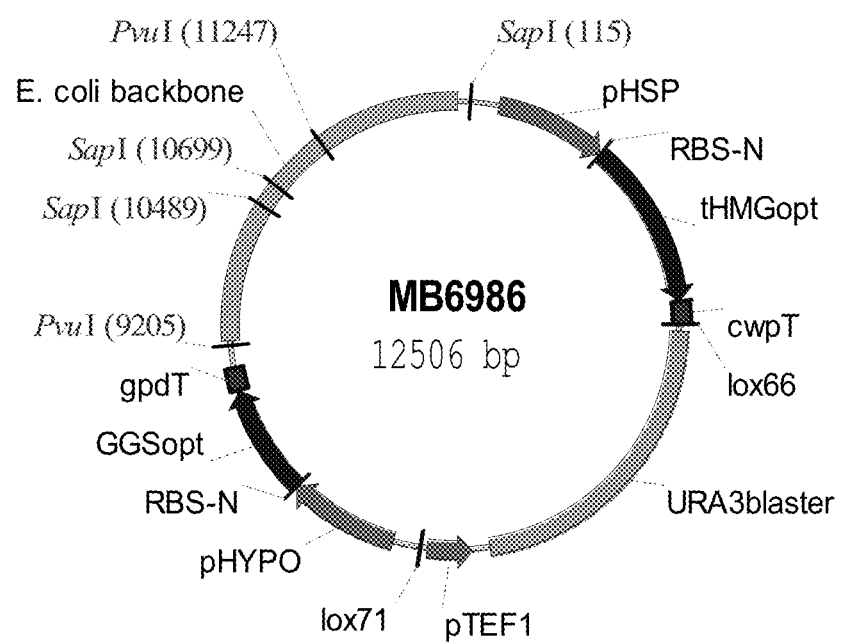
FIG. 7 sets out a schematic representation of the plasmid MB6986, encoding tHMG, URA3, GGS.

Step 3. Strain ML13500 was transformed with a 9.1 kb fragment isolated by gel purification following PvuI/SapI digestion of plasmid MB6986 (FIG. 7). This construct encodes tHMGopt (SEQ ID NO: 15) linked to the pHSP promoter (SEQ ID NO: 3) and cwpT terminator (SEQ ID NO: 10), the lox-flanked URA3blaster prototrophic marker, and GGSopt (SEQ ID NO: 16) linked to the pHYPO promoter (SEQ ID NO: 4) and gpdT terminator (SEQ ID NO: 11). Transformants were selected on minimal medium lacking uracil. One selected uracil prototroph was denoted ML13723.

Figure 8:
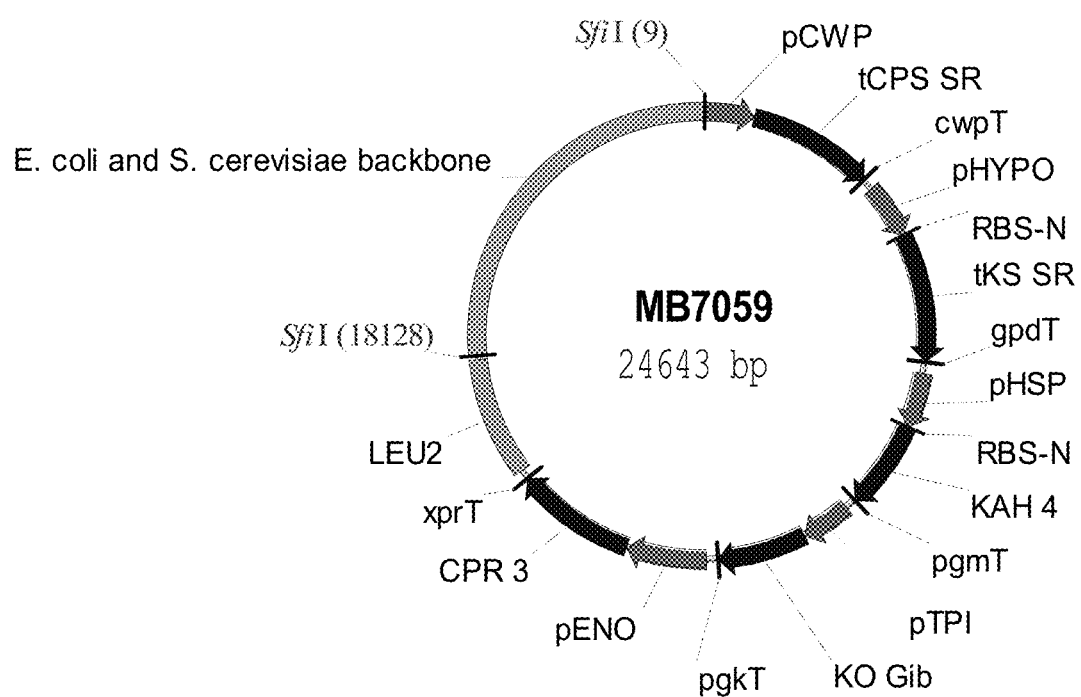
FIG. 8 sets out a schematic representation of the plasmid MB7059, encoding tCPS_SR, tKS_SR, KAH_4, KO_Gib, CPR_3, LEU2.

Step 4. Strain ML13723 was transformed with an 18.1 kb fragment isolated by gel purification following SfiI digestion of plasmid MB7059 (FIG. 8). MB7059 encodes the tCPS_SR (SEQ ID NO: 20) linked to pCWP promoter (SEQ ID NO: 6) and cwpT terminator (SEQ ID NO: 10), the tKS_SR (SEQ ID NO: 21) linked to the pHYPO promoter (SEQ ID NO: 4) and gpdT terminator (SEQ ID NO: 11), the KAH_4 (SEQ ID NO: 22) linked to the pHSP promoter (SEQ ID NO: 3) and pgmT terminator (SEQ ID NO: 12), the KO_Gib (SEQ ID NO: 23) linked to the pTPI promoter (SEQ ID NO: 7) and pgkT terminator (SEQ ID NO: 13), the CPR_3 (SEQ ID NO: 24) linked to the pENO promoter (SEQ ID NO: 5) and xprT terminator (SEQ ID NO: 9) and the native *Y. lipolytica* LEU2 locus. One selected rebaudioside A-producing transformant was denoted ML14032.

Step 5. Strain ML14032 was struck to YPD and grown overnight and then struck to 5-FOA plates to allow for recombination mediated loss of the URA3 marker introduced previously. One selected 5-FOA resistant transformant was denoted ML14093.

Figure 9:
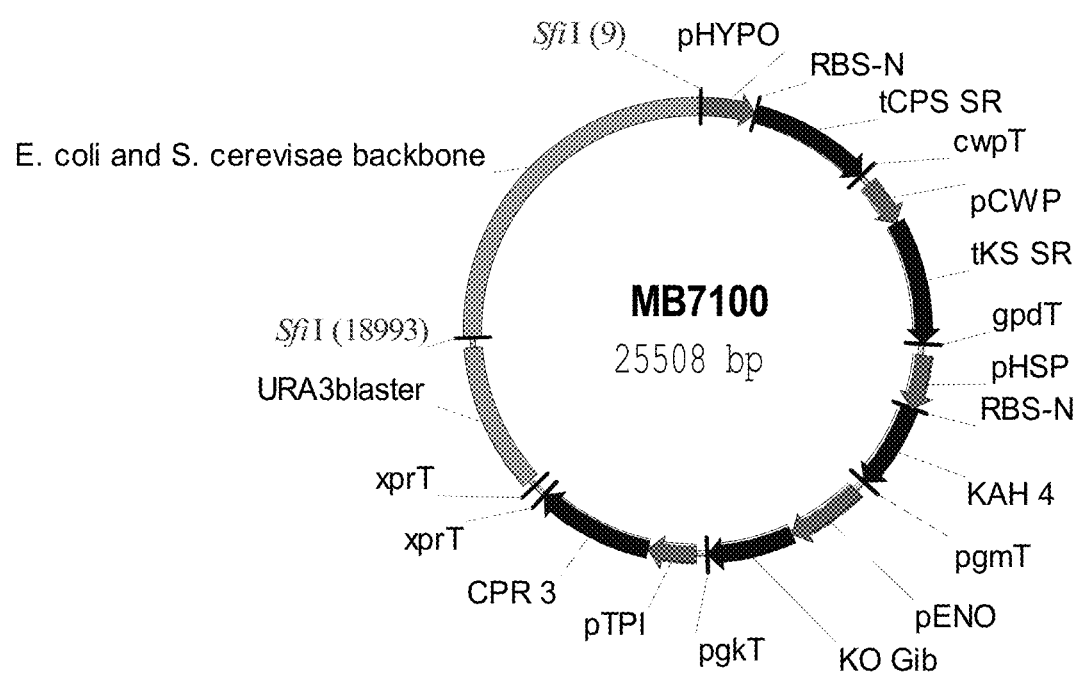
FIG. 9 sets out a schematic representation of the plasmid MB7100, encoding tCPS_SR, tKS_SR, KAH_4, KO_Gib, CPR_3, URA3.

Step 6. Strain ML14093 was transformed with a 19.0 kb fragment isolated by gel purification following SfiI digestion of plasmid MB7100 (FIG. 9). MB7100 encodes the tCPS_SR (SEQ ID NO: 20) linked to the pHYPO promoter (SEQ ID NO: 4) and cwpT terminator (SEQ ID NO: 10), the tKS_SR (SEQ ID NO: 21) linked to the pCWP promoter (SEQ ID NO: 6) and gpdT terminator (SEQ ID NO: 11), the KAH_4 (SEQ ID NO: 22) linked to the pHSP promoter (SEQ ID NO: 3) and pgmT terminator (SEQ ID NO: 12), the KO_Gib (SEQ ID NO: 23) linked to the pENO promoter (SEQ ID NO: 5) and pgkT terminator (SEQ ID NO: 13), the CPR_3 (SEQ ID NO: 24) linked to the pTPI promoter (SEQ ID NO: 7) and xprT terminator (SEQ ID NO: 9) and URA3blaster prototrophic marker. Transformants were selected on minimal medium lacking uracil. One selected rebaudioside A producing uracil prototroph was denoted ML14094.

Example 2. Description of Steviol Glycoside Production Strain ML14087 (MAT-B Lineage)

Step 1. Strain ML13206 (MAT-B, ade1-, ure2-, leu2-) was transformed with 5 defined DNA fragments. All transformations were carried out via a lithium acetate/PEG fungal transformation protocol method and transformants were selected on minimal medium, YPD+100 ug/ml nourseothricin or YPD+100 ug/ml hygromycin, as appropriate.

1) a 7.0 kb DNA fragment isolated by gel purification following HindIII/NotI digestion of plasmid MB6969 (FIG. 1). This construct encodes a synthetic construct for the overexpression of the codon pair optimized (CpO) ORF of UGT2_1a (SEQ ID NO: 1) linked to the pPGM (SEQ ID NO: 2) promoter and xprT terminator (SEQ ID NO: 9) and the HPH hygromycin resistance gene, together flanked by lox sites (Güldener et al, 1996, Lambert et al, 2007), and a synthetic construct for the overexpression of the codon optimized Y. lipolytica hydroxymethylglutaryl-coenzyme A reductase open reading frame lacking the 5' membrane anchor sequence (tHMGopt: SEQ ID NO: 15) linked to the pHSP promoter (SEQ ID NO: 3) and cwpT terminator (SEQ ID NO: 10).

2) a 2.7 kb DNA fragment isolated by gel purification following HindIII/SspI digestion of MB6856 (FIG. 2). This construct encodes tHMGopt (SEQ ID NO: 15) linked to the pHYPO promoter (SEQ ID NO: 4) and gpdT terminator (SEQ ID NO: 11).

3) a 2.5 kb DNA fragment isolated by gel purification following SspI digestion of MB6857 (FIG. 3). This construct encodes tHMGopt (SEQ ID NO: 15) linked to the pHSP promoter (SEQ ID NO: 3) and cwpT terminator (SEQ ID NO: 10).

4) a 2.0 kb DNA fragment isolated by gel purification following SspI digestion of MB6948 (FIG. 4). This construct encodes a synthetic construct for the overexpression of the codon optimized Y. lipolytica geranyl-geranyl-pyrophosphate synthetase (GGSopt: SEQ ID NO: 16) linked to the pHSP promoter (SEQ ID NO: 3) and cwpT terminator (SEQ ID NO: 10).

5) a 2.2 kb DNA fragment isolated by gel purification following HindIII/SspI digestion of MB6958 (FIG. 5). This construct encodes GGSopt (SEQ ID NO: 16) linked to the pHYPO (SEQ ID NO: 4) promoter and gpdT terminator (SEQ ID NO: 11). The resulting strain was denoted ML13465.

Step 2. Strain ML13465 was transformed with 2 defined DNA fragments:

1). a 9.7 kb fragment isolated by gel purification following SfiI digestion of plasmid MB7015 (FIG. 6). This construct encodes a synthetic construct for the overexpression of UGT1 (SEQ ID NO: 17) linked to the pENO promoter (SEQ ID NO: 5) and gpdT (SEQ ID NO: 11) terminator, UGT3 (SEQ ID NO: 18) linked to the pHSP promoter (SEQ ID NO: 3) and pgmT terminator (SEQ ID NO: 12), UGT4 (SEQ ID NO: 19) linked to the pCWP promoter (SEQ ID NO: 6) and pgkT terminator (SEQ ID NO: 13), and the lox-flanked nourseothricin resistance marker (NAT). Note that placement of lox sites allows for subsequent removal of nourseothricin resistance via CRE recombinase mediated recombination.

Figure 10:
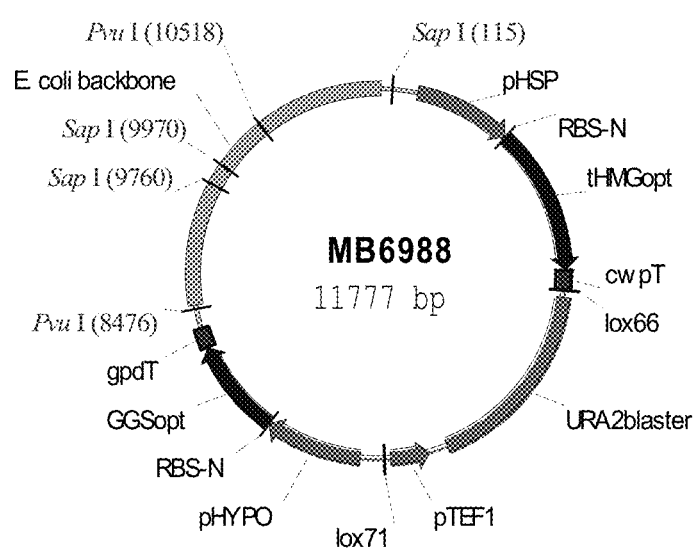
FIG. 10 sets out a schematic representation of the plasmid MB6988, encoding tHMG, URA2, GGS.

2). a 9.1 kb fragment isolated by gel purification following PvuI/SapI digestion of plasmid MB6988 (FIG. 10). This construct encodes tHMGopt (SEQ ID NO: 15) linked to the pHSP promoter (SEQ ID NO: 3) and cwpT terminator (SEQ ID NO: 10), the lox-flanked URA2blaster prototrophic marker, and GGSopt (SEQ ID NO: 16) linked to the pHYPO promoter (SEQ ID NO: 4) and gpdT terminator (SEQ ID NO: 11). Strains were selected on YPD+100 ug/ml nourseothricin and replica plated to minimal medium lacking uracil. A nourseothricin resistant, uracil prototrophic isolate was denoted ML13490

Step 3. Strain ML13490 was struck to YPD and grown overnight and then struck to 5-FOA plates to allow for recombination mediated loss of the URA2 marker introduced previously. One selected 5-FOA resistant transformant was denoted ML13501.

Step 4. Strain ML13501 was transformed with a 9.1 kb fragment isolated by gel purification following PvuI/SapI digestion of plasmid MB6988 (FIG. 10). Transformants were selected on minimal medium lacking uracil. One selected uracil prototroph was denoted ML13724.

Figure 11:
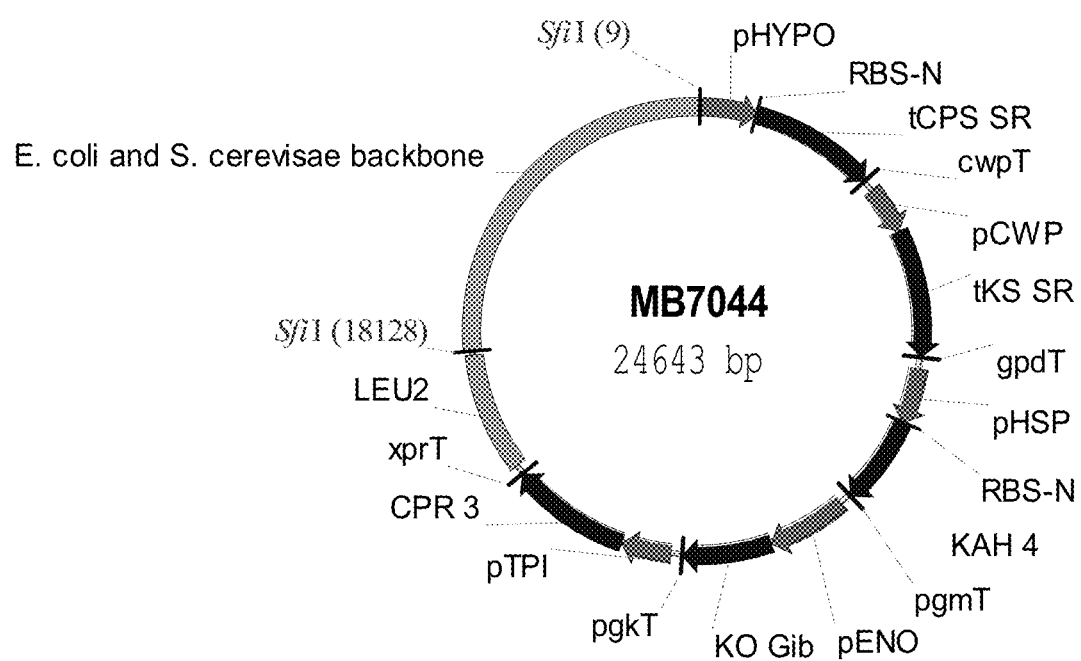
FIG. 11 sets out a schematic representation of the plasmid MB7044, encoding tCPS_SR, tKS_SR, KAH_4, KO_Gib, CPR_3, LEU2.

Step 5. Strain ML13724 was transformed with an 18.1 kb fragment isolated by gel purification following SfiI digestion of plasmid MB7044 (FIG. 11). MB7044 encodes the tCPS_SR (SEQ ID NO: 20) linked to the pHYPO promoter (SEQ ID NO: 4) and cwpT terminator (SEQ ID NO: 10), the tKS_SR (SEQ ID NO: 21) linked to the pCWP promoter (SEQ ID NO: 6) and gpdT terminator (SEQ ID NO: 11), the KAH_4 (SEQ ID NO: 22) linked to the pHSP promoter (SEQ ID NO: 3) and pgmT terminator (SEQ ID NO: 12), the KO_Gib (SEQ ID NO: 23) linked to the pENO promoter (SEQ ID NO: 5) and pgkT terminator (SEQ ID NO: 13), the CPR_3 (SEQ ID NO: 24) linked to the pTPI promoter (SEQ ID NO: 7) and xprT terminator (SEQ ID NO: 9) and the LEU2 locus. One selected rebaudioside A-producing transformant was denoted ML14044.

Step 6. Strain ML14044 was struck to YPD and grown overnight and then struck to 5-FOA plates to allow for recombination mediated loss of the URA2 marker introduced previously. One selected 5'-FOA resistant transformant was denoted ML14076.

Figure 12:
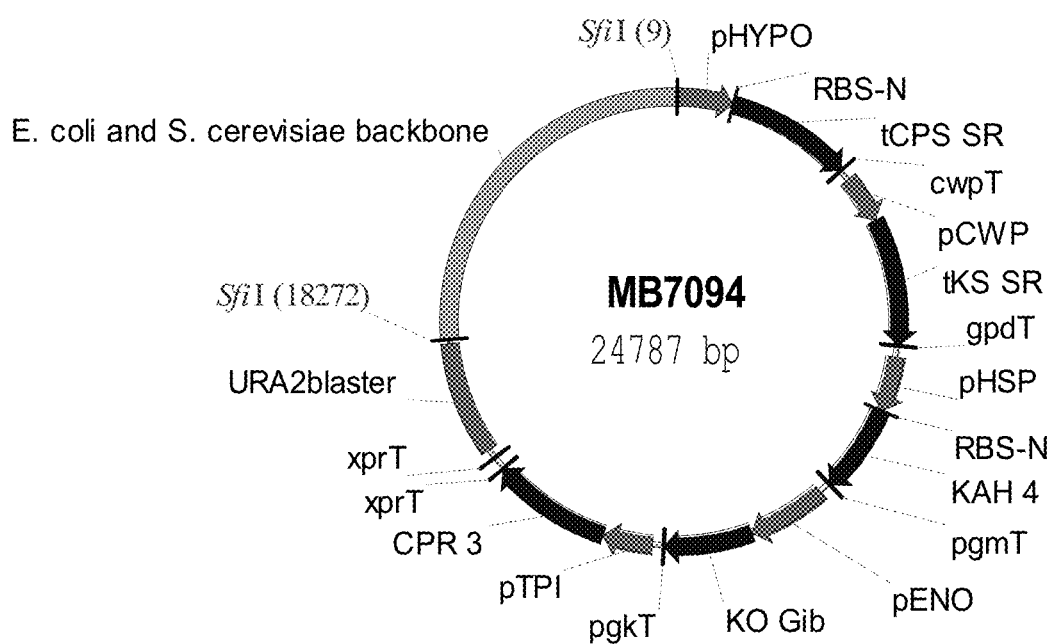
FIG. 12 sets out a schematic representation of the plasmid MB7094, encoding tCPS_SR, tKS_SR, KAH_4, KO_Gib, CPR_3, URA2.

Step 7. Strain ML14076 was transformed with a 19.0 kb fragment isolated by gel purification following SfiI digestion of plasmid MB7094 (FIG. 12). MB7094 encodes the tCPS_SR (SEQ ID NO: 20) linked to the pHYPO promoter (SEQ ID NO: 4) and cwpT terminator (SEQ ID NO: 10), the tKS_SR (SEQ ID NO: 21) linked to the pCWP promoter (SEQ ID NO: 6) and gpdT terminator (SEQ ID NO: 11), the KAH_4 (SEQ ID NO: 22) linked to the pHSP promoter (SEQ ID NO: 3) and pgmT terminator (SEQ ID NO: 12), the KO_Gib (SEQ ID NO: 23) linked to the pENO promoter (SEQ ID NO: 5) and pgkT terminator (SEQ ID NO: 13), the CPR_3 (SEQ ID NO: 24) linked to the pTPI promoter (SEQ ID NO: 7) and xprT terminator (SEQ ID NO: 9) and URA2blaster prototrophic marker. Transformants were selected on minimal medium lacking uracil. One selected rebaudioside A producing uracil prototroph was denoted ML14087.

Example 3. Mating MATA and MATB Lineage and Selecting Steviol Glycoside-Producing Progeny Strains of opposite mating types (ML14094 and ML14087) with complementary nutritional deficiencies (ADE1+ lys1- and ade1- LYS1+) were allowed to mate and then plated on selective media that would allow only diploids to grow (minimal media lacking both adenine and lysine). Diploid cells (ML14143) were then induced to undergo meiosis and sporulation by starvation, and the resulting haploid progenies were replica-plated to identify prototrophic isolates with hygromycin and nourseothricin resistance. One selected rebaudioside A-producing strain was denoted ML14737

Example 4. Making the Strain UGT2 La-Free

Figure 13:
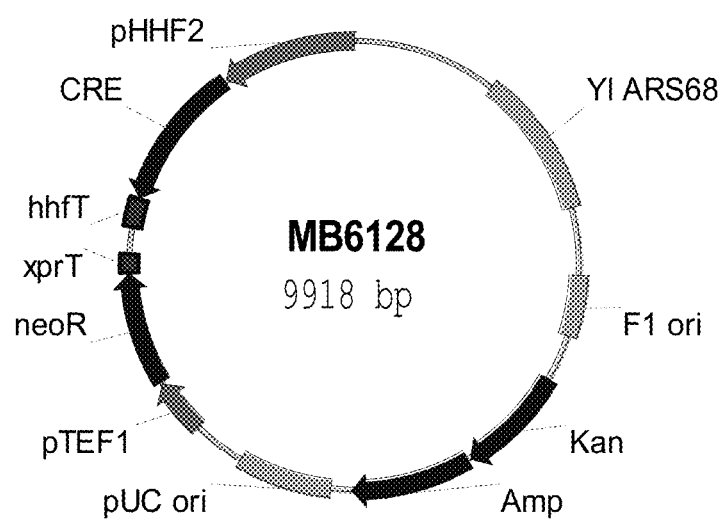
FIG. 13 sets out a schematic representation of the plasmid MB6128, encoding CRE, neoR.

The hygromycin antibiotic marker and the nourseothricin antibiotic marker were removed from strain ML14737 after transformation with MB6128 (FIG. 13) which encodes a construct for constitutive overexpression of the CRE recombinase. CRE recombinase deletes the antibiotics markers by recombination over the Lox66 and Lox71 sites. An inactive Lox72 site is left in the genome (Güldener et al, 1996, Lambert et al, 2007). Plasmid MB6128 is a CEN plasmid which replicates episomally in *Yarrowia lipolytica* and which contains the CRE recombinase coding region under control of the native *Yarrowia lipolytica* pHHF promoter and hhfT terminator, and a neoR (encoding for G418 resistance) under the control of the native *Yarrowia lipolytica* pTEF1 promoter and xprT terminator. After selection of MB6128 transformants on YPD+G418 and screening for transformants that lost hygromycin and nourseothricin resistance by successful Cre-Lox recombination, the sensitive colonies were grown on non-selective medium to remove the MB6128 CEN plasmid (spontaneous loss of the CEN plasmid). The resulting antibiotic marker-free variant is denoted ML14869. This strain no longer produces rebaudioside A due to the loss of UGT2_1a along with the hygromycin resistance and produces the intermediate rubusoside instead.

Example 5. Introduction of UGT2 10b

ML14869 was transformed with a 4.2 kb DNA fragment produced by PCR and purified following gel electrophoresis. The fragment encoded a sequence optimized variant of UGT2_10 b (SEQ ID NO: 25) and hygromycin resistance. The DNA fragment was generated by fusion PCR as follows. UGT2_10 b was codon pair optimized for expression in *Y. lipolytica* and synthesized by DNA2.0, linked to the native *Yarrowia lipolytica* pHSP promoter and gpdT terminator and flanked by connector sequences. This 1.4 kb DNA fragment was amplified using appropriate oligos and purified by gel electrophoresis. The HPH marker was flanked by lox sites, and linked to the *Ashbya gossypii* pTEF1 promoter and tef1T terminator and flanked by connector sequences. This 1.8 kb DNA fragment was amplified using appropriate oligos and purified by gel electrophoresis. A 4.2 kb DNA fragment was obtained by PCR using these two DNA fragments with followed by gel electrophoresis and purification. Transformation of ML14869 with this defined DNA fragment and selection on YPD+100 ug/ml hygromycin yielded the rebaudioside A producing strain ML14937.

Example 6. Making Strain ML14937 Marker-Free

The hygromycin antibiotic marker was removed from strain ML14937 after transformation with MB6128 (FIG. 13) which encodes a construct for constitutive overexpression of the CRE recombinase. CRE recombinase deletes the antibiotics markers by recombination over the Lox66 and Lox71 sites. An inactive Lox72 site is left in the genome (Güldener et al, 1996, Lambert et al, 2007). Plasmid MB6128 is a CEN plasmid which replicates episomally in *Yarrowia lipolytica* and which contains the CRE recombinase coding region under control of the native *Yarrowia lipolytica* pHHF promoter and hhfT terminator and a neoR (encoding for G418 resistance) under the control of the native *Yarrowia lipolytica* pTEF1 promoter and xprT terminator. After selection of MB6128 transformants on YPD+G418 and screening for transformants that lost hygromycin and nourseothricin resistance by successful Cre-Lox recombination, the sensitive colonies were grown on non-selective medium to remove the MB6128 CEN plasmid (spontaneous loss of the CEN plasmid). The resulting antibiotic marker-free variant is denoted ML14958.

Example 7. Transformation with Extra Gene Copies

Figure 14:
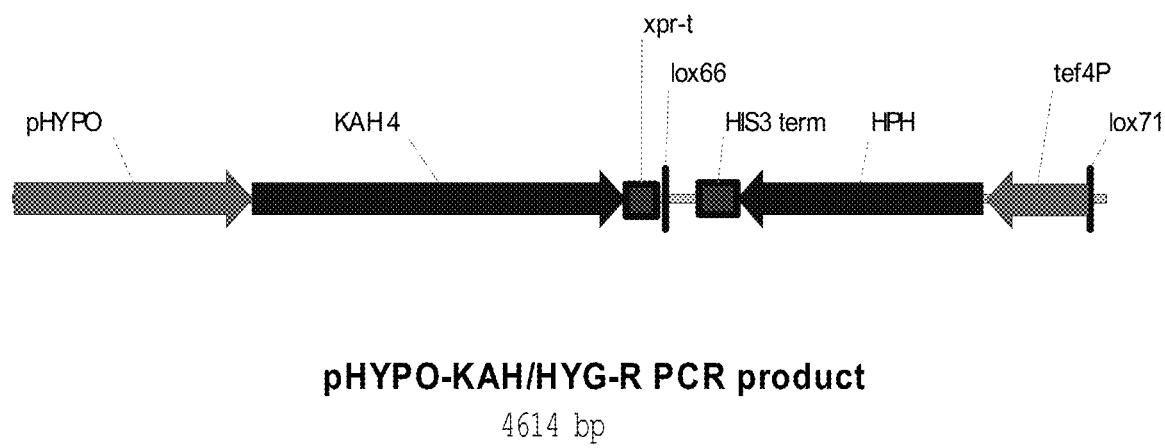
FIG. 14 sets out a schematic representation of the construct containing KAH and HPH.

Strain ML14958 was struck to YPD and grown overnight and then struck to 5-FOA plates to allow for recombination-mediated loss of the URA2 marker. One selected 5'-FOA resistant transformant was denoted ML15075. Strain ML15075 was transformed with 3 defined DNA fragments and selected for transformation on YPD with 100 ug/ml hygromycin. The three fragments were as follows:

1) a 4.6 kb DNA fragment encoding the KAH open reading frame linked to the native *Y. lipolytica* pHYPO promoter and the xprT terminator and also encoding the HPH hygromycin resistance gene flanked by lox sites, produced by PCR and purified following gel electrophoresis. Sequences were assembled in *Saccharomyces cerevisiae*, and DNA from this *S. cerevisiae* strain was used as template for PCR yielding the 4.6 kb DNA fragment (see FIG. 14) used to transform ML15075.

Figure 15:
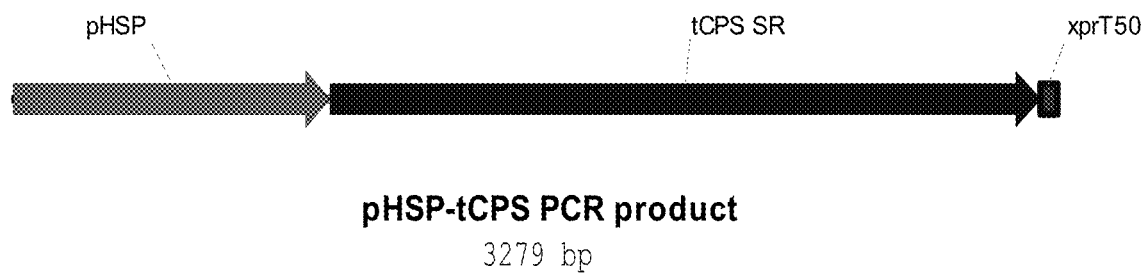
FIG. 15 sets out a schematic representation of the construct containing tCPS_SR.

2) a 3.3 kb DNA fragment encoding the tCPS open reading frame linked to the native *Y. lipolytica* pHSP promoter and xprT terminator, produced by PCR and purified following gel electrophoresis. Sequences were assembled in *Saccharomyces cerevisiae*, and DNA from this *S. cerevisiae* strain was used as template for PCR yielding the 3.3 kb DNA fragment (FIG. 15) used to transform ML15075.

Figure 16:
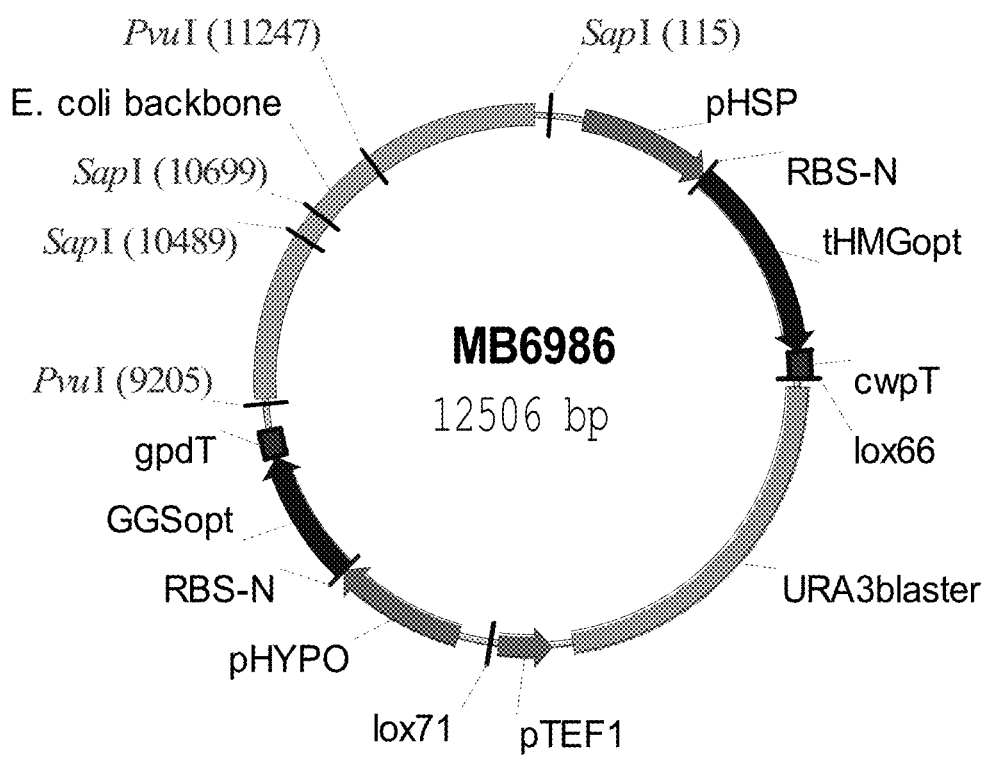
FIG. 16 sets out a schematic representation of the plasmid MB6986, encoding tHMG, URA3, GGS.

3) a 9.1 kb fragment isolated by gel purification following PvuI/SapI digestion of plasmid MB6986 (FIG. 16). This construct encodes tHMG linked to the native *Y. lipolytica* HSP promoter and CWP terminator, the lox-flanked URA3blaster prototrophic marker, and GGS1 linked to the native *Y. lipolytica* HYPO promoter and GPD terminator. ML15075 is auxotrophic due to a mutation in ura2, so this fragment was not selected for.

One selected hygromycin-resistant transformant was denoted ML15085.

Example 8. Transformation of Extra Copies of tHMG and GGS

Strain ML15085 was transformed with a 8.4 kb fragment isolated by gel purification following PvuI/SapI digestion of plasmid MB6988 (FIG. 10). This construct encodes tHMGopt linked to the native *Y. lipolytica* pHSP promoter and cwpT terminator, the lox-flanked URA2blaster prototrophic marker, and GGSopt linked to the native *Y. lipolytica* pHYPO promoter and gpdT terminator. Transformants were selected on minimal medium lacking uracil. One selected uracil prototroph was denoted ML15086.

Example 9. Making Strain ML15086 Marker-Free

The hygromycin antibiotic marker was removed from strain ML15086 after transformation with MB6128 (FIG. 13) which encodes a construct for constitutive overexpression of the CRE recombinase. CRE recombinase deletes the antibiotics markers by recombination over the Lox66 and Lox71 sites. An inactive Lox72 site is left in the genome (Güldener et al, 1996, Lambert et al, 2007). Plasmid MB6128 is a CEN plasmid which replicates episomally in *Yarrowia lipolytica* and which contains the CRE recombinase coding region under control of the native *Yarrowia lipolytica* pHHF promoter and hhfT terminator and a neoR (encoding for G418 resistance) under the control of the native *Yarrowia lipolytica* pTEF1 promoter and xprT terminator.

After selection of MB6128 transformants on YPD+G418 and screening for transformants that lost hygromycin and nourseothricin resistance by successful Cre-Lox recombination, the sensitive colonies were grown on non-selective medium to remove the MB6128 CEN plasmid (spontaneous loss of the CEN plasmid). One prototrophic, antibiotic marker-free variant is denoted ML15087.

Example 10. Disruption of YALI0C08701 in *Y. lipolytica* ML15087

To increase the efficiency of targeted transporter disruptions and avoid integration events at other loci in the genome than targeted for, YALI0C08701 (SEQ ID NO: 26), an important factor in non-homologous end joining, was disrupted. Disruption constructs were designed based on single cross-over integration using internal homologous fragments to target the disruption construct to the YALI0C08701 ORF. The internal homologous fragments used to assemble the disruption constructs were PCR amplified from *Y. lipolytica* genomic DNA using suitable primers which were elongated with appropriate connector sequences. The total length of the PCR fragments was 600 bp. 500 bp of these fragments are homologous to the targeted YALI0C08701 and 50 bp to the vector backbone and KanMX marker cassette. The KanMX marker cassette was PCR amplified with suitable primers. For both flanks and marker cassette six 50 µl PCR reactions were performed using Phusion polymerase (New England Biolabs) according to suppliers' instructions. The PCR products were purified and concentrated using NucleoSpin Gel and PCR Clean-up Kit (Machery Nagel).

Figure 17:
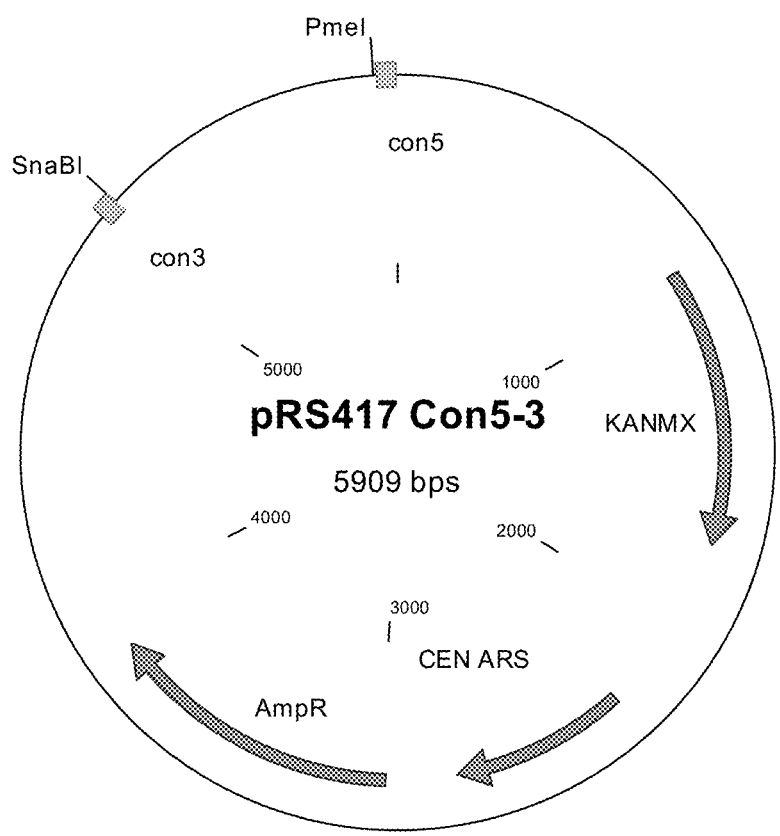
FIG. 17 sets out a schematic representation of the plasmid pRS417 Con5-3.

The flanks and marker were assembled in the SnaBI/PmeI digested pRS417 5_3 (FIG. 17) shuttle vector backbone in-vivo by transforming both flanks, the KanMX fragment and the linear pRS417 5_3 shuttle vector to *S. cerevisiae* CEN.PK113-7D. After transformation and recovery for 2 hours in YEPhD at 30° C. the cells were plated on YEPhD agar with 200 µg/ml G418 (Invitrogen). The plates were incubated at 30° C. for 2 days. Transformants were cultured in YEPD+200 µg/ml G418 at 30° C. Plasmid DNA was isolated and purified.

Correct assembly of the disruption cassettes was established with diagnostic PCR. The expression cassettes were PCR amplified in six 50 µl PCR reactions. The PCR product was purified and concentrated using NucleoSpin Gel and PCR Clean-up Kit (Machery Nagel). 1 µg of the PCR amplified disruption cassette was transformed to *Y. lipolytica* strain ML15087. After transformation and recovery for 2 hours in YEPhD at 30° C. the cells were plated on YEPhD agar with 400 µg/ml G418. The plates were incubated at 30° C. for 2 days. Transformants were purified by re-streaking them on YEPhD agar with 400 µg/ml G418. One of the transformants was named STV2049. Correct integration was established with diagnostic PCR using appropriate oligo's.

Example 11. Disruption of Transporter YALI0E25201 in *Y. lipolytica* STV2049

Figure 18:
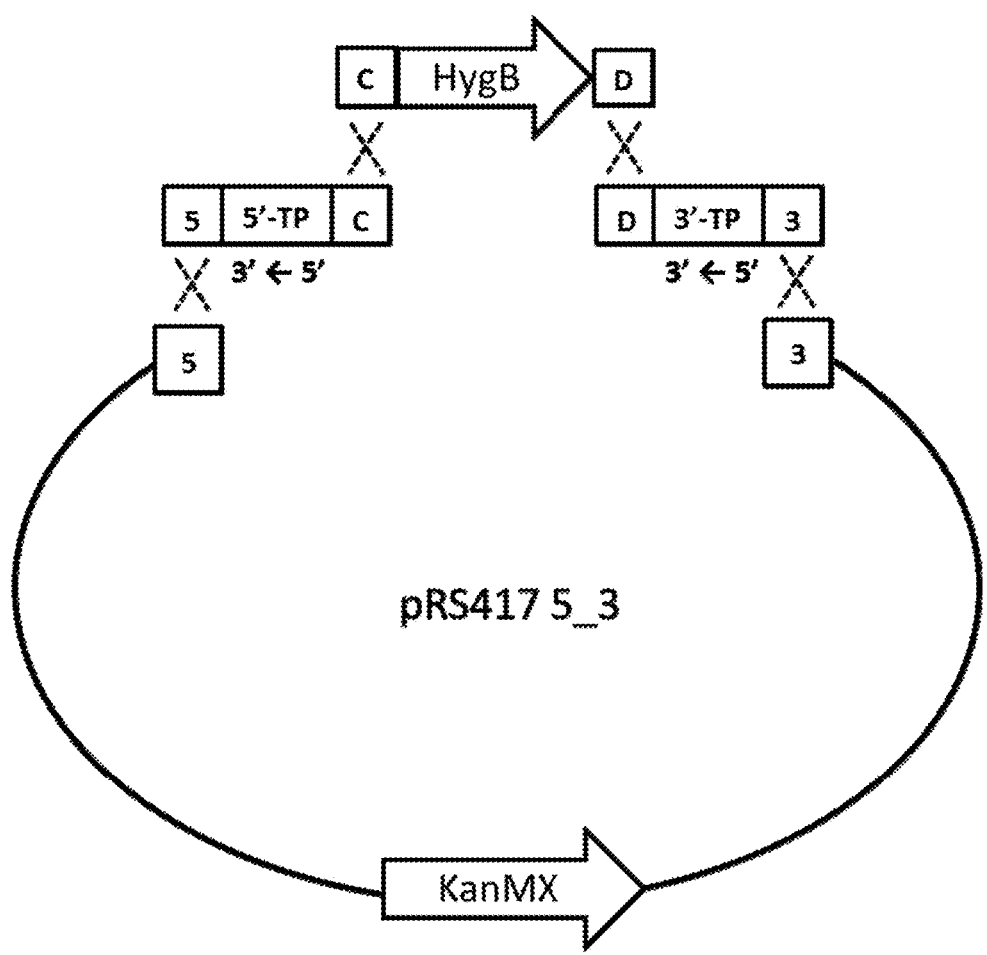
FIG. 18 sets out a schematic representation of the assembly of the HygB marker with the transporter internal fragments in plasmid pRS417 5-3.

Disruption constructs were designed based on single cross-over integration using internal homologues fragments to target the disruption construct to the YALI0E25201 ORF (SEQ ID NO: 27). The internal homologous fragments used to assemble the disruption constructs were ordered as synthetic DNA in the form of gBlocks (IDT) with a total length of 700 bp. 600 bp of these fragments are homologous to the targeted transporter YALI0E25201 and 50 bp to the vector backbone (5 and 3 connector sequence, FIG. 18) and HygB marker cassette (c and d connector sequence, FIG. 18). The HygB marker cassette was PCR amplified with suitable primers using Phusion polymerase (New England Biolabs) according to suppliers' instructions. The PCR product was purified and concentrated using NucleoSpin Gel and PCR Clean-up Kit (Machery Nagel).

The flanks and marker were assembled in the SnaBI/PmeI digested pRS417 5_3 shuttle vector backbone in-vivo by transforming both flanks, the HygB fragment and the linear pRS417 5_3 shuttle vector to *S. cerevisiae* CEN-PK-7D. See FIG. 18.

After transformation and recovery for 2 hours in YEPhD at 30° C. the cells were plated on YEPhD agar with 200 µg/ml G418 (Invitrogen). The plates were incubated at 30° C. for 2 days. Transformants were cultured in YEPD+200 µg/ml G418 at 30° C., 550 rpm and 80% humidity. Plasmid DNA was isolated and purified. Correct assembly of the disruption cassettes was established with diagnostic PCR.

Figure 19:
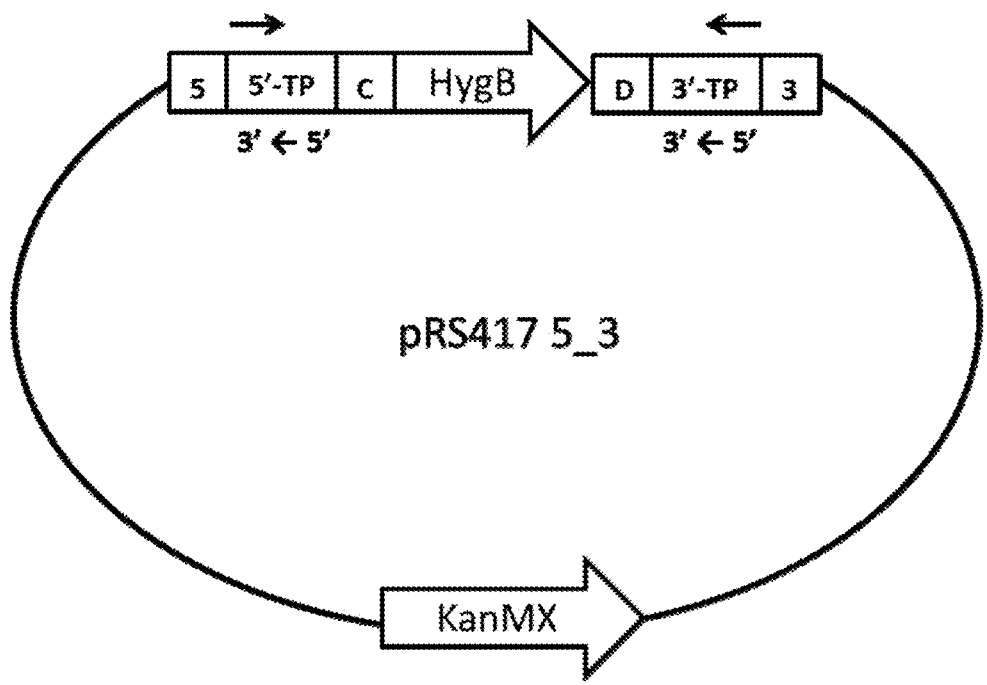
FIG. 19 sets out a schematic representation of the PCR amplification of the transporter disruption constructs off plasmid pRS417 5-3 containing the HYG marker and transporter internal fragments.
Figure 19:
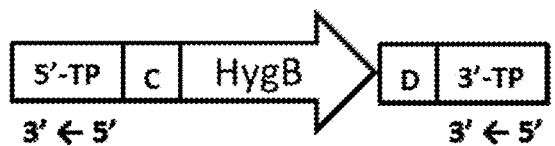
Figure 20:
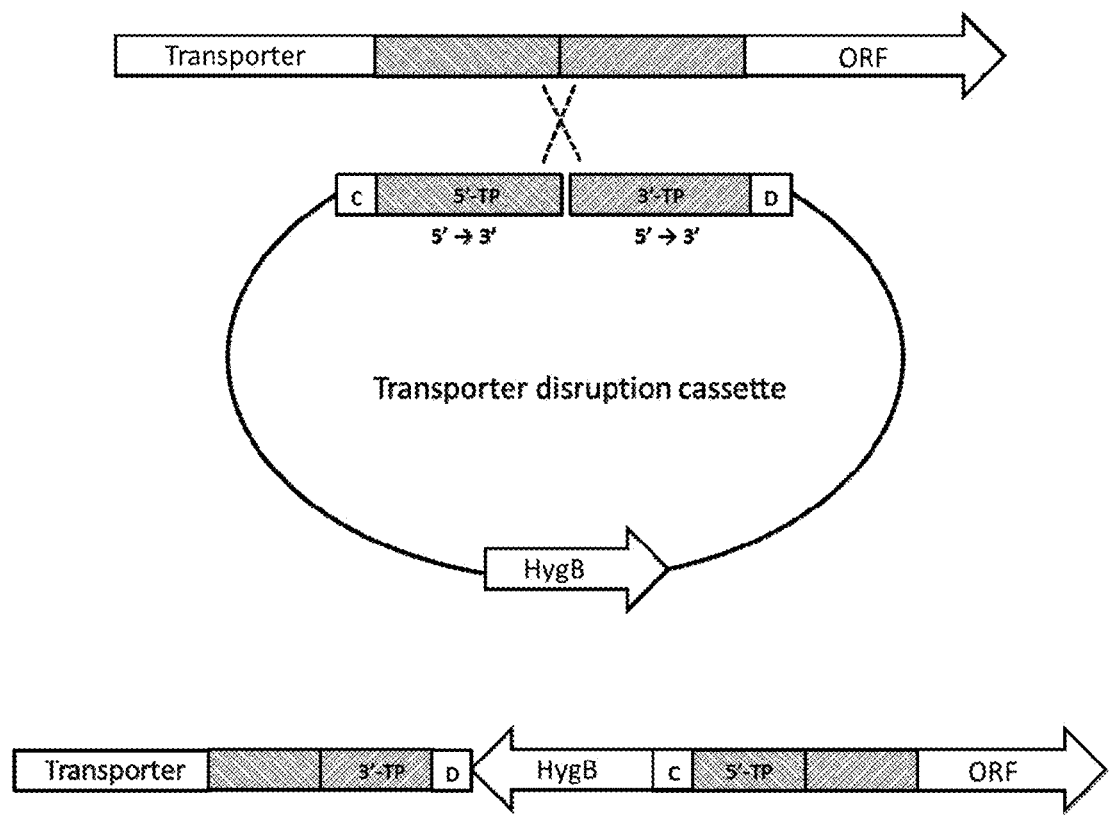
FIG. 20 sets out a schematic representation of the recombination event at the genome resulting in a disruption of the transporter gene and integration of the HygB marker.

The expression cassettes were PCR amplified (FIG. 19) in six 50 µl PCR reactions. The PCR product was purified and concentrated using NucleoSpin Gel and PCR Clean-up Kit (Machery Nagel). 1 µg of the PCR amplified disruption cassette was transformed to *Y. lipolytica* STV2049. After transformation and recovery for 2 hours in YEPhD at 30° C. the cells were plated on YEPhD agar with 100 µg/ml HygB (Invitrogen). The plates were incubated at 30° C. for 2 days. Transformants were purified by re-streaking them on YEPhD agar with 100 µg/ml HygB. Correct integration, as illustrated in FIG. 20, was established with diagnostic PCR using appropriate oligo's.

Example 12. Fermentation of *Y. lipolytica* STV2049 and STV2049 YALI0E25201 Disruption Transformants A pre-culture was inoculated with colony material from YEPh-D agar. The pre-culture was grown in 96-Half Deep Well Plate containing 200 µl 0.5×YEP with 2% glucose per well. The plates were sealed with a breathable seal and incubated in an Infors incubator at 30° C., 80% humidity, 750 rpm for 48 hours.

40 µl of the 96-well pre-culture was used to inoculate a 24-well deep well plate containing 2.5 ml of 0.25×YEP with 5% glucose per well. Plates were sealed with a breathable seal and incubated in an Infors incubator at 30° C., 80% humidity, 500 rpm for 120 hours.

The 24-well plates were spun down in an MTP centrifuge and 1 ml of the supernatant was harvested. The remaining supernatant was decanted from the pellet. The supernatant fraction was diluted 1000 times in 33% Acetonitrile. The pellet was suspended in 2.5 ml milli-Q and 1 ml was transferred to a 96-well DWP. The plate was sealed with an aluminium seal and incubated for 10 minutes at 90° C. The plate was cooled down to room temperature and 0.5 ml of 100% Acetonitrile was added and homogenized. The plates were centrifuged at 2088×g for 10 minutes to pellet cell material and debris. The supernatant of the pellet fraction was diluted 33 times in 33% acetonitrile resulting in a combined 50 times dilution. Samples were analyzed for Rebaudioside A and other steviolglycosides using LC/MS.

We found that the strains that had the YALI0E25201 disruption produced lower titers of Rebaudioside A in the supernatant compared to the parent strain. The concentration of Rebaudioside A was approximately three fold lower in the transporter disruption strain compared to the parental strain (see Table 1).

TABLE 1

Rebaudioside A supernatant concentrations in 24-well fermentations. Six replicate cultures were performed for parent strain STV2049. Duplicate cultures of three independent STV2049 ΔYALI0E25201 transformants were performed. The averages are taken for the data in Table 1.

| Strain | RebA supernatant (mg/L) |
|---|---|
| STV2049 | 441 |
| STV2049 ΔYALI0E25201 A | 155 |

The observation that the concentration of Rebaudioside A in the supernatant is lower for the transporter disruption strain compared to the reference strain was also seen for Stevioside, Rubusoside, and to a lesser degree for Rebaudioside D and Steviol-19-monoside (see Tables 2 to 5).

TABLE 2

Stevioside supernatant concentrations in 24-well fermentations. Six replicate cultures were performed for parent strain STV2049. Duplicate cultures of three independent STV2049 ΔYALI0E25201 transformants were performed. The averages are taken for the data in Table 2.

| Strain | Stevioside supernatant (mg/L) |
|---|---|
| STV2049 | 144 |
| STV2049 ΔYALI0E25201 A | 46.9 |

TABLE 3

Rubusoside supernatant concentrations in 24-well fermentations. Six replicate cultures were performed for parent strain STV2049. Duplicate cultures of three independent STV2049 ΔYALI0E25201 transformants were performed. The averages are taken for the data in Table 3.

| strain | Rubusoside supernatant (mg/L) |
|---|---|
| STV2049 | 42.2 |
| STV2049 ΔYALI0E25201 A | 17.2 |

TABLE 4

Rebaudioside D supernatant concentrations in 24-well fermentations. Six replicate cultures were performed for parent strain STV2049. Duplicate cultures of three independent STV2049 ΔYALI0E25201 transformants were performed. The averages are taken for the data in Table 4.

| Strain | RebD supernatant (mg/L) |
|---|---|
| STV2049 | 39.7 |
| STV2049 ΔYALI0E25201 A | 32.6 |

TABLE 5

Steviol-19-monoside supernatant concentrations in 24-well fermentations. Six replicate cultures were performed for parent strain STV2049. Duplicate cultures of three independent STV2049 ΔYALI0E25201 transformants were performed. The averages are taken for the data in Table 5.

| Strain | Steviol-19-monoside supernatant (mg/L) |
|---|---|
| STV2049 | 35.7 |
| STV2049 ΔYALI0E25201 A | 20.2 |

The effect of disrupting the transporter gene was most pronounced on the transport of the aforementioned steviol glycosides, and not a consequence of a general decreased production of steviol glycosides. This is illustrated when the concentration of all steviol glycosides are measured in the pellet fraction (Table 6). Here it can be seen that in the YALI0E25201 disruption strain, the concentration of all steviol glycosides in the pellet fraction is increased in the transporter disruption strain, indicative of reduced transport.

TABLE 6

Concentration of the sum of all steviol glycosides (Rebaudioside A, Stevioside, Rebaudioside B, Rebaudioside D, Steviolbioside, Rubusoside, Steviol-19-monoside, Steviol-13-monoside and Rebaudioside M) in the pellet fraction in 24-well fermentations. Six replicate cultures were performed for parent strain STV2049. Duplicate cultures of three independent STV2049 ΔYALI0E25201 transformants were performed. The averages are taken for the data in Table 6.

| strain | Sum steviol glycosides pellet (uM) |
|---|---|
| STV2049 | 34 |
| STV2049 ΔYALI0E25201 A | 67 |

Example 13. Over-Expression of the YALI0E25201 Transporter in Steviol Glycosides Producing *Y. lipolytica* Strains To further demonstrate the functionality of the YALI0E25201 transporter, the YALI0E25201 ORF was assembled in an expression cassette with the *Y. lipolytica* YP006 promoter and *Y. lipolytica* TEF4 terminator. The cassettes were assembled in the pRS417 5_3 vector together with the Nourseothricin marker. As a negative control the same cassette only containing the Nourseothricin marker was constructed. The expression cassettes were PCR amplified and the obtained fragments were transformed to three different strains: strains STV2049 is a strain producing mostly RebA, and is described above. Also, the transporter deletion strain is included (STV2049 ΔYALI0E25201 (described above)). The third strain is STV2170, a strain producing mostly RebM. STV2170 was build similarly to strain STV2049, and the genotype is listed below in Table 7.

TABLE 7

Genotype of strain STV2170. Between brackets indicates the gene copy number present in the strain

| Strain name | genotype |
|---|---|
| STV2170 | tHMG (2; SEQ ID NO: 15) GGS (2; SEQ ID NO: 16) CarG (1; SEQ ID NO: 32) CPS (2 SEQ ID NO: 20) KS (2; SEQ ID NO: 21) |

TABLE 7-continued

Genotype of strain STV2170. Between brackets indicates the gene copy number present in the strain

| Strain name | genotype |
|---|---|
| | KO_Gib (2; SEQ ID NO: 23), KAH4 (4; SEQ ID NO: 22) CPR3 (2; SEQ ID NO: 24) UGT1 (5; SEQ ID NO: 17) UGT2_6b (2; SEQ ID NO: 33) UGT3 (2; SEQ ID NO: 18) UGT4 (4; SEQ ID NO: 19) RT18 (1; SEQ ID NO: 34) |

Six transformants were selected for each combination of strain and expression cassette. The transformants were grown in 24-well fermentation and the supernatant- and pellet fractions were analyzed by LC-MS as described in Example 12.

TABLE 8

RebA supernatant and pellet concentrations in 24-well fermentations in the control strain (STV2049 with NatMX marker) and YALI0E25201 transporter over-expression strain (STV2049 with transporter and NatMX marker)

| Strain | RebA supernatant (mg/L) | RebA pellet (mg/L) |
|---|---|---|
| STV2049 control | 392 | 15 |
| YALI0E25201 O.E. | 461 | 15 |

These data illustrate that over-expression of the YALI0E25201 transporter has a positive effect on extracellular RebA production.

TABLE 9

RebM supernatant and pellet concentrations in 24-well fermentations in the control strain (STV2049 with NatMX marker) and YALI0E25201 transporter over-expression strain (STV2049 with transporter and NatMX marker)

| Strain | RebM supernatant (mg/L) | RebM pellet (mg/L) |
|---|---|---|
| STV2049 control | 59 | 10 |
| YALI0E25201 O.E. | 43 | 4 |

RebM production in this strain is low compared to RebA production, but even so, the effect of the transporter over-expression can be seen in the concentrations of RebM. As RebA is more efficiently exported to outside the cell in the YALI0E25201 over-expression strain, less RebA will be available for further glycosylation inside the cell, and hence resulting in lower production of RebM, particularly in the pellet fraction.

TABLE 10

RebA supernatant and pellet concentrations in 24-well fermentations in the transporter deletion strain (STV2049 ΔYALI0E25201 with NatMX marker) and the same background with the YALI0E25201 transporter over-expressed (STV2049 ΔYALI0E25201 with transporter and NatMX marker.)

| Strain | RebA supernatant (mg/L) | RebA pellet (mg/L) |
|---|---|---|
| STV2049 ΔYALI0E25201 control | 114 | 23 |
| STV2049 ΔYALI0E25201 YALI0E25201 O.E. | 431 | 17 |

Upon over-expression of the YALI0E25201 transporter in the YALI0E25201 deletion strain, the extracellular production of RebA is greatly enhanced, and restored to similar levels as the reference strain without the transporter deletion.

TABLE 11

RebM supernatant and pellet concentrations in 24-well fermentations in the transporter deletion strain (STV2049 ΔYALI0E25201 with NatMX marker) and the same background with the YALI0E25201 transporter over-expressed (STV2049 ΔYALI0E25201 YALI0E25201 O.E.)

| Strain | RebM supernatant (mg/L) | RebM pellet (mg/L) |
|---|---|---|
| STV2049 ΔYALI0E25201 control | 6 | 45 |
| STV2049 ΔYALI0E25201 YALI0E25201 O.E. | 22 | 1 |

In the transporter deletion strain, steviol glycosides including RebA accumulate in the cell, allowing for continued glycosylation inside the cell. As a consequence, RebM concentrations may increase. In the transporter deletion strain, the concentration RebM in the pellet fraction is much higher than in the supernatant. Upon restoring transport this is reversed: less accumulation of intracellular RebM, and more export of RebM.

TABLE 12

RebA supernatant and pellet concentrations in 24-well fermentations in the RebM production control strain (STV2170 with NatMX marker) and YALI0E25201 transporter over- expression strain (STV2170 with transporter and NatMX marker)

| Strain | RebA supernatant (mg/L) | RebA pellet (mg/L) |
|---|---|---|
| STV2170 control | 107 | 22 |
| STV2170 YALI0E25201 O.E. | 283 | 8 |

Over-expression of the YALI0E25201 transporter results in greatly increased extracellular production of RebA, and greatly reduced accumulation of RebA in the pellet.

TABLE 13

RebM supernatant and pellet concentrations in 24-well fermentations in the RebM production control strain (STV2170 with NatMX marker) and YALI0E25201 transporter over- expression strain (STV2170 with transporter and NatMX marker)

| Strain | RebM supernatant (mg/L) | RebM pellet (mg/L) |
|---|---|---|
| STV2170 control | 631 | 132 |
| STV2170 YALI0E25201 O.E. | 660 | 61 |

Over-expression of the YALI0E25201 transporter results in increased extracellular production of RebM, and reduced accumulation of RebM in the pellet.

Together these data illustrate that over-expression of the YALI0E25201 transporter has a positive effect on extracellular RebA and RebM production. Not only is the distribution of RebA and RebM production in the supernatant fraction versus the pellet fraction favourable when the transporter is over-expressed, over-expression of the YALI0E25201 transporter also has a positive effect on the total amount of RebA and RebM production.

TABLE 14

| Description of the sequence listing | | | |
|---|---|---|---|
| SEQ ID NO | Description | SEQ ID NO | Description |
| SEQ ID NO: 1 | UGT2_1a CpO for *Y. lipolytica* | SEQ ID NO: 18 | UGT3 CpO for *Y. lipolytica* |
| SEQ ID NO: 2 | PGM promoter from *Y. lipolytica* | SEQ ID NO: 19 | UGT4 CpO for *Y. lipolytica* |
| SEQ ID NO: 3 | HSP promoter from *Y. lipolytica* | SEQ ID NO: 20 | tCPS from *S. rebaudiana* CpO for *Y. lipolytica* |
| SEQ ID NO: 4 | HYPO promoter from *Y. lipolytica* | SEQ ID NO: 21 | tKS from *S. rebaudiana* CpO for *Y. lipolitica* |
| SEQ ID NO: 5 | ENO promoter from *Y. lipolytica* | SEQ ID NO: 22 | KAH_4 CpO for *Y. lipolitica* |
| SEQ ID NO: 6 | CWP promoter from *Y. lipolytica* | SEQ ID NO: 23 | KO from *Gibberella fujikori* CpO for *Y. lipolytica* |
| SEQ ID NO: 7 | TPI promoter from *Y. lipolytica* | SEQ ID NO: 24 | CPR_3 CpO for *Y. lipolytica* |
| SEQ ID NO: 8 | YP001 promoter from *Y. lipolytica* | SEQ ID NO: 25 | UGT2_10b CpO for *Y. lipolytica* |
| SEQ ID NO: 9 | Xpr terminator from *Y. lipolytica* | SEQ ID NO: 26 | YALI0C08701 WT CDS |
| SEQ ID NO: 10 | Cwp terminator from *Y. lipolytica* | SEQ ID NO: 27 | YALI0E25201 WT CDS |
| SEQ ID NO: 11 | Gpd terminator from *Y. lipolytica* | SEQ ID NO: 28 | YALI0E25201 CpO for *Y. lipolytica* |
| SEQ ID NO: 12 | Pgm terminator from *Y. lipolytica* | SEQ ID NO: 29 | YALI0E25201 WT from *Y. lipolytica* |
| SEQ ID NO: 13 | Pgk terminator from *Y. lipolytica* | SEQ ID NO: 30 | YP006 promoter from *Y. lipolytica* |
| SEQ ID NO: 14 | act1T terminator from *Y. lipolytica* | SEQ ID NO: 31 | Tef4 terminator from *Y. lipolytica* |
| SEQ ID NO: 15 | tHMG CpO for *Y. lipolitica* | SEQ ID NO: 32 | CarG codon optimized for *Y. lipolytica* |
| SEQ ID NO: 16 | GGS CpO for *Y. lipolytica* | SEQ ID NO: 33 | UGT2_6b CpO for *Y. lipolytica* |
| SEQ ID NO: 17 | UGT1 CpO for *Y. lipolytica* | SEQ ID NO: 34 | RT18 CpO for *Y. lipolytica* |

The invention claimed is:

1. A recombinant cell capable of producing a steviol glycoside which overexpresses a nucleic acid encoding a polypeptide comprising the amino acid sequence set forth in SEQ ID NO:29 or an amino acid sequence having at least 98% sequence identity to the amino acid sequence set forth in SEQ ID NO:29.

2. The recombinant cell according to claim 1, which further comprises one or more recombinant nucleotide sequence(s) encoding:
   - a polypeptide having ent-copalyl pyrophosphate synthase activity;
   - a polypeptide having ent-Kaurene synthase activity;
   - a polypeptide having ent-Kaurene oxidase activity; and
   - a polypeptide having kaurenoic acid 13-hydroxylase activity.

3. The recombinant cell according to claim 1, wherein the host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia*, Yamadazyma, or *Escherichia*.

4. The recombinant host according to claim 3, wherein the recombinant host is a *Saccharomyces cerevisiae* cell, a *Yarrowia* lipolytica cell, a *Candida* krusei cell, or an *Escherichia coli* cell.

5. The recombinant cell according to claim 1, wherein the polypeptide comprises an amino acid sequence having at least 99% sequence identity to SEQ ID NO:29.

6. The recombinant cell according to claim 1, wherein the polypeptide mediates steviol glycoside transport and wherein the amount of total produced steviol glycoside outside the cell, as compared to inside the cell, is higher as compared to a corresponding cell which does not overexpress the nucleic acid.

7. A process for the preparation of a steviol glycoside which comprises fermenting the recombinant cell according to claim 1 in a suitable fermentation medium and, optionally, recovering the steviol glycoside.

8. The process according to claim 7 for the preparation of a steviol glycoside, wherein the process is carried out on an industrial scale.

\* \* \* \* \*

SEQUENCE LISTING

<160> NUMBER OF SEQ ID NOS: 34

<210> SEQ ID NO 1
<211> LENGTH: 1422
<212> TYPE: DNA
<213> ORGANISM: Artificial sequence
<220> FEATURE:
<223> OTHER INFORMATION: UGT2_1a CpO for Y. lipolitica

<400> SEQUENCE: 1

```
atggccacct ccgactccat tgtcgacgac cgaaagcagc tgcacgttgc caccttcccc      60
tggctcgcct ttggccacat tctgccctac ctccagctct ccaagctcat tgctgagaag     120
ggccacaagg tttctttcct gtccaccacc cgaaacatcc agcgactctc ctcccacatc     180
tctcctctca tcaacgttgt ccagctcacc ctcccccgag tccaggagct ccccgaggat     240
gccgaggcca ccactgatgt ccaccccgag gacatcccct acctcaagaa ggcctccgac     300
ggtctgcagc ccgaggtcac ccgattcctc gagcagcact ctcccgactg gatcatctac     360
gactacaccc actactggct cccctccatt gctgcttctc tcggtatctc tcgagcccac     420
ttctccgtca ccaccccctg ggccattgct tacatgggcc cctctgctga cgccatgatc     480
aacggttccg acggccgaac caccgtcgag gatctcacca ccctcccaa gtggttcccc     540 ttccccacca aggtctgctg gcgaaagcac gatctcgccc gactcgtccc ctacaaggcc     600
```

```
cccggtatct ccgacggtta ccgaatgggt ctggttctca agggctccga ctgtctgctc      660
tccaagtgct accacgagtt tggtacccag tggctccccc tgctcgagac tctgcaccag      720
gtccccgttg tccccgtcgg tctgctccct cccgagatcc ccggtgacga aaggacgag       780 acttgggttt ccatcaagaa gtggctcgac ggcaagcaga agggctccgt cgtctacgtt      840
gctctcggct ccgaggttct tgtctcccag actgaggtcg tcgagctcgc cctcggtctg      900
gagctctccg tctgcccctt cgtctgggcc taccgaaagc ccaagggtcc cgccaagtcc      960
gactccgtcg agctccccga cggtttcgtc gagcgaactc gagatcgagg tctggtctgg     1020
acctcttggg ctccccagct ccgaatcctc tcccacgagt ccgtctgcgg tttcctgacc     1080
cactgtggtt ccggctccat tgtcgagggc ctcatgttcg gccaccccct catcatgctg     1140
cccatcttcg gtgaccagcc cctcaacgcc cgactcctcg aggacaagca ggtcggtatc     1200
gagatccccc gaaacgaaga ggacggctgc ctcaccaagg agtctgttgc ccgatctctg     1260
cgatctgttg ttgtcgagaa agagggtgag atctacaagg ccaacgcccg agagctctcc     1320
aagatctaca cgacaccaa ggtcgagaag gagtacgttt cccagtttgt cgactacctc      1380
gagaagaacg cccgagctgt cgccattgac cacgagagtt aa                        1422

<210> SEQ ID NO 2
<211> LENGTH: 803
<212> TYPE: DNA
<213> ORGANISM: Yarrowia lipolytica

<400> SEQUENCE: 2
taccaaccac agattacgac ccattcgcag tcacagttca ctagggtttg ggttgcatcc       60
gttgagagtg gtttgttttt aaccttctcc atgtgctcac tcaggttttg ggttcagatc      120
aaatcaaggc gtgaaccact gtttgaggac aaatgtgaca caaccaacca gtgtcagggg      180
caagtccgtg acaaggggga agatacaatg caattactga cagttacgga ctgcctcgat      240
gccctaacct tgccccaaaa taagacaact gtcctcgttt aagcgcaacc ctattcagcg      300
tcacgtcata atagcgtttg gatagcacta gtctatgagg agcgttttat gttgcggtga      360
gggcgattgg tgctcatatg ggttcaattg aggtggtgga acgagcttag tcttcaattg      420
aggtgcgagc gacacaattg ggtgtcacgt ggcctaattg acctcggatc gtggagtccc      480
cagttataca gcaaccacga ggtgcatgag taggagacgt caccagacaa tagggttttt      540
ttggactgga gagggtaggg caaaagcgct caacgggctg tttggggagc tatgggggag      600
gaattggcga tatttgtgag gttgacggct ccgatttgcg tgttttgtcg cttctgcatc      660
tccccatacc catatcttcc ctccccacct cttttccacga taattttacg gatcagcaat     720
aaggttcctt ctcctagttt ccacgtccat atatatctat gctgcgtcgt ccttttcgtg      780
acatcaccaa aacacataca aaa                                              803

<210> SEQ ID NO 3
<211> LENGTH: 995
<212> TYPE: DNA
<213> ORGANISM: Yarrowia lipolytica

<400> SEQUENCE: 3
ctgtacctgc tgtggaccac gcacggcgga acgtaccgta caaatatttt cttgctcaca       60
tgactctctc tcggccgcgc acgccggtgg caaattgctc ttgcattggc tctgtctcta      120
gacgtccaaa ccgtccaaag tggcagggtg acgtgatgcg acgcacgaag gagatggccc      180
ggtggcgagg aaccggacac ggcgagccgg cgggaaaaaa ggcggaaaac gaaaagcgaa      240
```

-continued

```
gggcacaatc tgacggtgcg gctgccacca acccaaggag gctattttgg gtcgctttcc      300
atttcacatt cgccctcaat ggccactttg cggtggtgaa catggtttct gaaacaaccc      360
cccagaatta gagtatattg atgtgtttaa gattgggttg ctatttggcc attgtggggg      420
agggtagcga cgtggaggac attccagggc gaattgagcc tagaaagtgg taccattcca      480
accgtctcag tcgtccgaat tgatcgctat aactatcacc tctctcacat gtctacttcc      540
ccaaccaaca tccccaacct ccccacact aaagttcacg ccaataatgt aggcactctt       600
tctgggtgtg ggacagcaga gcaatacgga ggggagatta cacaacgagc cacaattggg      660
gagatggtag ccatctcact cgacccgtcg acttttggca acgctcaatt acccaccaaa      720
tttgggctgg agttgagggg accgtgttcc agcgctgtag gaccagcaac acacacggta      780
tcaacagcaa ccaacgcccc cgctaatgca cccagtactg cgcaggtgtg ggccaggtgc      840
gttccagatg cgagttggcg aaccctaagc cgacagtgta cttttttggga cgggcagtag    900 caatcgtggg cggagacccc ggtgtatata aaggggtgga gaggacggat tattagcacc     960
aacacacaca cttatactac atgctagcca caaaa                                 995
```

<210> SEQ ID NO 4
<211> LENGTH: 1004
<212> TYPE: DNA
<213> ORGANISM: Yarrowia lipolytica

<400> SEQUENCE: 4

```
gtcagaaggg gcagctctaa acgaagaact gcggtcaggt gacacaactt tttccatctc      60
agggtgtgtc gcgtgtgctt catccaaact ttagttgggg ttcgggttcg cgcgagatga     120
tcacgtgccc tgatttggtg tcgtcccccg tcgcgctgcg cacgtgattt atttatttcc     180
ggtggctgct gtctacgcgg ggccttctct gcccttctgt ttcaaccttc gggcggttct    240
cgtaaccagc agtagcaatc catttcgaaa ctcaaagagc taaaaacgtt aaacctcagc    300
agtcgctcga cgaatgggct gcggttggga agcccacgag gcctatagcc agagcctcga    360
gttgacagga gcccagacgc ttttccaac ggcaactttt atataaaatg gcaatgtatt      420
catgcaattg cggccgtgtc aggttggaga cactggacca cactctccat tgcttcctga    480
ggagatggat cattgctagt gcatctacgc gcagcaatcc cgcaagctcg acaaccgtag    540
atgggctttg gtgggccaat caattacgca acccgcacgt taaattgtat gaggaaggaa    600
ggccacggta caaagtgggt ggtcttcacc cagtggttgt tggtggcgtc atgcagacca    660
tgcattgggg atagcacagg gttggggtgt cttgtggact caatgggtga aggagatgg    720 aaaagggcgg tgaaaagtgg tagaatcgaa atccctgacg tcaatttata aagtaaaatg    780
cgtttctgcc attttgctcc cctccttctt tcgcaatcgc ctcccaaaa gttgtcgtgg      840 cagtacacat gcttgcatac aatgaagcta atccggcttg ctcagtagtt gctatatcca    900
ggcatggtgt gaaaccctc aaagtatata taggagcggt gagccccagt ctggggtctt     960
ttctctccat ctcaaaacta ctttctcaca tgctagccac aaaa                     1004
```

<210> SEQ ID NO 5
<211> LENGTH: 1422
<212> TYPE: DNA
<213> ORGANISM: Yarrowia lipolytica

<400> SEQUENCE: 5

```
atttcttgtg tgtgcggcaa acgtagcaat tgcaactgca taaacgatga ttgtaaaagt      60
```

-continued

| | |
|---|---|
| atcacactt gctcagacag gttagattca cctggtacga gggcagtgtc ttaaaggttc | 120 |
| catctacctc ggcccttgtt tcttgaagag tggtcaatat gtgttttata cagctgaaat | 180 |
| ttccctgta tgttgagatc gtgtatattg gtcataatct gggctcttta gtcgatccca | 240 |
| gttttctcgg gcaagttttt ttctccacaa agtaccgctg gaaaactcta tgtgacttgt | 300 |
| tgacagatta cttgggttat ctgcgggata tgtcttggat aggcaaccgg gcatatatca | 360 |
| ccgggcggac tgttggttct gtacgtacat acagcacttt gagctcatgt ctcacacgca | 420 |
| accatggtgc gtggaggctt tggcatcctt tctacttgta gtggctatag tacttgcagt | 480 |
| ccaagcaaac atgagtatgt gcttgtatgt actgaaaccc gtctacggta atattttaga | 540 |
| gtgtggaact atgggatgag tgctcattcg atactatgtt gtcacccgat tgccgtttg | 600 |
| cgaggtaaga cacattcggt ggttcaggcg gctacttgta tgtagcatcc acgttcatgt | 660 |
| tttgtggatc agattaatgg tatggatatg cacggggcgt ttccccggta acgtgtaggc | 720 |
| agtccagtgc aacccagaca gctgagctct ctatagccgt gcgtgtgcgg tcatatcacg | 780 |
| ctacacttag ctacagaata aagctcggta gcgccaacag cgttgacaaa tagctcaagg | 840 |
| gcgtggagca cagggtttag gaggttttaa tgggcgagaa ggcgcgtaga tgtagtcttc | 900 |
| ctcggtccca tcggtaatca cgtgtgtgcc gatttgcaag acgaaaagcc acgagaataa | 960 |
| accgggagag gggatggaag tccccgaaca gcaaccagcc cttgccctcg tggacataac | 1020 |
| cttcacttg ccagaactct aagcgtcacc acggtataca agcgcacgta gaagattgtg | 1080 |
| gaagtcgtgt tggagactgt tgatttgggc ggtggagggg ggtatttgag agcaagtttg | 1140 |
| agatttgtgc cattgagggg gaggttattg tggccatgca gtcggatttg ccgtcacggg | 1200 |
| accgcaacat gcttttcatt gcagtccttc aactatccat ctcacctccc ccaatggctt | 1260 |
| ttaactttcg aatgacgaaa gcaccccct ttgtacagat gactatttgg gaccaatcca | 1320 |
| atagcgcaat tgggtttgca tcatgtataa aaggagcaat cccccactag ttataaagtc | 1380 |
| acaagtatct cagtataccc gtctaaccac acatttatca cc | 1422 |

<210> SEQ ID NO 6
<211> LENGTH: 865
<212> TYPE: DNA
<213> ORGANISM: Yarrowia lipolytica

<400> SEQUENCE: 6

| | |
|---|---|
| atgctcactt tgttgtcct gatgatctcc cgttatttcg ccgctcctct ggaaaccatc | 60 |
| cgcccgcaaa tcccctctgc ccatcttgac aatgcacaat gcatcattct cagcctgcat | 120 |
| gaatgcgaaa gatggcaata ttggtggagg aggcgacggc ggtaaacaat ggagatagag | 180 |
| accacaaaag agacctggag acccaaaatg gactcacgac aactccccca ctcccccact | 240 |
| ccccatctcc ccctgggcat cagttgccca tcggtatctc aactgtcgca ctagttagcg | 300 |
| caaccatcac atactttaga cgccaaacaa tgggacaact catcgcgccg aactatgggc | 360 |
| agattttaac tcgcacaaca ttaccccaac tctaaaaggt aacctcgacc ggaaaacggg | 420 |
| aagacaggat cagcaaccgt gatcgacaga atcttcaggg cactacagtt gatagacata | 480 |
| ggttatgttg gtaggtctag acgggcctcg ggaattgac cccaccagtt gcaagtcacg | 540 |
| tgccctgat acagctagtt tagcacatct gcccactacg tctggacgca ccatggtggt | 600 |
| gccagtcgcg tgaactcaaa cacccactag cctcgggaag gattcagtta aatccgcacc | 660 |
| ttatttccaa cacaaagaag cggttggcgg acaaagaaca tgtcctttct ggggcactgt | 720 |
| acattccagg actctgttca aggtcaaata tacaaaacac agatagagaa acatagacag | 780 |

```
ctgcggcctt ataaatacct gggcgcactt ctctcttttt ccctcctcat cacacattcg    840
ttcaccacta agtcactcgt tcaaa                                          865

<210> SEQ ID NO 7
<211> LENGTH: 880
<212> TYPE: DNA
<213> ORGANISM: Yarrowia lipolytica

<400> SEQUENCE: 7
aaacaaaaga gctgaaatca tatccttcag tagtagtata gtcctgttat cacagcatca     60 attaccccg tccaagtaag ttgattggga tttttgttta cagatacagt aatatacttg    120
actatttctt tacaggtgac tcagaaagtg catgttggaa atgagccaca gaccaagaca    180
agatatgaca aaattgcact attcgatgca gaattcgacg tgtttccat tggtgttatg     240 acattcatct gcattcatac aaaaaagtct tggtagtggt acttttgcgt tattacctcc    300
gatatctacg caccccccaa ccccctgct acagtaaaga gtgtgagtct actgtacatg     360
cttactaaac caccctactgt acagcgaaac ccctcagcaa atcacacaa tcagctcatt    420 acaacacacc caatgacctc accacaaatt ctatacgcct tttgacgcca ttattacagt    480
agcttgcaac gccgttgtct taggttccat ttttagtgct ctattacctc acttaacccg    540
tataggcaga tcaggccatg gcactaagtg tagagctaga ggttgatatc gccacgagtg    600
ctccatcagg gctagggtgg ggttagaaat acagtccgtg cgcactcaaa aggcgtccgg    660
gttagggcat ccgataatat cgcctggact cggcgccata ttctcgactt ctgggcgcgt    720
tgtattcatc cctccgctt cccaacactt ccaccgtttt ctccatccca accaatagaa     780
tagggtaacc ttattcggga cactttcgtc atacatagtc agatatacaa gcaatgtcac    840
tctccttcgt actcgtacat acaacacaac tacattcaaa                          880

<210> SEQ ID NO 8
<211> LENGTH: 1000
<212> TYPE: DNA
<213> ORGANISM: Yarrowia lipolytica

<400> SEQUENCE: 8
caattcatgt atcgtgtcaa ttcatgtatc gtgtcaattc atgtatcgtg tcaatactta     60
tatctcaagt ggttgcatcg caaacagcca tcgcatactc cactctactc tcactgagtt    120
cactcttacc cggctccacc ttctagaagc caccaccgat ccaccgacga tgatcagtcc    180
accacttgct ctgaatgtgc gttggagctg caccatgatt gatgacgtca ccgccattca    240
gatagggcaa aagacgagcg ccaatcgcaa caatgggcga gtgtcgacga ctcccccgct    300
ctctgcggtt tcagcgactc caaccgtcgc caaaagaccg tcattttcgt ctaaagcgca    360
gcccagccca tctcttctaa aagattccag aaagataggg ttcaccaact acgcaccaat    420
atgtacagta tcgtagctac tccggcttgg ctgatctgag agatagagat ggctccgaaa    480
cgcggaaaac ggcggggtcg gaccgatcac gtgacacgta ctcatccgtc gcgccccgag    540
cgccatttca acaccaaata ctcccggtca cgtgccaccc cgcccgctct acccacgaga    600
tgtttctaca ctatacactg ccacgccgtc atacctgcag ctaggttaac attcgattaa    660
ttagtggagt caccagtgta caggactatg gcggaaaccg ggttacacaa accggcccgg    720
aatagcagca ttataccgct ggacgagatc accgtcaata aattgcgtcg ttactcggga    780
caaccattgc tcctccggct acacctgctc aaaggacttg ttccacactc ttccccagct    840
```

```
ctcccacgca aacaaagaga gcaaccttaa gtggacagct catgagcact cccctcgttt      900
gctgcccacg ctcgattata taaagaccag cggatcccct tctatttgga cttgcatcaa      960
ccaaccacaa cccacaccaa gcacacaaag cacaagaaca                            1000
```

```
<210> SEQ ID NO 9
<211> LENGTH: 127
<212> TYPE: DNA
<213> ORGANISM: Yarrowia lipolytica

<400> SEQUENCE: 9
aattaacaga tagtttgccg gtgataattc tcttaacctc ccacactcct ttgacataac       60
gatttatgta acgaaactga aatttgacca gatattgttg taaatagaaa atctggcttg      120
taggtgg                                                                127
```

```
<210> SEQ ID NO 10
<211> LENGTH: 200
<212> TYPE: DNA
<213> ORGANISM: Yarrowia lipolytica

<400> SEQUENCE: 10 gtttttgat caatgatcca atggctttca cataccccc cacgcctata attaaaacac        60
agagaaatat aatctaactt aataaatatt acggagaatc tttcgagtgt tcagcagaaa      120
tatagccatt gtaacaaaag ccggctatcg accgctttat cgaagaatat ttcccgcccc      180
ccagtggcca aacgatatcg                                                  200
```

```
<210> SEQ ID NO 11
<211> LENGTH: 200
<212> TYPE: DNA
<213> ORGANISM: Yarrowia lipolytica

<400> SEQUENCE: 11
ctatccgaag atcaagagcg aagcaagttg taagtccagg acatgtttcc cgcccacgcg       60
agtgatttat aacacctctc ttttttgaca cccgctcgcc ttgaaattca tgtcacataa      120
attatagtca acgacgtttg aataacttgt cttgtagttc gatgatgatc atatgattac      180
attaatagta attactgtat                                                  200
```

```
<210> SEQ ID NO 12
<211> LENGTH: 200
<212> TYPE: DNA
<213> ORGANISM: Yarrowia lipolytica

<400> SEQUENCE: 12
acttcgagct aatccagtag cttacgttac ccaggggcag gtcaactggc tagccacgag       60
tctgtcccag gtcgcaattt agtgtaataa acaatatata tattgagtct aaagggaatt      120
gtagctattg tgattgtgtg attttcgtct tgctggttct tattgtgtcc cattcgtttc      180
atcctgatga ggacccctgg                                                  200
```

```
<210> SEQ ID NO 13
<211> LENGTH: 200
<212> TYPE: DNA
<213> ORGANISM: Yarrowia lipolytica

<400> SEQUENCE: 13
gctatttaca gcatgtgtaa tgaggaatat aacgttgatt gaattgtttg tgaaaaatgt       60
agaaaatttc agtgaagttg tgttttctat atagtaagca cttttggtac aagtatctgc      120
```
acatccctgc atgttacaag cctgatcatg cagggcaata ttctgactat aaatataccT    180
cgatattttA gcaagctata                                                200

<210> SEQ ID NO 14
<211> LENGTH: 300
<212> TYPE: DNA
<213> ORGANISM: Yarrowia lipolytica

<400> SEQUENCE: 14
atgtggtgat tgctgttgtg caagcctttg ctcgttttct gctgtatgta atttaaagaa    60
cgattgtatg aatcgaagtc aaggtgagtg tagtttgaga agtgtaaccc cagtgtcata    120
gctgtgtact ccattcattg aagggtgtag tcgtgtttta ttgcatgagc gcctattact    180
cgtataagta actgttttgt aacacttcat gaacggagat ggtatgaaca gaagtaataa    240
tatcctggaa gtcagctgtg cccagaggtg tgtgtgggtg tggcatactt tgggacaaca    300

<210> SEQ ID NO 15
<211> LENGTH: 1503
<212> TYPE: DNA
<213> ORGANISM: Artificial sequence
<220> FEATURE:
<223> OTHER INFORMATION: tHMG CpO for Yarrowia lipolitica

<400> SEQUENCE: 15
atgacccagt ctgtgaaggt ggttgagaag cacgttccta tcgtcattga gaagcccagc    60
gagaaggagg aggacaccTc ttctgaagac tccattgagc tgactgtcgg aaagcagccc    120
aagcccgtga ccgagacccg ttctctggac gacttggagg ctatcatgaa ggcaggtaag    180
accaagctcc tggaggacca cgaggttgtc aagctctctc tcgaaggcaa gctccctttg    240
tatgctcttg agaagcagct tggtgacaac acccgagctg ttggcatccg acgatctatc    300
atctcccagc agtctaatac caagactctt gagacctcaa agctccctta cctgcactac    360
gactacgacc gtgttttTgg agcctgttgc gagaacgtta ttggttacat gcctctcccc    420
gttggtgttg ctggccccat gaacattgat ggcaagaact accacattcc tatgccacc    480 actgagggtt gtcttgttgc ctcaaccatg cgaggttgca aggccatcaa cgccggtggc    540
ggtgttacca ctgtgcttac tcaggacggt atgacacgag gtccttgtgt tccttccccc    600
tctctcaagc gggctggagc cgctaagatc tggcttgatt ccgaggaggg tctcaagtcc    660
atgcgaaagg ccttcaactc cacctctcga tttgctcgtc tccagtctct tcactctacc    720
cttgctggta acctgctgtt tattcgattc cgaaccacca ctggtgatgc catgggcatg    780
aacatgatct ccaagggcgt cgaacactct ctggccgtca tggtcaagga gtacggcttc    840
cctgatatgg acattgtgtc tgtctcgggt aactactgca ctgacaagaa gcccgcagcg    900
atcaactgga tcgaaggccg aggcaagagt gttgttgccg aagccaccat ccctgctcac    960
attgtcaagt ctgttctcaa aagtgaggtt gacgctcttg ttgagctcaa catcagcaag    1020
aatctgatcg gtagtgccat ggctggctct gtgggaggtt tcaatgcaca cgccgcaaac    1080
ctggtgaccg ccatctacct tgccactggc caggatcctg ctcagaatgt cgagtcttcc    1140
aactgcatca cgctgatgag caacgtcgac ggtaacctgc tcatctccgt tccatgcct    1200 tctatcgagg tcggtaccat tggtggaggt actatttTgg agccccaggg tgctatgctg    1260
gagatgcttg gcgtgcgagg tcctcacatc gagacccccg tgccaacgc caacagctt    1320 gctcgcatca ttgcttctgg agttcttgca gcggagcttt cgctgtgttc tgctcttgct    1380

| | |
|---|---|
| gccggccatc ttgtgcaaag tcatatgacc cacaaccgtt cccaggctcc tactccggcc | 1440 |
| aagcagtctc aggccgatct gcagcgtctc caaaacggtt cgaatatctg cattcggtca | 1500 |
| tag | 1503 |

<210> SEQ ID NO 16
<211> LENGTH: 984
<212> TYPE: DNA
<213> ORGANISM: Artificial sequence
<220> FEATURE:
<223> OTHER INFORMATION: GGS CpO for Yarrowia lipolitica

<400> SEQUENCE: 16

| | |
|---|---|
| atggattata acagcgcgga tttcaaggag atctggggca aggccgccga caccgcgctg | 60 |
| ctgggaccgt acaactacct cgccaacaac cggggccaca acatcagaga acacttgatc | 120 |
| gcagcgttcg gagcggttat caaggtggac aagagcgatc tcgaaaccat ttcgcacatc | 180 |
| accaagattt tgcataactc gtcgctgctt gttgatgacg tggaagacaa ctcgatgctc | 240 |
| cgacgaggcc tgccggcagc ccattgtctg tttggagtcc cccaaaccat caactccgcc | 300 |
| aactacatgt actttgtggc tctgcaggag gtgctcaagc tcaagtctta tgatgccgtc | 360 |
| tccattttca ccgaggaaat gatcaacttg catagaggtc agggtatgga tctctactgg | 420 |
| agagaaacac tcacttgccc ctcggaagac gagtatctgg agatggtggt gcacaagacc | 480 |
| ggaggactgt ttcggctggc tctgagactt atgctgtcgg tggcatcgaa acaggaggac | 540 |
| catgaaaaga tcaactttga tctcacacac cttaccgaca cactgggagt catttaccag | 600 |
| attctggatg attacctcaa cctgcagtcc acggaattga ccgagaacaa gggattctgc | 660 |
| gaagatatca gcgaaggaaa gttttcgttt ccgctgattc acagcatccg gaccaacccg | 720 |
| gataaccacg agattctcaa cattctcaaa cagcgaacaa gcgacgcttc actcaaaaag | 780 |
| tacgccgtgg actacatgag aacagaaacc aagagtttcg actactgcct caagagaatc | 840 |
| caggccatgt cactcaaggc aagttcgtac attgatgatc tcgcagcagc cggccacgat | 900 |
| gtctccaagt tgcgagccat tttgcattat tttgtgtcca cctctgactg tgaggagaga | 960 |
| aagtactttg aggatgcgca gtga | 984 |

<210> SEQ ID NO 17
<211> LENGTH: 1446
<212> TYPE: DNA
<213> ORGANISM: Artificial sequence
<220> FEATURE:
<223> OTHER INFORMATION: UGT1 CpO for Yarrowia lipolitica

<400> SEQUENCE: 17

| | |
|---|---|
| atggacgcca tggccaccac cgagaagaag ccccacgtca tcttcatccc cttccccgcc | 60 |
| cagtcccaca tcaaggccat gctcaagctc gcccagctcc tccaccacaa gggcctccag | 120 |
| atcacctttg tcaacaccga cttcatccac aaccagttcc tcgagtcctc cggccccac | 180 |
| tgtctggacg gtgctcccgg tttccgattt gagactatcc ccgatggtgt ctcccactcc | 240 |
| cccgaggcct ccatccccat ccgagagtct ctgctccgat ccattgagac taacttcctc | 300 |
| gaccgattca ttgatctcgt caccaagctc cccgatcctc ccacctgtat catctccgac | 360 |
| ggtttcctgt ccgttttcac cattgatgct gccaagaagc tcggtatccc cgtcatgatg | 420 |
| tactggactc tggctgcctg tggtttcatg ggtttctacc acatccactc tctgatcgag | 480 |
| aagggctttc tcctctcaa ggacgcctcc tacctcacca acgttacct cgacaccgtc | 540 |
| attgactggg tccccggtat ggagggtatc cgactcaagg acttccccct cgactggtcc | 600 |

-continued

```
accgacctca acgacaaggt tctcatgttc accaccgagg ctccccagcg atcccacaag    660
gtttcccacc acatcttcca caccttcgac gagctcgagc cctccatcat caagactctg    720
tctctgcgat acaaccacat ctacaccatt ggcccctcc agctcctcct cgaccagatc     780
cccgaggaga agaagcagac cggtatcacc tctctgcacg gctactctct cgtcaaggaa    840
gagcccgagt gcttccagtg gctccagtcc aaggagccca actccgttgt ctacgtcaac    900
tttggctcca ccaccgtcat gtctctcgag gacatgaccg agtttggctg ggtctggcc     960 aactccaacc actacttcct gtggatcatc cgatccaacc tcgtcattgg cgagaacgcc   1020
gttctgcctc ccgagctcga ggagcacatc aagaagcgag gcttcattgc ctcttggtgc   1080
tcccaggaga aggttctcaa gcacccctcc gtcggtggtt cctgaccca ctgcggctgg    1140 ggctccacca ttgagtctct gtccgctggt gtccccatga tctgctggcc ctactcctgg   1200
gaccagctca ccaactgccg atacatctgc aaggagtggg aggttggtct ggagatgggt   1260
accaaggtca gcgagatga ggtcaagcga ctcgtccagg agctcatggg cgagggtggt    1320
cacaagatgc gaaacaaggc caaggactgg aaggagaagg cccgaattgc cattgccccc   1380
aacggctctt cttctctcaa cattgacaag atggtcaagg agatcactgt tctcgctcga   1440
aactaa                                                              1446
```

<210> SEQ ID NO 18
<211> LENGTH: 1383
<212> TYPE: DNA
<213> ORGANISM: Artificial sequence
<220> FEATURE:
<223> OTHER INFORMATION: UGT3 CpO for Yarrowia lipolitica

<400> SEQUENCE: 18

```
atggccgagc agcagaagat caagaagtct ccccacgttc tgctcatccc cttccctctg     60
cagggccaca tcaaccccct catccagttc ggcaagcgac tcatctccaa gggtgtcaag    120
accactctgg tcaccaccat ccacaccctc aactccactc tcaaccactc caacaccacc    180
accacctcca tcgagatcca ggccatctcc gacggctgtg acgagggtgg tttcatgtct    240
gctggtgagt cttacctcga gactttcaag caggtcggtt ccaagtctct ggctgaccte    300 atcaagaagc tccagtccga gggtaccacc attgacgcca tcatctacga ctccatgacc    360
gagtgggttc tcgatgtcgc catcgagttt ggtattgacg tggctccctt cttcacccag    420
gcctgtgtcg tcaactctct ctactaccac gtccacaagg tctgatctc tctgcccctc    480 ggcgagactg tctccgtccc cggtttcccc gttctgcagc gatgggagac tcctctcatt    540
ctccagaacc acgagcagat ccagtccccc tggtcccaga tgctcttcgg ccagttcgcc    600
aacattgacc aggcccgatg ggttttcacc aactccttct acaagctcga ggaagaggtc    660
attgagtgga cccgaaagat ctggaacctc aaggtcattg gccccacccct ccctccatg    720 tacctcgaca gcgactcga tgacgacaag gacaacggtt caacctcta caaggccaac    780 caccacgagt gcatgaactg gctcgacgac aagcccaagg agtccgttgt ctacgttgcc    840
tttggctctc tggtcaagca cggccccgag caggttgagg agatcacccg agctctgatt    900
gactccgatg tcaacttcct gtgggtcatc aagcacaagg aagagggtaa gctccccgag    960
aacctgtccg aggtcatcaa gaccggcaag ggcctcattg ttgcctggtg caagcagctc   1020
gacgttctcg cccacgagtc cgtcggctgc tttgtcaccc actgcggttt caactccacc   1080
ctcgaggcta tctctctcgg tgtccccgtt gttgccatgc cccagttctc cgaccagacc   1140
```

| accaacgcca agctcctcga tgagattctc ggtgtcggtg tccgagtcaa ggctgacgag | 1200 |
| aacggtattg tccgacgagg taacctggct tcttgtatca agatgatcat ggaggaagag | 1260 |
| cgaggtgtca tcatccgaaa gaacgccgtc aagtggaagg atctggccaa ggttgctgtc | 1320 |
| cacgagggtg gctcttccga caacgacatt gtcgagtttg tctccgagct catcaaggcc | 1380 |
| taa | 1383 |

<210> SEQ ID NO 19
<211> LENGTH: 1377
<212> TYPE: DNA
<213> ORGANISM: Artificial sequence
<220> FEATURE:
<223> OTHER INFORMATION: UGT4 CpO for Yarrowia lipolitica

<400> SEQUENCE: 19

| atggagaaca agaccgagac taccgtccga cgacgacgac gaatcattct cttcccgtc | 60 |
| cccttccagg ccacatcaa ccccattctg cagctcgcca acgttctgta ctccaagggc | 120 |
| ttctccatca ccatcttcca caccaacttc aacaagccca agacctccaa ctaccccac | 180 |
| ttcactttcc gattcatcct cgacaacgac ccccaggacg agcgaatctc caacctgccc | 240 |
| acccacggtc tctggctgg tatgcgaatc cccatcatca cgagcacgg tgctgacgag | 300 |
| ctccgacgag agctcgagct gctcatgctc gcctccgaag aggacgagga agtctcctgt | 360 |
| ctgatcaccg atgctctgtg gtactttgcc cagtccgtcg ccgactctct caacctgcga | 420 |
| cgactcgttc tcatgacctc ctctctgttc aacttccacg cccacgtttc tctgccccag | 480 |
| tttgacgagc tcggttacct cgaccccgat gacaagaccc gactcgagga gcaggcttcc | 540 |
| ggtttcccca tgctcaaggt caaggacatc aagtccgcct actccaactg cagattctc | 600 |
| aaggagattc tcggcaagat gatcaagcag accaaggcct cctccggtgt catctggaac | 660 |
| tccttcaagg agctcgagga gtccgagctc gagactgtca tccgagagat ccccgctccc | 720 |
| tctttcctca tccccctgcc caagcacctc accgcttcct cctcttctct gctcgaccac | 780 |
| gaccgaaccg tctttcagtg gctcgaccag cagcccccct tcctccgtcct ctacgtttcc | 840 |
| ttcggctcca cctccgaggt cgacgagaag gacttcctcg agattgctcg aggcctcgtt | 900 |
| gactccaagc agtccttcct gtgggttgtc cgacccggct tgtcaaggg ctccacctgg | 960 |
| gttgagcccc tgcccgatgg ttttcctcggt gagcgaggcc gaattgtcaa gtgggtcccc | 1020 |
| cagcaggaag ttctggccca cggtgccatt ggtgccttct ggacccactc cggctggaac | 1080 |
| tccactctcg agtccgtctg cgagggtgtc cccatgatct ctccgactt ggcctcgac | 1140 |
| cagcccctca cgcccgata catgtccgat gttctcaagg tcggtgtcta cctcgagaac | 1200 |
| ggctgggagc gaggtgagat tgccaacgcc atccgacgag tcatggtcga cgaggaaggt | 1260 |
| gagtacatcc gacagaacgc ccgagtcctc aagcagaagg ccgatgtctc tctcatgaag | 1320 |
| ggtggttctt cttacgagtc tctcgagtct ctcgtttcct acatctcttc tttgtaa | 1377 |

<210> SEQ ID NO 20
<211> LENGTH: 2232
<212> TYPE: DNA
<213> ORGANISM: Artificial sequence
<220> FEATURE:
<223> OTHER INFORMATION: tCPS_SR CpO for Yarrowia lipolitica

<400> SEQUENCE: 20

| atgtgcaagc tgtttccaa ggagtactcc gatctgctcc agaaggacga ggcctctttc | 60 |
| accaagtggg acgacgacaa ggtcaaggac caccctcgaca ccaacaagaa cctctacccc | 120 |

```
aacgacgaga tcaaggagtt tgtcgagtcc gtcaaggcca tgttcggctc catgaacgac     180
ggcgagatta atgtctctgc ttacgacacc gcctgggttg ctctggtcca ggatgtcgac     240
ggttccggct ctcctcagtt cccttcctct ctcgagtgga tcgccaacaa ccagctgtcc     300
gacggttctt ggggtgacca cctgctcttc tctgctcacg accgaatcat caacaccctg     360
gcctgtgtca ttgctctgac ctcttggaac gtccacccct ccaagtgcga agggtctg      420
aacttcctcc gagagaacat ctgcaagctc gaggacgaga cgccgagca catgcccatt      480
ggcttcgagg tcaccttccc ctctctgatt gacattgcca agaagctcaa cattgaggtc     540
cccgaggaca cccccgctct caaggagatc tacgctcgac gagacatcaa gctcaccaag     600
atccccatgg aggttctcca aggtcccc accactctcc tccactctct cgagggtatg      660
cccgatctcg agtgggagaa gctgctcaag ctgcagtgca aggacggctc tttcctcttc     720
tcccctctt ccactgcctt cgccctcatg cagaccaagg acgagaagtg tctccagtac      780
ctcaccaaca ttgtcaccaa gttcaacggt ggtgtcccca acgtctaccc cgttgacctc     840
tttgagcaca tctgggttgt tgaccgactc cagcgactcg gtatcgcccg atacttcaag     900
tccgagatca aggactgtgt cgagtacatc aacaagtact ggaccaagaa cggtatctgc     960
tgggcccgaa acacccacgt ccaggacatt gacgacaccg ccatgggctt ccgagttctg    1020
cgagcccacg gctacgatgt cacccccgat gtctttcgac agtttgagaa ggacggcaag    1080
tttgtctgtt tcgccggtca gtccacccag gccgtcaccg gtatgttcaa cgtctaccga    1140
gcttctcaga tgctcttccc cggtgagcga atcctgagg acgccaagaa gttctcctac     1200
aactacctca aggagaagca gtccaccaac gagctgctcg acaagtggat cattgccaag    1260
gatctgcccg gtgaggttgg ctacgccctc gacatcccct ggtacgcctc tctgccccga    1320
ctggagactc gatactacct cgagcagtac ggtggtgagg acgatgtctg gatcggtaag    1380
accctgtacc gaatgggcta cgtttccaac aacacctacc tcgagatggc caagctcgac    1440
tacaacaact acgttgccgt cctccagctc gagtggtaca ccatccagca gtggtacgtc    1500
gacattggta tcgagaagtt cgagtccgac aacatcaagt ccgtccttgt ctcctactac    1560
ctcgctgctg cctccatctt cgagcccgag cgatccaagg agcgaattgc ctgggccaag    1620
accaccatcc tcgtcgacaa gatcacctcc atcttcgact cctcccagtc ctccaaggaa    1680
gatatcaccg ccttcattga caagttccga acaagtcct cctccaagaa gcactccatc    1740
aacggcgagc cctggcacga ggtcatggtt gctctcaaga aaactctcca cggctttgcc    1800
ctcgacgctc tgatgaccca ctctcaggac atccacccc agctccacca ggcctgggag    1860
atgtggctca ccaagctcca ggacggtgtt gatgtcactg ctgagctcat ggtccagatg    1920
atcaacatga ccgccggccg atgggtttcc aaggagctcc tcacccaccc ccagtaccag    1980
cgactctcca ctgtcaccaa ctctgtctgc cacgacatca ccaagctcca caacttcaag    2040
gagaactcca ccaccgtcga ctccaaggtc caggagctgg tccagctcgt tttctccgac    2100
accccccgatg atctcgacca ggacatgaag cagaccttcc tgactgtcat gaaaactttc    2160
tactacaagg cctggtgcga ccccaacacc atcaacgacc acatctccaa ggtctttgag    2220
attgtgattt aa                                                        2232
```

<210> SEQ ID NO 21
<211> LENGTH: 2274
<212> TYPE: DNA
<213> ORGANISM: Artificial sequence
<220> FEATURE:

<223> OTHER INFORMATION: tKS-SR CpO for Yarrowia lipolitica

<400> SEQUENCE: 21

```
atgacctccc acggcggcca gaccaacccc accaacctca tcattgacac caccaaggag      60
cgaatccaga agcagttcaa gaacgtcgag atctccgttt cctcctacga caccgcctgg     120
gtcgccatgg tccctctcc caactccccc aagtctccct gcttccccga gtgtctcaac     180
tggctcatca caaccagct caacgacggc tcttggggtc tggtcaacca cacccacaac     240
cacaaccacc cctcctcaa ggactctctc tcttccactc tcgcctgcat tgttgctctc     300
aagcgatgga acgttggcga ggaccagatc aacaagggtc tgtctttcat tgagtccaac     360
ctcgcctccg ccaccgagaa gtcccagccc tcccccattg ctttgatat catcttcccc     420
ggtctgctcg agtacgccaa gaacctcgat atcaacctgc tctccaagca gaccgacttc     480
tctctcatgc tgcacaagcg agagctcgag cagaagcgat gccactccaa cgagatggac     540
ggctacctgg cctacatttc cgagggtctg ggtaacctct acgactggaa catggtcaag     600
aagtaccaga tgaagaacgg ttccgttttc aactccccct ctgccaccgc tgctgccttc     660
atcaaccacc agaaccccgg ctgtctcaac tacctcaact ctctgctcga caagtttggt     720
aacgccgtcc ccactgtcta cccccacgat ctcttcatcc gactctccat ggtcgacacc     780
attgagcgac tcggtatttc ccaccacttc cgagtcgaga tcaagaacgt tctcgatgag     840
acttaccgat gctgggttga gcgagatgag cagatcttca tggacgttgt cacctgtgct     900
ctggccttcc gactcctccg aatcaacggt tacgaggttt cccccgaccc cctcgccgag     960
atcaccaacg agctggctct caaggacgag tacgccgccc tcgagactta ccacgcttct    1020
cacattctgt accaagagga tctgtcctcc ggcaagcaga ttctcaagtc cgccgacttc    1080
ctcaaggaga tcatctccac tgactccaac cgactctcca gctcatcca caaggaagtc    1140
gagaacgctc tcaagttccc catcaacacc ggtctggagc gaatcaacac ccgacgaaac    1200
atccagctct acaacgtcga caacacccga attctcaaga ccacctacca ctcttccaac    1260
atctccaaca ccgactacct gcgactcgcc gtcgaggact tctacacctg ccagtccatc    1320
taccgagagg agctcaaggg tctggagcga tgggttgtcg agaacaagct cgaccagctc    1380
aagtttgccc gacaaaagac tgcctactgc tacttctccg ttgctgccac cctctcttct    1440
cccgagctct ccgacgcccg aatctcttgg gccaagaacg gtatcctgac cactgttgtc    1500
gacgacttct ttgacattgg tggcaccatt gacgagctga ccaacctcat ccagtgcgtc    1560
gagaagtgga acgtcgacgt tgacaaggac tgttgttccg agcacgtccg aatcctcttc    1620
ctggctctca aggacgccat ctgctggatc ggtgacgagg ccttcaagtg gcaggctcga    1680
gatgtcactt cccacgtcat ccagacctgg ctcgagctca tgaactccat gctgcgagag    1740
gccatctgga cccgagatgc ctacgtcccc accctcaacg agtacatgga gaacgcctac    1800
gtcagctttg ctctcggtcc cattgtcaag cccgccatct actttgtcgg tcccaagctg    1860
tccgaggaga ttgtcgagtc ctccgagtac cacaacctct tcaagctcat gtccacccag    1920
ggccgactcc tcaacgatat ccactccttc aagcgagagt tcaaggaagg taagctcaac    1980
gccgttgctc tgcacctgtc caacggtgag tccggcaagg tcgaggaaga ggtcgtcgag    2040
gagatgatga tgatgatcaa gaacaagcga aaggagctca tgaagctcat cttcgaggag    2100
aacggctcca ttgtccccg agcctgcaag gacgccttct ggaacatgtg ccacgtcctc    2160
aacttcttct acgccaacga cgacggtttc accggcaaca ccattctcga caccgtcaag    2220
gacatcatct acaaccctct ggttctggtc aacgagaacg aggagcagag gtaa          2274
```

<210> SEQ ID NO 22
<211> LENGTH: 1578
<212> TYPE: DNA
<213> ORGANISM: Artificial sequence
<220> FEATURE:
<223> OTHER INFORMATION: KAH_4 CpO for Yarrowia lipolitica

<400> SEQUENCE: 22

| | | | | | |
|---|---|---|---|---|---|
| atggagtctc | tggttgtcca | caccgtcaac | gccatctggt | gcattgtcat | tgtcggtatc | 60 |
| ttctccgtcg | gctaccacgt | ctacggccga | gctgttgtcg | agcagtggcg | aatgcgacga | 120 |
| tctctcaagc | tccagggtgt | caagggtcct | cctcctcca | tcttcaacgg | taacgtttcc | 180 |
| gagatgcagc | gaatccagtc | cgaggccaag | cactgctccg | gtgacaacat | catctcccac | 240 |
| gactactctt | cttctctgtt | ccccactttt | gaccactggc | gaaagcagta | cggccgaatc | 300 |
| tacacctact | ccactggcct | caagcagcac | ctctacatca | accaccccga | gatggtcaag | 360 |
| gagctctccc | agaccaacac | cctcaacctc | ggccgaatca | cccacatcac | caagcgactc | 420 |
| aaccccattc | tcggtaacgg | tatcatcacc | tccaacggcc | cccactgggc | ccaccagcga | 480 |
| cgaatcattg | cctacgagtt | cacccacgac | aagatcaagg | gtatggtcgg | tctgatggtc | 540 |
| gagtccgcca | tgcccatgct | caacaagtgg | gaggagatgg | tcaagcgagg | tggtgagatg | 600 |
| ggctgtgaca | tccgagtcga | cgaggacctc | aaggatgtct | ccgctgacgt | cattgccaag | 660 |
| gcctgtttcg | gctcttcctt | ctccaagggc | aaggccatct | tctccatgat | ccgagatctg | 720 |
| ctcaccgcca | tcaccaagcg | atccgtcctc | ttccgattca | acggtttcac | cgacatggtt | 780 |
| ttcggctcca | agaagcacgg | tgacgttgac | attgacgctc | tcgagatgga | gctcgagtcc | 840 |
| tccatctggg | agactgtcaa | ggagcgagag | attgagtgca | aggacaccca | caagaaggac | 900 |
| ctcatgcagc | tcattctcga | gggtgccatg | cgatcttgtg | acggtaacct | gtgggacaag | 960 |
| tctgcttacc | gacgattcgt | tgtcgacaac | tgcaagtcca | tctactttgc | cggccacgac | 1020 |
| tccaccgccg | tttccgtttc | ttggtgcctc | atgctgctcg | ctctcaaccc | ctcttggcag | 1080 |
| gtcaagatcc | gagatgagat | tctgtcctcc | tgcaagaacg | gtatccccga | cgccgagtcc | 1140 |
| atccccaacc | tcaagaccgt | caccatggtc | atccaggaga | ctatgcgact | ctaccctccc | 1200 |
| gctcccattg | tcggccgaga | ggcctccaag | gacattcgac | tcggtgatct | ggttgtcccc | 1260 |
| aagggtgtct | gtatctggac | cctcatcccc | gctctgcacc | gagatcccga | gatctggggt | 1320 |
| cccgacgcca | acgacttcaa | gcccgagcga | ttctccgagg | gtatctccaa | ggcctgcaag | 1380 |
| taccccccagt | cctacatccc | ctttggcctc | ggccccgaa | cctgtgtcgg | caagaacttt | 1440 |
| ggtatgatgg | aggtcaaggt | cctcgtttct | ctgattgtct | ccaagttctc | cttcactctg | 1500 |
| tctcccacct | accagcactc | tccctcccac | aagctgctcg | tcgagcccca | gcacggtgtt | 1560 |
| gtcatccgag | ttgtataa | | | | | 1578 |

<210> SEQ ID NO 23
<211> LENGTH: 1578
<212> TYPE: DNA
<213> ORGANISM: Artificial sequence
<220> FEATURE:
<223> OTHER INFORMATION: KO_Gib CpO for Yarrowia lipolitica

<400> SEQUENCE: 23

| | | | | | |
|---|---|---|---|---|---|
| atgtccaagt | ccaactccat | gaactccacc | tcccacgaga | ctctcttcca | gcagctcgtt | 60 |
| ctcggcctcg | accgaatgcc | cctcatggac | gtccactggc | tcatctacgt | tgcctttggt | 120 |

```
gcctggctct gctcctacgt catccacgtt ctgtcctctt cctccactgt caaggtcccc    180
gtcgtcggtt accgatccgt tttcgagccc acctggctcc tccgactgcg attcgtctgg    240
gagggtggtt ccatcattgg ccagggctac aacaagttca aggactccat cttccaggtc    300
cgaaagctcg gtaccgacat tgtcatcatc cctcccaact acattgacga ggtccgaaag    360
ctctcccagg acaagacccg atccgtcgag cccttcatca cgactttgc cggccagtac     420 acccgaggta tggtctttct gcagtccgat ctccagaacc gagtcatcca gcagcgactc    480 accccccaagc ttgtctctct caccaaggtc atgaaggaag agctcgacta cgctctgacc   540
aaggagatgc ccgacatgaa gaacgacgag tgggttgagg tcgacatctc ttccatcatg    600
gtccgactca tctctcgaat ctccgcccga gttttcctcg gccccgagca ctgccgaaac    660
caggagtggc tcaccaccac cgccgagtac tccgagtctc tcttcatcac cggcttcatc    720
ctccgagttg tcccccacat tctccgaccc ttcattgctc ctctgctgcc ctcttaccga    780 acctgctgc gaaacgtttc ttccggccga cgagtcattg gtgatatcat ccgatcccag    840
cagggtgacg gtaacgagga catcctctct tggatgcgag atgctgccac tggtgaggag    900
aagcagatcg acaacattgc ccagcgaatg ctcattctgt ctctcgcctc catccacacc    960
accgccatga ccatgaccca cgccatgtac gatctgtgtg cctgccccga gtacattgag    1020
cccctccgag atgaggtcaa gtccgtcgtt ggtgcttctg gctgggacaa gaccgctctc    1080
aaccgattcc acaagctcga ctctttcctc aaggagtccc agcgattcaa ccccgttttc    1140
ctgctcacct caaccgaat ctaccaccag tccatgaccc tctccgatgg taccaacatc     1200
ccctccggta cccgaattgc tgtccctct cacgccatgc tccaggactc cgcccacgtc     1260
cccggtccca ctcctcccac tgagttcgac ggtttccgat actccaagat ccgatccgac    1320
tccaactacg cccagaagta cctcttctcc atgaccgact cttccaacat ggcctttggc    1380
tacggtaagt acgcctgccc cggccgattc tacgcctcca cgagatgaa gctgactctg     1440 gccattctgc cctccagtt tgagttcaag ctccccgacg taagggccg accccgaaac     1500 atcaccatcg actccgacat gatccccgac ccccgagctc gactctgtgt ccgaaagcga    1560
tctctgcgtg acgagtaa                                                   1578

<210> SEQ ID NO 24
<211> LENGTH: 2133
<212> TYPE: DNA
<213> ORGANISM: Artificial sequence
<220> FEATURE:
<223> OTHER INFORMATION: CPR_3 CpO for Yarrowia lipolitica

<400> SEQUENCE: 24
atgtcctcct cttcttcttc ttccaccctcc atgattgatc tcatggctgc catcatcaag    60
ggtgagcccg tcattgtctc cgaccccgcc aacgcctccg cctacgagtc cgttgctgcc    120
gagctgtcct ccatgctcat cgagaaccga cagtttgcca tgatcgtcac cacctccatt    180
gctgttctca ttggctgcat tgtcatgctc gtctggcgac atctggctc cggtaactcc    240 aagcgagtcg agcccctcaa gccctggtc atcaagcccc gagaagagga tcgacgac      300 ggccgaaaga aggtcaccat cttctttggc acccagaccg gtactgctga gggcttcgcc    360
aaggctctcg gtgaggaagc caaggctcga tacgaaaaga cccgattcaa gattgtcgac    420
ctcgatgatt acgctgccga tgacgacgag tacgaggaga gctcaagaa agaggacgtt    480 gccttcttct tcctgccac ctacggtgac ggtgagccca ccgacaacgc tgcccgattc    540
tacaagtggt tcaccgaggg taacgaccga ggcgagtggc tcaagaacct caagtacggt    600
```

```
gttttcggtc tgggcaaccg acagtacgag cacttcaaca aggttgccaa ggttgtcgac    660
gacatcctcg tcgagcaggg tgcccagcga ctcgtccagg tcggcctcgg tgatgatgac    720
cagtgcatcg aggacgactt cactgcctgg cgagaggctc tgtggcccga gctcgacacc    780
attctgcgag aggaaggtga caccgccgtt gccacccct acaccgccgc cgtcctcgag    840
taccgagtct ccatccacga ctccgaggat gccaagttca cgacatcaa catggccaac    900 ggtaacggct acaccgtctt tgacgcccag caccctaca aggccaacgt cgccgtcaag    960
cgagagctcc acaccccga gtccgaccga tcttgtatcc acctcgagtt tgacattgct   1020
ggttccggtc tgacctacga gactggtgac acgttggtg tcctctgtga caacctgtcc   1080
gagactgtcg acgaggctct gcgactcctc gacatgtccc ccgacactta cttctctctg   1140
cacgccgaga aagaggacgg tactcccatc tcttcttctc tgccccctcc cttccctccc   1200
tgcaacctgc gaaccgctct gacccgatac gcctgcctcc tctcttctcc caagaagtct   1260
gctctcgttg ctctggccgc ccacgcctcc gaccccaccg aggctgagcg actcaagcac   1320
ctcgcctctc ccgctggcaa ggacgagtac tccaagtggg ttgtcgagtc ccagcgatct   1380
ctgctcgagg tcatggccga gttccccctcc gccaagcccc ctctcggtgt tttcttcgcc   1440
ggtgttgctc cccgactcca gccccgattc tactccatct cctcttcccc caagatcgcc   1500
gagactcgaa tccacgttac ctgtgctctg gtctacgaga agatgcccac cggccgaatc   1560
cacaagggtg tctgctccac ctggatgaag aacgccgttc cctacgagaa gtccgagaac   1620
tgttcctctg ctcccatctt tgtccgacag tccaacttca agctccctc cgactccaag   1680 gtccccatca tcatgattgg ccccggtacc ggcctcgccc cttccgagg cttcctgcag   1740 gagcgactcg ccctcgtcga gtccggtgtc gagctcggcc cctccgtcct cttctttggc   1800
tgccgaaacc gacgaatgga cttcatctac gaagaggagc tccagcgatt cgtcgagtcc   1860
ggtgctctcg ccgagctctc cgttgccttc tcccgagagg gtcccaccaa ggagtacgtc   1920
cagcacaaga tgatggacaa ggcctccgac atctggaaca tgatctccca gggcgcctac   1980
ctctacgtct gcggtgacgc caagggtatg gcccgagatg tccaccgatc tctgcacacc   2040
attgcccagg agcagggctc catggactcc accaaggccg agggtttcgt caagaacctc   2100
cagacctccg gccgatacct ccgagatgtc tgg                              2133
```

<210> SEQ ID NO 25  
<211> LENGTH: 1419  
<212> TYPE: DNA  
<213> ORGANISM: Artificial sequence  
<220> FEATURE:  
<223> OTHER INFORMATION: UGT2_10b CpO for Y. lipolitica

<400> SEQUENCE: 25

```
atggccacct ccgactccat tgttgacgac cgaaagaagc tccacattgt catgttcccc     60
tggctcgcct ttggccacat catccctat ctcgagcttt ccaagctcat tgcccagaag    120
ggccacaagg tttccttcct ctccaccacc aagaacattg accgactctc ctcccacatc    180
tctcccctca tcaactttgt caagctcacc ctccccgag tccaggagct gcccgaggac    240
gccgaggcca ccactgatgt ccaccccgag gatatcccct acctcaagaa ggcctccgac    300
ggcctccagc ccgaggtcac tgagttcctc gagcagcact ctcccgactg gatcatctac    360
gactacaccc actactggct cccgagatt gccaagtctc tcggtgtctc tcgagccac    420 ttctccgtca ccacccctg ggccattgct tacatgggtc ccactgccga tgccatgatc    480
```

| | |
|---|---|
| aacggttccg actaccgaac cgagcttgag gacttcaccg tccctcccaa gtggttcccc | 540 |
| ttccccacca ccgtctgctg gcgaaagcac gatctggccc gactcgtccc ctacaaggct | 600 |
| cccggtatct ccgacggtta ccgaatgggc ctcgtcatca agggctgcga ctgtctgctc | 660 |
| tccaagacct accacgagtt cggtactcag tggctccgac ttctcgagga gctgcaccga | 720 |
| gtccccgtca tccccgttgg tctgctccct ccctccatcc ccggctctga caaggacgac | 780 |
| tcttgggttt ccatcaagga gtggctcgac ggccaggaga agggctccgt tgtctacgtt | 840 |
| gctctcggtt ccgaggttct cgtcacccag gaagaggttg tcgagcttgc tcacggtctg | 900 |
| gagctgtccg gtctgccctt cttctgggcc taccgaaagc ccaagggtcc cgccaagtcc | 960 |
| gactccgtcg agcttcccga tggtttcgtc gagcgagtcc gagatcgagg tctggtctgg | 1020 |
| acctcttggg ctccccagct ccgaatcctc tcccacgagt ccgttgctgg tttcctcacc | 1080 |
| cactgcggtt ccggctccat tgtcgagggc ctcatgttcg ccaccctct catcatgctc | 1140 |
| cccatcttcg gtgaccagcc cctcaacgcc cgactccttg aggacaagca ggtcggtatc | 1200 |
| gagatccccc gaaacgagga agatggttct ttcacccgag actctgttgc cgagtctctg | 1260 |
| cgactcgtca tggtcgagga gagggtaag atctaccgag agaaggccaa ggagatgtcc | 1320 |
| aagctctttg gcgacaagga cctccaggac cagtacgtcg acgactttgt cgagtacctc | 1380 |
| cagaagcacc gacgagctgt tgccattgac cacgaaagc | 1419 |

<210> SEQ ID NO 26
<211> LENGTH: 1758
<212> TYPE: DNA
<213> ORGANISM: Yarrowia lipolytica

<400> SEQUENCE: 26

| | |
|---|---|
| atggaatgga tttccacatct ggagaacgat gacgatgtgc tggaaatcga ggactacaag | 60 |
| gtgcgcaagg acgcgctgct gatcgccatt caagtaaccc agaacgccat taacaacgga | 120 |
| actcttcata aggccttgga ggcagccttc gatgctgtga ctgacagaat cgtcatatcg | 180 |
| ccgcaagatt acaccggcgt tatgctgttc ggtgcctcca tgcagtctga ggacgacggt | 240 |
| gacgagttcg atgatgagtc agatacacat ttcattctca agctgggcct tcctaccgct | 300 |
| gctcagatca aacgactcaa acgactggca gaggaccctg atctgggtga gaggttcaag | 360 |
| gtgcaggaag agcctcacct gatggacgtg tttttcgaca tgaaccgcca ttttatcaac | 420 |
| atggcaccca acttcgcgtc cagacgaatc atctatatca cagacgacga taccccccacg | 480 |
| acgaatgagg acgatatcaa caagacacga gttcgaattg aggatctaag ccatctcaag | 540 |
| gtgaaggtcg agcctctttt gatcaaccct tcggaagaca agacgttcga ctcctccaaa | 600 |
| ttctacgctc ttgtgttcaa cgaagacaca tctgtggagc cggttgaggc gatcgatttg | 660 |
| aagcagttta tcaacaaaag aaacgtgctc aatcgatcac tgttcaatgt caaaatggaa | 720 |
| atcggagaag tcttgttgt cggagtaaga ggataccttc tttatgcgga caaaaggct | 780 |
| acttcaacaa cccgaaaggc ctgggtttac actggaggta gaaacccga gattgccaaa | 840 |
| ttagaatcgc aggccgtcac tattgaaagt ggcagaagcg tggacaaggc agatctgaga | 900 |
| aagactttca gtttggaaa tgactatgtt cctttcacag aagaacagct gacgcaaatc | 960 |
| cggtactttg gagagccaat tattcgaatt ctcggcttcc acaattcctc ggacttctcc | 1020 |
| gagctcttca tccacagtgt ccgatcgtca atgttcctat atcccactga tgagaagctt | 1080 |
| gtgggttcga ttcgagcctt ttcagcactc tatcagagtc tcaagaacaa ggataagatg | 1140 |
| gctctggcct gggttattgt ccgcaagggc gccaaaccta ttctggctct tcttattcct | 1200 |

-continued

| | |
|---|---|
| tcaactaagg agatcgaagg tcttcatatg gtcttcttgc cttttacaga tgatattcga | 1260 |
| caagaaccaa agactgaact tgtgtctgcc gccctgagc tcgtggacgc aaccaagaat | 1320 |
| attttcactc gtctacgcat gcctggcgga tttgagtcgc aaagataccc caaccccgt | 1380 |
| ctacagtggc attaccgagt tgtacgagcc atggccttc aggaggaggt tcccaaggta | 1440 |
| cccgaagaca agacgacacc aaagtatcgg tctattgata ctcgagttgg tgatgccatc | 1500 |
| gaggaatgga acaaggtgtt gcagagcagc tccaagcgac ctgcggagga tatctgtaag | 1560 |
| gctgagaaga agtcaagag ttctgacgcg ggccctccgt ccaacgagca aatgcaaaat | 1620 |
| atggttgaga atgacattgt cggcaagctg accgtcgcag aactcagggc ttggggtgct | 1680 |
| gctaacaatg ttgagcccaa tggtagcaag ttgaagaagg actgggttga ggtggtcaaa | 1740 |
| aagtactatg ggaagtga | 1758 |

<210> SEQ ID NO 27
<211> LENGTH: 4245
<212> TYPE: DNA
<213> ORGANISM: Yarrowia lipolytica

<400> SEQUENCE: 27

| | |
|---|---|
| atgggtaaaa ccgaagtgac acaggagagt ctagaatgcg ggtcggtcac gtcctcgctg | 60 |
| gggaaaaagc ccttctccat catcacactc ttcaccggca gacgcattcc tccggtacct | 120 |
| actgaaaaac cagattcggc cgaagaacgg gccgggattc tgtcaaaatt gacctggcaa | 180 |
| tggcttagtc cattgttgaa aactggttac ttacgaaaca ttgaacgtga ggatctgtat | 240 |
| aaagtgagag agagaaactc ggcggctgtg atccagcagc gacttgaatc caatctcgaa | 300 |
| aaacaatacg ccaagtacca cgccaaactg ctcaagaaag gactctcgga gcaagaggcg | 360 |
| catctcaagc tgcaagattc agccaaaccc ctcgtcttgg ctcttaacca gacgtttttt | 420 |
| tggaagttct ggctagccgg actgtttgcc ctagtcaagg acctctgtgg aatcgcctca | 480 |
| gctatggtgt cacgtgttct gatcgaatac attcaagaca gatatctcta caggggggaca | 540 |
| gaccgggaac ctaaggtcgg ccgaggagtc ggcccctcga taggcctatt tctactggcc | 600 |
| gtaggagtca cttctcttctt caaccacatg ttctacaatg tcaagatggt tggagctcag | 660 |
| gctcgtgcag ctctggtggc cgtcatctac agcaagagta cccgtttgag cgccaagggc | 720 |
| cgagctcaat acaccacagg caagatcaca aacttggcag ctattgacgc acatcgagtt | 780 |
| gatctcagtt gtgaatcttt ccactacatt actatctttt tgcctgttgt gggttgtgcc | 840 |
| attgctgtac tcgtggtcaa cctcaaggtc gcagctctag ttggaattgc gaccatgatt | 900 |
| gtcttgatct tgtcgtcgc aggcatcacc atcttctcta tgaagctgcg agccatcatt | 960 |
| gtcaagctca cggataagcg agtcacgtat atccgagaag ctctgcagtc gattagaatc | 1020 |
| atcaagtact acggctggga ggttccttac tgtgacaaga tcaagaaggt gcgtcttgac | 1080 |
| gagacccgta actacgccaa gatgggctcg attcgaggaa cagccattgg tatgtttcag | 1140 |
| gcactcccta ttttggcagg agcgttgtct ttcatcacct acgctgctct aggtcatgga | 1200 |
| actgatcctg ctcgaatgtt ctcttctctg acgcttttca atttactcct gcctgctctt | 1260 |
| gctgttcttc cccaggccct ccaggctgct ggagacgctc gagtggctct cagacgtatc | 1320 |
| cagcggttcc ttggggccga ggagtcgact cccactacag tttttgacgc tactcttgaa | 1380 |
| tctactgatg acgctgtgat tgtggaagac gcctctttca tctggccaga agttgtcgat | 1440 |
| gataagagcg acaaagagaa ggctaaagat gcaaagaagg aggaaaagga taagaagaag | 1500 |

```
gccgagaaga aggccaagaa ggcggccaag aaggcggcca aggagatcgc ggtggttgtg    1560
gaagaggagg tggaacacga aaagaccgag ggatccagtg agtctgaaaa gggtactctt    1620
aagtcgactt tcaagggctt caacaacctg tctttcaaaa tcaagcgggg tgaatttgtc    1680
gttgttaccg gtcccattgg ttctggaaag tcgtctcttc ttgctgccat cactggatct    1740
atggttttga caggcggttc cgtgcgagtg tcgtccacag agtggattgg atgtctggag    1800
ccgtggattc aaaacgccac agttcgagat aacattgtgt ttgggcgaaa attcgactct    1860
gaatggtata gaactgtggt tactgcctgt cagctgagcc aggatctcaa aataatgact    1920
cacggagaca ataccatgat ggagagcga ggcatcacag tttcgggcgg tcaaaaagct    1980
cgaatcaacc tcgcacgtgc tatatatgga accccgaga ttctcatcat ggacgacgtc    2040
ctgtcggctg tggacgctcg agtaggtgct ggtattgtgg acgattgtct tcgaggctta    2100
gccaagaact ccactcgaat tctggccacc catcagctgt ctgtgctgcc taaggctgat    2160
catgtgattt tcatggatgc cgaaggccag tttcatattg gtacgtacca agagctggag    2220
gctgacaatg agcagttcaa ggctcttttg gcggctggtt ccatgtccaa ggaggaggtg    2280
gttgctgtcg acgagactga ggttgttatt gaaggcgatc ttgaagacga ctgcgataac    2340
aaggaggagt atgaggatgc agctgagacc atttccattt tggcagatgc cactcaagag    2400
ctgcaaaagg tgaccactac agtctcggca tttgaggaga acgataacat gatggaggaa    2460
gaagagcgaa tgagagatgc agttggtttg catgtgtact ggcagtattt tcgtcaggcc    2520
aaccccagta gggtcaaggt aatgatgttc attggcatga tcttcatttc catgattgtg    2580
attgcctttc tgtttgtctt cacatctgta tggctctcgt tctggacagg tgaccgtttc    2640
catgcctcca gaaacttcta caccggaatt tacatcatgc tgggtattct tctgcttctt    2700
gctgtggcag gatacatgat tgtcaatgag atcaactctg ccatggcagc aagaaatcta    2760
cacaatcatg ctttggactc ggtgttcgct gcacgaactt cttttcttcga taccactcct    2820
cagggtcgta tcatcaaccg gttcacccga gacacagact ctctggataa cgagctggct    2880
atgcgattga ctatgttgtt ctttggcgtc tccgcattct tctccaactt cctgcttact    2940
tgtgtctacg ttccttatgt gactcttgtg cttgtccctg tcggttttgt cttctacgtt    3000
tctctaggtt actaccgaaa gtcagctcgt gaagtcaagc gaattgactc cattgaacgg    3060
tcgcacatga tgagtgtctt caacgagtcc atttccggta tgcccgtcat catcatgtac    3120
aaggcccagc atcggctcat gaacaagctt caggctactc tcgatgatat ggacagtgcc    3180
tacttcctca ctgctgcaaa ccagcgatgg ctgtctctcc gtctggatgg tctgggttct    3240
ttggtcgttc tggtggccac tattcttgtt gctgtcggag tctttgatct caccccttcc    3300
aacatgggtc tgatcatttc cgcggcctcc tttatccccg aagtcatgtc tatgttgcc    3360
caggccgttg ctgaactcga aaactgcatg aacgccacag agcgaattct ttactacaag    3420
gacaacattc ctgctgaggc tgctcgagaa gtggacggta cagagctcga ccagcgaccc    3480
aactggcctg agcagggagc catcagcttc aacaatgtgt ccatgaagta ccgagatgga    3540
cttccttacg tgctcaagtc attgtctgtc gactttcagg aggacacaa ggtgggtatc    3600
tgtgacgaa caggagccgg taagagtacc atcttgcaga ctctgtatcg aattgtggag    3660
cttgctgagg gttctattac tattgatggt gttgacattt cgactattgg actgcatcag    3720
cttcggtctc agttgtccat cattcccag gagccagttt tgttcctggg caccatccgg    3780
tctaatttgg atcctctgga gcaatactct gatgctgagc tatggggttc tctacgacgg    3840
tctggacttc tcgatgaagg agagactgag ggtaagtttc atctggatca aaaggtggag    3900
```

-continued

```
gctgacggca gcaacttctc tctaggtgag cgacagctgc tgactctagc ccgagcactg    3960
cttagaaaca ccaaaatttt ggtgctggac gaagccacat caaatgtcga ctacaagacg    4020
gacaagctgg ttcaggagac catttcacgg gagtttggcc actgcacgat tctgtgtatc    4080
gcccatcgac tgcgaaccat tgccaagtat gatcgtattt tggtgcttga gtccggcgag    4140
atcaaccagt acgacacgcc ctggaacttg tacaacgaca aggagggtat tttccgaggt    4200
atgtgtgaca cctccgggtt gaacgaggta gacttcaaca agtaa                    4245
```

<210> SEQ ID NO 28
<211> LENGTH: 4245
<212> TYPE: DNA
<213> ORGANISM: Artificial sequence
<220> FEATURE:
<223> OTHER INFORMATION: YALI0E25201g CpO for Y. lipolitica

<400> SEQUENCE: 28

```
atgggtaaga ccgaggtcac tcaggagtct ctcgagtgcg gttccgtcac ctcctctctc      60
ggcaagaagc ccttctccat catcactctc ttcaccggcc gacggatccc tcccgtcccc     120
actgagaagc ccgactccgc tgaggagcga gccggcatcc tctccaagct gacctggcag     180
tggctctctc ctctgctcaa gaccggttac ctccgaaaca tcgagcgaga ggatctgtac     240
aaggtccgag agcgaaactc cgctgccgtt atccagcagc gacttgagtc caacctggag     300
aagcagtacg ccaagtacca cgccaagctc ctcaagaagg gtctgtctga gcaagaggcc     360
cacctcaagc tgcaggactc tgccaagccc cttgtcctgg ccctcaacca gaccttcttc     420
tggaagttct ggctcgctgg tctgttcgcc ctcgtcaagg acctctgtgg cattgcttcc     480
gccatggttt cccgagttct cattgagtac atccaggacc gatacctcta ccgaggtacc     540
gaccgagagc ccaaggtcgg ccgaggtgtc ggtccctcca tcggactctt cctgctggcc     600
gttggtgtca ctttcttctt caaccacatg ttctacaacg tcaagatggt tggtgcccag     660
gcccgagctg ccctcgtcgc tgtcatctac tccaagtcca cccgactgtc cgccaagggt     720
cgagcccagt acaccaccgg caagatcacc aacctcgccg ccattgatgc ccaccgagtc     780
gatctgtctt gcgagtcttt tcactacatc actatcttcc ttcccgtcgt cggctgcgcc     840
attgccgtcc tcgttgtcaa cctcaaggtt gctgctctcg tcggtattgc cactatgatt     900
gtcctcatct ttgtcgttgc tggtatcacc atcttctcca tgaagctccg agccatcatc     960
gtcaagctca ccgacaagcg agtcacctac atccgagagg ctctccagtc catccgaatc    1020
atcaagtact acggctggga ggttccctac tgcgacaaga ttaagaaggt ccgactcgac    1080
gagactcgaa actacgccaa gatgggctcc attcgaggaa ccgctattgg tatgttccag    1140
gctctcccca tcctcgccgg cgctctgtct tttatcacct acgccgccct cggtcacggc    1200
accgaccccg cccgaatgtt ctcttctctc accctcttca acctgctgct cccgctctt     1260 gccgttctcc ccaggcccct ccaggccgct ggtgacgccc gagtcgccct cgacgaatc     1320 cagcgattcc tcggtgctga ggagtccacc cccaccactg tcttcgatgc tactcttgag    1380
tctaccgacg acgccgtcat cgtcgaggac gcctccttca tttggcccga ggtcgttgac    1440
gacaagtccg acaaggagaa ggccaaggat gctaagaaag aggagaagga caagaagaag    1500
gctgagaaga agccaagaa ggccgctaag aaggcagcca aggagatcgc cgttgttgtt     1560
gaggaagagg tcgagcacga gaagaccgaa ggctcctccg agtccgagaa aggtaccctc    1620
aagtccacgt tcaagggttt caacaacctg tctttcaaga tcaagcgagg tgagttcgtt    1680
```

```
gtcgtcactg gtcccatcgg ctccggtaag tcctctctgc tcgctgccat taccggttcc   1740
atggttctga ccggtggttc tgtccgagtc tcttccaccg agtggatcgg ttgcctcgag   1800
ccttggatcc agaacgccac cgtccgagac aacattgtct tcggccgtaa gtttgactcc   1860
gagtggtacc gaaccgttgt caccgcctgc cagctctccc aggacctcaa gatcatgacc   1920
cacggcgata acaccatgat tggtgagcga ggtatcactg tctccggtgg tcagaaggcc   1980
cgaatcaacc tggcccgcgc gatctacggt aaccccgaga ttctcatcat ggacgacgtc   2040
ctctccgccg tcgacgccag ggtcggagcc ggtatcgtcg atgactgtct gagaggcctc   2100
gccaagaact ctacccgaat cctcgccacc caccagctct ctgttctccc caaggccgac   2160
cacgtcatct ttatggacgc cgagggtcag ttccacattg gcacctacca agagctcgag   2220
gctgataacg agcagttcaa ggctctcctc gctgccggct ctatgtccaa agaggaagtc   2280
gttgccgttg acgagactga ggttgtcatt gagggtgacc tcgaggacga ctgtgacaac   2340
aaggaagagt acgaggatgc tgccgagact atctccattc tcgccgacgc cacccaggag   2400
ctccagaagg ttaccaccac cgtttctgct tttgaggaga cgacaacat gatggaggaa   2460 gaagaacgaa tgcgagatgc cgtcggtctg cacgtctact ggcagtactt ccgacaggcc   2520 aaccctctc gagtcaaggt catgatgttc attggtatga ttttcatctc catgattgtc   2580
attgccttcc tcttcgtctt cacctccgtc tggctctcct tttggaccgg tgaccgattc   2640
cacgcttccc gaaacttcta caccggcatc tacatcatgc tcggtatcct ccttctgctc   2700
gccgtcgccg gttacatgat cgtcaatgag atcaactctg ccatggccgc cgaaacctg   2760 cacaaccacg ccctcgactc cgtcttcgcc gctcgaactt ctttcttcga caccactccc   2820
cagggccgaa tcattaaccg attcacccgg gacaccgact ccctcgataa cgaactggcc   2880
atgcgactca ccatgctctt tttcggtgtt tccgcctttt tctccaactt cctcctcacc   2940
tgtgtctacg ttccctacgt caccctggtt cttgtccccg ttggtttcgt cttctacgtt   3000
tccctcggtt actaccgaaa gtccgcccga gaggtcaagc gaatcgactc cattgagcga   3060
tcccacatga tgtccgtctt caacgagtcc atctccggta tgcccgttat catcatgtac   3120
aaggcccagc accgactcat gaacaagctc caggccaccc tcgacgacat ggactccgcc   3180
tacttcctga ccgctgccaa ccagcgatgg ctctccctcc gactggacgg tcttggctct   3240
cttgttgtcc tcgtcgccac cattcttgtc gccgtcggtg tctttgacct cacccccctcc   3300 aacatgggcc tcatcatctc tgctgcctct ttcatccccg aggtcatgtc catggtcgcc   3360
caggccgttg ctgagctcga gaactgcatg aacgctaccg agcgaatcct ctactacaag   3420
gacaacatcc ccgccgaggc tgctcgagag gtcgacggta ccgagcttga tcagcgaccc   3480
aactggcccg agcagggcgc catctccttc aacaacgtgt ccatgaagta ccgagatggt   3540
ctgccctacg tcctcaagtc tctctccgtc gacttccagg gcggccacaa ggtcggtatc   3600
tgcggacgaa ccggtgccgg caagtccact atcctccaga ccctgtaccg aatcgtcgag   3660
ctggccgagg gctccatcac cattgatggt gtcgacatct ccaccattgg cctgcaccag   3720
ctccgatccc agctgtccat catcccccag gagcccgttc tgttccttgg caccatccga   3780
tccaacctcg atccctcga gcagtactcc gacgccgagc tctggggttc tctccgacga   3840
tccggccttc tggacgaggg tgaaaccgag ggtaagttcc acctcgacca gaaggtcgag   3900
gccgatggtt ccaacttctc tctgggtgag cgacagctcc tcaccctcgc ccgagcccctt   3960 ctgcgaaaca ccaagattct tgttctcgac gaggctacct ccaacgtcga ctacaagacc   4020
gataagctcg tccaggagac aatctcccga gagttcggtc actgcaccat tctctgtatc   4080
```

```
gcccaccgac tgcgaaccat cgctaagtac gaccgaattc tcgttctcga gtccggcgag    4140
atcaaccagt acgacacccc ctggaacctc tacaacgaca aggaaggtat cttccgaggc    4200
atgtgcgaca cctccggcct caacgaggtc gactttaata aataa                    4245
```

<210> SEQ ID NO 29
<211> LENGTH: 1414
<212> TYPE: PRT
<213> ORGANISM: Yarrowia lipolytica

<400> SEQUENCE: 29

```
Met Gly Lys Thr Glu Val Thr Gln Glu Ser Leu Glu Cys Gly Ser Val
1               5                   10                  15

Thr Ser Ser Leu Gly Lys Lys Pro Phe Ser Ile Ile Thr Leu Phe Thr
            20                  25                  30

Gly Arg Arg Ile Pro Pro Val Pro Thr Glu Lys Pro Asp Ser Ala Glu
        35                  40                  45

Glu Arg Ala Gly Ile Leu Ser Lys Leu Thr Trp Gln Trp Leu Ser Pro
    50                  55                  60

Leu Leu Lys Thr Gly Tyr Leu Arg Asn Ile Glu Arg Glu Asp Leu Tyr
65                  70                  75                  80

Lys Val Arg Glu Arg Asn Ser Ala Ala Val Ile Gln Gln Arg Leu Glu
                85                  90                  95

Ser Asn Leu Glu Lys Gln Tyr Ala Lys Tyr His Ala Lys Leu Leu Lys
            100                 105                 110

Lys Gly Leu Ser Glu Gln Glu Ala His Leu Lys Leu Gln Asp Ser Ala
        115                 120                 125

Lys Pro Leu Val Leu Ala Leu Asn Gln Thr Phe Phe Trp Lys Phe Trp
    130                 135                 140

Leu Ala Gly Leu Phe Ala Leu Val Lys Asp Leu Cys Gly Ile Ala Ser
145                 150                 155                 160

Ala Met Val Ser Arg Val Leu Ile Glu Tyr Ile Gln Asp Arg Tyr Leu
                165                 170                 175

Tyr Arg Gly Thr Asp Arg Glu Pro Lys Val Gly Arg Gly Val Gly Pro
            180                 185                 190

Ser Ile Gly Leu Phe Leu Leu Ala Val Gly Val Thr Phe Phe Phe Asn
        195                 200                 205

His Met Phe Tyr Asn Val Lys Met Val Gly Ala Gln Ala Arg Ala Ala
    210                 215                 220

Leu Val Ala Val Ile Tyr Ser Lys Ser Thr Arg Leu Ser Ala Lys Gly
225                 230                 235                 240

Arg Ala Gln Tyr Thr Thr Gly Lys Ile Thr Asn Leu Ala Ala Ile Asp
                245                 250                 255

Ala His Arg Val Asp Leu Ser Cys Glu Ser Phe His Tyr Ile Thr Ile
            260                 265                 270

Phe Leu Pro Val Val Gly Cys Ala Ile Ala Val Leu Val Val Asn Leu
        275                 280                 285

Lys Val Ala Ala Leu Val Gly Ile Ala Thr Met Ile Val Leu Ile Phe
    290                 295                 300

Val Val Ala Gly Ile Thr Ile Phe Ser Met Lys Leu Arg Ala Ile Ile
305                 310                 315                 320

Val Lys Leu Thr Asp Lys Arg Val Thr Tyr Ile Arg Glu Ala Leu Gln
                325                 330                 335

Ser Ile Arg Ile Ile Lys Tyr Tyr Gly Trp Glu Val Pro Tyr Cys Asp
```

```
                  340                 345                 350
Lys Ile Lys Lys Val Arg Leu Asp Glu Thr Arg Asn Tyr Ala Lys Met
            355                 360                 365
Gly Ser Ile Arg Gly Thr Ala Ile Gly Met Phe Gln Ala Leu Pro Ile
        370                 375                 380
Leu Ala Gly Ala Leu Ser Phe Ile Thr Tyr Ala Ala Leu Gly His Gly
385                 390                 395                 400
Thr Asp Pro Ala Arg Met Phe Ser Ser Leu Thr Leu Phe Asn Leu Leu
                405                 410                 415
Leu Pro Ala Leu Ala Val Leu Pro Gln Ala Leu Gln Ala Ala Gly Asp
            420                 425                 430
Ala Arg Val Ala Leu Arg Arg Ile Gln Arg Phe Leu Gly Ala Glu Glu
        435                 440                 445
Ser Thr Pro Thr Thr Val Phe Asp Ala Thr Leu Glu Ser Thr Asp Asp
        450                 455                 460
Ala Val Ile Val Glu Asp Ala Ser Phe Ile Trp Pro Glu Val Val Asp
465                 470                 475                 480
Asp Lys Ser Asp Lys Glu Lys Ala Lys Asp Ala Lys Lys Glu Glu Lys
                485                 490                 495
Asp Lys Lys Lys Ala Glu Lys Lys Ala Lys Ala Ala Lys Lys Ala
            500                 505                 510
Ala Lys Glu Ile Ala Val Val Glu Glu Val Glu His Glu Lys
        515                 520                 525
Thr Glu Gly Ser Ser Glu Ser Glu Lys Gly Thr Leu Lys Ser Thr Phe
        530                 535                 540
Lys Gly Phe Asn Asn Leu Ser Phe Lys Ile Lys Arg Gly Glu Phe Val
545                 550                 555                 560
Val Val Thr Gly Pro Ile Gly Ser Gly Lys Ser Ser Leu Leu Ala Ala
                565                 570                 575
Ile Thr Gly Ser Met Val Leu Thr Gly Gly Ser Val Arg Val Ser Ser
            580                 585                 590
Thr Glu Trp Ile Gly Cys Leu Glu Pro Trp Ile Gln Asn Ala Thr Val
        595                 600                 605
Arg Asp Asn Ile Val Phe Gly Arg Lys Phe Asp Ser Glu Trp Tyr Arg
        610                 615                 620
Thr Val Val Thr Ala Cys Gln Leu Ser Gln Asp Leu Lys Ile Met Thr
625                 630                 635                 640
His Gly Asp Asn Thr Met Ile Gly Glu Arg Gly Ile Thr Val Ser Gly
                645                 650                 655
Gly Gln Lys Ala Arg Ile Asn Leu Ala Arg Ala Ile Tyr Gly Asn Pro
            660                 665                 670
Glu Ile Leu Ile Met Asp Asp Val Leu Ser Ala Val Asp Ala Arg Val
        675                 680                 685
Gly Ala Gly Ile Val Asp Asp Cys Leu Arg Gly Leu Ala Lys Asn Ser
        690                 695                 700
Thr Arg Ile Leu Ala Thr His Gln Leu Ser Val Leu Pro Lys Ala Asp
705                 710                 715                 720
His Val Ile Phe Met Asp Ala Glu Gly Gln Phe His Ile Gly Thr Tyr
                725                 730                 735
Gln Glu Leu Glu Ala Asp Asn Glu Gln Phe Lys Ala Leu Leu Ala Ala
            740                 745                 750
Gly Ser Met Ser Lys Glu Glu Val Val Ala Val Asp Glu Thr Glu Val
        755                 760                 765
```

-continued

```
Val Ile Glu Gly Asp Leu Asp Asp Cys Asp Asn Lys Glu Glu Tyr
    770             775             780
Glu Asp Ala Ala Glu Thr Ile Ser Ile Leu Ala Asp Ala Thr Gln Glu
785             790             795             800
Leu Gln Lys Val Thr Thr Thr Val Ser Ala Phe Glu Glu Asn Asp Asn
                805             810             815
Met Met Glu Glu Glu Arg Met Arg Asp Ala Val Gly Leu His Val
            820             825             830
Tyr Trp Gln Tyr Phe Arg Gln Ala Asn Pro Ser Arg Val Lys Val Met
            835             840             845
Met Phe Ile Gly Met Ile Phe Ile Ser Met Ile Val Ile Ala Phe Leu
        850             855             860
Phe Val Phe Thr Ser Val Trp Leu Ser Phe Trp Thr Gly Asp Arg Phe
865             870             875             880
His Ala Ser Arg Asn Phe Tyr Thr Gly Ile Tyr Ile Met Leu Gly Ile
                885             890             895
Leu Leu Leu Leu Ala Val Ala Gly Tyr Met Ile Val Asn Glu Ile Asn
                900             905             910
Ser Ala Met Ala Ala Arg Asn Leu His Asn His Ala Leu Asp Ser Val
            915             920             925
Phe Ala Ala Arg Thr Ser Phe Phe Asp Thr Thr Pro Gln Gly Arg Ile
    930             935             940
Ile Asn Arg Phe Thr Arg Asp Thr Asp Ser Leu Asp Asn Glu Leu Ala
945             950             955             960
Met Arg Leu Thr Met Leu Phe Phe Gly Val Ser Ala Phe Phe Ser Asn
                965             970             975
Phe Leu Leu Thr Cys Val Tyr Val Pro Tyr Val Thr Leu Val Leu Val
                980             985             990
Pro Val Gly Phe Val Phe Tyr Val Ser Leu Gly Tyr Tyr Arg Lys Ser
            995             1000            1005
Ala Arg Glu Val Lys Arg Ile Asp Ser Ile Glu Arg Ser His Met
    1010            1015            1020
Met Ser Val Phe Asn Glu Ser Ile Ser Gly Met Pro Val Ile Ile
    1025            1030            1035
Met Tyr Lys Ala Gln His Arg Leu Met Asn Lys Leu Gln Ala Thr
    1040            1045            1050
Leu Asp Asp Met Asp Ser Ala Tyr Phe Leu Thr Ala Ala Asn Gln
    1055            1060            1065
Arg Trp Leu Ser Leu Arg Leu Asp Gly Leu Gly Ser Leu Val Val
    1070            1075            1080
Leu Val Ala Thr Ile Leu Val Ala Val Gly Val Phe Asp Leu Thr
    1085            1090            1095
Pro Ser Asn Met Gly Leu Ile Ile Ser Ala Ala Ser Phe Ile Pro
    1100            1105            1110
Glu Val Met Ser Met Val Ala Gln Ala Val Ala Glu Leu Glu Asn
    1115            1120            1125
Cys Met Asn Ala Thr Glu Arg Ile Leu Tyr Tyr Lys Asp Asn Ile
    1130            1135            1140
Pro Ala Glu Ala Ala Arg Glu Val Asp Gly Thr Glu Leu Asp Gln
    1145            1150            1155
Arg Pro Asn Trp Pro Glu Gln Gly Ala Ile Ser Phe Asn Asn Val
    1160            1165            1170
```

Ser Met Lys Tyr Arg Asp Gly Leu Pro Tyr Val Leu Lys Ser Leu
1175                1180                1185

Ser Val Asp Phe Gln Gly Gly His Lys Val Gly Ile Cys Gly Arg
1190                1195                1200

Thr Gly Ala Gly Lys Ser Thr Ile Leu Gln Thr Leu Tyr Arg Ile
1205                1210                1215

Val Glu Leu Ala Glu Gly Ser Ile Thr Ile Asp Gly Val Asp Ile
1220                1225                1230

Ser Thr Ile Gly Leu His Gln Leu Arg Ser Gln Leu Ser Ile Ile
1235                1240                1245

Pro Gln Glu Pro Val Leu Phe Leu Gly Thr Ile Arg Ser Asn Leu
1250                1255                1260

Asp Pro Leu Glu Gln Tyr Ser Asp Ala Glu Leu Trp Gly Ser Leu
1265                1270                1275

Arg Arg Ser Gly Leu Leu Asp Glu Gly Glu Thr Glu Gly Lys Phe
1280                1285                1290

His Leu Asp Gln Lys Val Glu Ala Asp Gly Ser Asn Phe Ser Leu
1295                1300                1305

Gly Glu Arg Gln Leu Leu Thr Leu Ala Arg Ala Leu Leu Arg Asn
1310                1315                1320

Thr Lys Ile Leu Val Leu Asp Glu Ala Thr Ser Asn Val Asp Tyr
1325                1330                1335

Lys Thr Asp Lys Leu Val Gln Glu Thr Ile Ser Arg Glu Phe Gly
1340                1345                1350

His Cys Thr Ile Leu Cys Ile Ala His Arg Leu Arg Thr Ile Ala
1355                1360                1365

Lys Tyr Asp Arg Ile Leu Val Leu Glu Ser Gly Glu Ile Asn Gln
1370                1375                1380

Tyr Asp Thr Pro Trp Asn Leu Tyr Asn Asp Lys Glu Gly Ile Phe
1385                1390                1395

Arg Gly Met Cys Asp Thr Ser Gly Leu Asn Glu Val Asp Phe Asn
1400                1405                1410

Lys

<210> SEQ ID NO 30
<211> LENGTH: 1000
<212> TYPE: DNA
<213> ORGANISM: Yarrowia lipolytica

<400> SEQUENCE: 30
cggttgagag ttcaagaaca cgaccaagta accccgagaa agtgtcgatg gatacagaga      60
aaacaatatc gcagatattg acaacaaact tgcaacgaga gccctctaca tgctccaata     120
ttcttcttcc agacctaccc gttcacacaa ctacaagttg ccgccttaaa caacaacgtg     180
gtcaactccg gagttaacag aagcataata atgtgatgga atttggaggt tggggagaga     240
cagtttggac cggagacacg ccacggggaa atcatcataa acattggtaa aatgccaaaa     300
aaaatttata catggtagca aaagcatcct ggagaactcc taagtatgtc agggtcccaa     360
aaacctcgtt aatggaggcc tgcggacttc ttccgtgaca ttgtgaacca ttaatacaac     420
ctgaaaagac catctgcaaa acaccagtga tagtggttcc aacgcaactt cgtgcacact     480
caacgctacc actgctagac ctaccgccgt tagacctatt gtatcgccgc caccgttctt     540
aaatgcagat gaagtaaaca ctgccgttcg gtccaataat taatgttgct ccgccatgct     600
cagttttttt tctttctttt cggcaaaata accttcgcag tcatgtgaga tatcgcacga     660

```
caagatgtga ctaacatgcc aacggcggct gcccccaagg tgtatatgag taccaaatta      720
gggcatgata caagaatacc tttcgaaaag ccggaacaag ataaagcagc ccaacccttta     780 taacggccag ctagcgccaa acttgctcgc cccgagcccc accgcttct catccgtacg       840 ccatttcgtg ccacgtatcc agaaagttct actcccagca cagggttagg ggtgttgcca     900
ttctgggtca ctccccacca ccacagcatg ttttttcctc tctcccgaca accacaactc     960
tctagtttac actaaccaca cacgacacca atttaaaaa                            1000
```

<210> SEQ ID NO 31
<211> LENGTH: 300
<212> TYPE: DNA
<213> ORGANISM: Yarrowia lipolytica
<400> SEQUENCE: 31

```
atgcaaacca gtaatttat tgtgtagtct aggattgaca tttgattacc gtgtacatta       60
aatgaatgat tgtaaattga agaggaagt gtagcaatgg ttgaatgggg agtaatgggt      120
tactgtaatt gcatgtccca ccttctttgc accgttcttg ttgtatacag tacaatacat     180 acataccta tgtatgtttt ttgtgaatat gatgagtcta ctactacagt aaatcagctt      240
tgatccctgc cagaatgtgt gtacacagta tgggactctc atccctgta caatataata     300
```

<210> SEQ ID NO 32
<211> LENGTH: 912
<212> TYPE: DNA
<213> ORGANISM: Artificial sequence
<220> FEATURE:
<223> OTHER INFORMATION: carG nucleic acid sequence codon optimized for
      Y. lipolitica <400> SEQUENCE: 32

```
atgctcaact ctcacaaccg aaccgaggag cgatccaccg aggatattat tctcgagcct      60
tacacctacc tcatttctca gcccggaaag gacattcgag ctaagctcat ttctgccttt     120
gacctctggc tgcacgttcc taaggatgtt ctttgcgtca tcaacaagat tatcggtatg     180
ctgcacaacg cctctcttat gattgacgat gttcaggacg actctgatct ccgacgagga    240
gtccccgttg ctcaccacat ttacggtgtc cctcagacta ttaacaccgc taactacgtg    300
attttcctcg cccttcagga ggttatgaag ctgaacatcc cttctatgat gcaggtgtgt    360
accgaggagc ttattaacct ccaccgaggt cagggaattg agctgtactg gcgagattcc    420
ctcacttgtc ccactgagga ggagtacatt gatatggtta caacaagac tctctggcctc    480 cttcgacttg ccgtccgact gatgcaggct gcttctgagt ccgacatcga ctacacccct    540
ctcgtcaaca ttatcggaat tcacttccag gttcgagatg actacatgaa cctccagtcc    600
acctcttaca ctaacaacaa gggcttttgc gaggacctga ccgagggaaa gttctccttc    660
cctattattc acgctattcg aaaggacccc tctaaccgac agctcctgaa cattatctct    720
cagaagccca cctccattga ggttaagaag tacgctcttg aggtgatccg aaaggctgga    780
tcttttgagt acgttcgaga gttccttcga cagaaggagg ctgagtcct gaaggagatc    840 aagcgacttg gcggcaaccc tctcctcgag aagtacattg agactattcg agtcgaggct    900
actaacgact aa                                                          912
```

<210> SEQ ID NO 33
<211> LENGTH: 1419
<212> TYPE: DNA
<213> ORGANISM: Artificial sequence
<220> FEATURE:
<223> OTHER INFORMATION: UGT2_6b CpO for Y. lipolitica

<400> SEQUENCE: 33

| | |
|---|---|
| atggctactt ccgactccat tgtcgacgac cgaaagaagc tccacattgt catgttcccc | 60 |
| tggctcgcct ttggccacat cattccctac ctcgagcttt ccaagctcat tgcccagaag | 120 |
| ggccacaagg tttctttcct ctccaccacc aagaacattg accgactctc ctcccacatc | 180 |
| tctcctctca tcaacgttgt ccagctcacc ctcccccgag tccaggagct gcccgaggac | 240 |
| gccgaggcca ccaccgatgt ccaccccgag atatcccct acctcaagaa ggcctccgac | 300 |
| ggtctgcagc ccgaggtcac cgagttcctc gagcagcact ctcccgactg gatcatctac | 360 |
| gactacaccc actactggct cccctccatt gccaccaagc acgtgtgtctc tcgagcccac | 420 |
| ttctccgtca ccaccccctg gccattgcc tacatgggcc ccactgctga cgccatgatc | 480 |
| aacggttccg atggccgaac cacccccgag gacttcactg tccctcccaa gtggttcccc | 540 |
| ttccccacca aggtctgctg gcgaaagcac gatctggccc gactcgttcc ctacaaggcc | 600 |
| cccggtatct ccgacggcta ccgaatgggt ctggtcatca agggctgcga ctgtctgctc | 660 |
| tccaagacct accacgagtt tggcacccag tggctccgac cctcgagac tctccaccga | 720 |
| aagcccgtca tcccgtcgg tctgctccct ccctccatcc ccggctccga caaggacgac | 780 |
| tcttgggttt ccatcaagga gtggctcgac ggccaggaga agggctctgt tgtctacgtt | 840 |
| gctctcggtt ccgaggttct cgtcacccag gacgaggttg ttgagctggc ccacggtctg | 900 |
| gagctgtccg gcctcccctt cgtctgggct taccgaaacc ccaagggtcc cgccaagtcc | 960 |
| gactccgtcg agcttcccga tggtttcgtc gagcgagtcc gagatcgagg tctggtctgg | 1020 |
| acctcttggg ctcccccagct ccgaatcctc tcccacgagt ccgtctgtgg tttcctcacc | 1080 |
| cactgcggtt ccggctccat cgtcgagggt ctgatgttcg ccaccccct catcatgctc | 1140 |
| cccatcttcg gtgaccagcc cctcaacgcc cgactccttg aggacaagca ggtcggtatc | 1200 |
| gagatccccc gaaacgaaga ggacggttcc ttcacccgag actctgttgc tgagtctctc | 1260 |
| cgactcgtca tggtcgagga gagggtaag atctaccgag agaaggccaa ggagatgtcc | 1320 |
| aagctgttcg gtgacaagga tctccaggac cagtacgtcg acgactttgt cgagtacctc | 1380 |
| cagaagcacc gacgagctgt tgccattgac cacgagtct | 1419 |

<210> SEQ ID NO 34
<211> LENGTH: 1341
<212> TYPE: DNA
<213> ORGANISM: Artificial sequence
<220> FEATURE:
<223> OTHER INFORMATION: RT18 nucleic acid sequence CpO for Y. lipolitica

<400> SEQUENCE: 34

| | |
|---|---|
| atgtccacca ccctcaaggt cctcatgttc cccttcctcg cttacggcca catctctccc | 60 |
| tacctcaacg ttgccaagaa gctcgccgac cgaggcttcc tcatctacct ctgttccacc | 120 |
| cccatcaacc tcaagtccac catcaacaag atccccgaga gtacgccga ctccatccag | 180 |
| ctcatcgaac tccatctccc cgagcttccc gagctgcctc ccactaccac caccaccaac | 240 |
| ggtctgcctc ccaacctcaa ccacatcctc cgacgagccc tcaagatgtc caagcccaac | 300 |
| ttctccaaga tcatgcagaa cctgaagccc gatctgctca tctacgacat tctccagcag | 360 |
| tgggccgagg atgtcgccac cgagcttaac atccccgccg tcaagctgct cacctctggt | 420 |
| gttgctgttt tctcttactt cttcaacctc accaagaagc ccgaggtcga gttcccctac | 480 |

-continued

```
cccgctatct acctccgaaa gatcgagctg gtccgatggt gcgagactct gtccaagcac      540
aacaaggaag gtgaggagca cgacgacggc ctcgcctacg gcaacatgca gatcatgctc      600
atgtccactt ccaagatcct cgaggccaag tacattgact actgcattga gctgaccaac     660
tggaaggtcg tccccgtcgg ctctctcgtc caggactcca tcaccaacga cgccgctgac     720
gacgacatgg aactcattga ctggctcggt actaaggacg agaactccac cgtctttgtc     780
tcttttggct ccgagtactt cctctccaaa gaggacgttg aagaggttgc cttcggtctg     840
gagctgtcca acgtcaactt catctgggtt gtccgattcc ccaagggtga ggagaagaac     900
ctcgaggacg ttctgcccaa gggcttcttc gagcgaatcg gtgagcgagg ccgagtcctc     960
gacaagtttg ctccccagcc ccgaattctc aaccacccct ctaccggtgg tttcatctct    1020
cactgtggct ggaactccgc catggagtcc attgactttg gtgtccccat tgtcgccatg    1080
cccatgcagc tcgaccagcc catgaacgcc cgactcattg tcgagcttgg tgttgccgtc    1140
gagattgtcc gagatgatga tggtaagatc taccgaggtg agattgctga gactctcaag    1200
ggtgtcatca ccggcgagat tggtgagatc ctccgagcca aggtccgaga catctccaag    1260
aacctcaagg ccatcaagga cgaggagatg gacgttgctg cccaggagct gatccagctc    1320
tgccgaaact ccaataaata a                                              1341
```